(12) United States Patent
Shiota et al.

(10) Patent No.: US 9,914,687 B2
(45) Date of Patent: Mar. 13, 2018

(54) COMPOSITION CONTAINING VINYL-GROUP-CONTAINING COMPOUND

(71) Applicant: TOKYO OHKA KOGYO CO., LTD., Kawasaki-shi (JP)

(72) Inventors: Dai Shiota, Kawasaki (JP); Kunihiro Noda, Kawasaki (JP); Hiroki Chisaka, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 14/780,786

(22) PCT Filed: Mar. 28, 2014

(86) PCT No.: PCT/JP2014/059309
§ 371 (c)(1),
(2) Date: Sep. 28, 2015

(87) PCT Pub. No.: WO2014/157675
PCT Pub. Date: Oct. 2, 2014

(65) Prior Publication Data
US 2016/0046552 A1    Feb. 18, 2016

(30) Foreign Application Priority Data

Mar. 29, 2013  (JP) ................. 2013-075398

(51) Int. Cl.
*G03F 7/004* (2006.01)
*G03F 7/30* (2006.01)
(Continued)

(52) U.S. Cl.
CPC .......... *C07C 43/215* (2013.01); *C07C 43/225* (2013.01); *C07C 69/54* (2013.01);
(Continued)

(58) Field of Classification Search
CPC .......... G03F 7/31; G03F 7/0045; G03F 7/027; G03F 7/028; G03F 7/30
(Continued)

(56) References Cited

U.S. PATENT DOCUMENTS 4,069,056 A    1/1978 Crivello
4,473,626 A    9/1984 Molaire et al.
(Continued)

FOREIGN PATENT DOCUMENTS

CN    101685165 A    3/2010
EP    0428706 A1    5/1991
(Continued)

OTHER PUBLICATIONS

Konrad H. Bleicher, et al., New phenylfluorenyl based linkers for solid phase synthesis, Tetrahedron Letters, 2000, 41(47), pp. 9037-9042, Scheme 1. Compound(4).
Marilia O. F. Goulart, et al., Electroorganic Reactions. 31. Quinonemethide Radical-Anions and Dianions: Their Cathodic Generation and Reactivity, Journal of Organic Chemistry, 1988, 53(11), pp. 2520-2525, p. 2521 Compound (23).
Bohumir Koutek, et al., Perturbation of the Fuchsone Chromophore by 3, 5-Methyl Substitusion. Sterically Crowded Exocyclic Double Bond, Collection of Czechoslovak Chemical Communications, 1981, 46(10), pp. 2540-2556, p. 2547 Scheme 3.
Hans-Dieter Becker, et al., Preparation and Reactions of 2, 6-Di-tert-butyl-4-(9-fluorenylidene)-1, 4-benzoquinone, Journal of Organic Chemistry, 1976, 41(2), pp. 214-221, Table II Compound 11a.
Martin Stiles, et al., Tribenzotropone from a 1, 3-Rearrangement, Journal of Organic Chemistry, 1957, 22, pp. 1243-1246, p. 1245 9-o-hydroxyphenyl-9-fluorenol.

(Continued)

*Primary Examiner* — John S Chu
(74) *Attorney, Agent, or Firm* — Knobbe Martens Olson & Bear LLP

(57) ABSTRACT

A composition containing a novel vinyl-group-containing compound. This composition contains a vinyl-group-containing compound represented by general formula (1). In the formula: $W^1$ and $W^2$ represent a group represented by general formula (2) (where a ring (Z) is an aromatic hydrocarbon ring, X is a single bond or —S—, $R^1$ is a single bond or a C1-4 alkylene group, $R^2$ is a specific substituent group such as a monovalent hydrocarbon, and m is an integer equal to 0 or higher), a group represented by general formula (4) (where the ring (Z), X, $R^1$, $R^2$, and m are as previously stated), a hydroxyl group, or a (meth)acryloyloxy group; rings ($Y^1$, $Y^2$) are aromatic hydrocarbon rings; R represents a single bond or a specific divalent group; $R^{3a}$ and $R^{3b}$ represent a cyano group, a halogen atom, or a monovalent hydrocarbon group; and n1 and n2 are integers of 0-4.

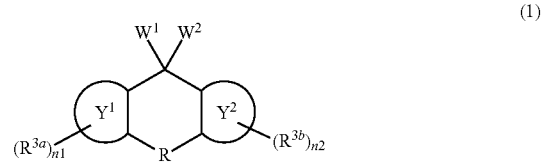

(1)

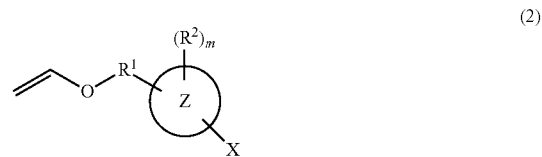

(2)

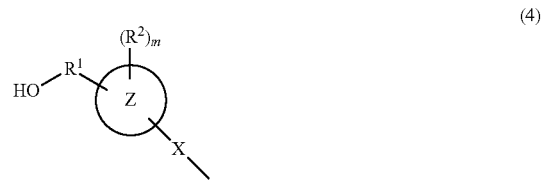

(4)

12 Claims, No Drawings

(51) Int. Cl.
| | | |
|---|---|---|
| C07C 43/215 | (2006.01) | |
| G03F 7/028 | (2006.01) | |
| C07C 69/54 | (2006.01) | |
| C08F 16/12 | (2006.01) | |
| C08F 16/32 | (2006.01) | |
| G03F 7/027 | (2006.01) | |
| C08F 222/10 | (2006.01) | |
| C08L 33/14 | (2006.01) | |
| C07C 43/225 | (2006.01) | |
| C07C 309/66 | (2006.01) | |
| C08F 16/24 | (2006.01) | |
| C08F 16/30 | (2006.01) | |
| C08F 22/14 | (2006.01) | |
| G03F 7/038 | (2006.01) | |

(52) U.S. Cl.
CPC ............ *C07C 309/66* (2013.01); *C08F 16/12* (2013.01); *C08F 16/24* (2013.01); *C08F 16/30* (2013.01); *C08F 16/32* (2013.01); *C08F 22/14* (2013.01); *C08F 222/10* (2013.01); *C08L 33/14* (2013.01); *G03F 7/0045* (2013.01); *G03F 7/027* (2013.01); *G03F 7/028* (2013.01); *G03F 7/0382* (2013.01); *C07C 2603/18* (2017.05)

(58) Field of Classification Search
USPC .......................................... 430/281.1, 288.1
See application file for complete search history.

(56) References Cited

U.S. PATENT DOCUMENTS

| | | | |
|---|---|---|---|
| 5,176,977 | A | 1/1993 | Molaire et al. |
| 7,534,547 | B2 | 5/2009 | Hanabata et al. |
| 2003/0064168 | A1 | 4/2003 | Kato et al. |
| 2003/0211421 | A1 | 11/2003 | Hanabata et al. |
| 2004/0106004 | A1 | 6/2004 | Li |
| 2005/0158659 | A1* | 7/2005 | Lee ................. G03F 7/0007 430/271.1 |
| 2005/0175930 | A1* | 8/2005 | Lee ................. G03F 7/0007 430/270.1 |
| 2006/0166114 | A1* | 7/2006 | Lee ................. G03F 7/0007 430/7 |
| 2007/0117876 | A1* | 5/2007 | Lee ................. G03F 7/0007 522/71 |
| 2008/0220372 | A1* | 9/2008 | Lee ................. G03F 7/0007 430/281.1 |
| 2009/0068569 | A1 | 3/2009 | Seta et al. |
| 2010/0076138 | A1 | 3/2010 | Iwasa |
| 2016/0046551 | A1* | 2/2016 | Shiota .............. C07C 69/54 558/46 |
| 2016/0046552 | A1 | 2/2016 | Shiota et al. |
| 2016/0046742 | A1* | 2/2016 | Shiota .............. C07C 41/06 524/554 |

FOREIGN PATENT DOCUMENTS

| | | |
|---|---|---|
| EP | 0598552 A2 | 5/1994 |
| EP | 2980059 A1 | 3/2014 |
| EP | 2980057 A1 | 2/2016 |
| EP | 2980058 A1 | 2/2016 |
| JP | 2000-178115 A | 6/2000 |
| JP | 2002-255929 A | 9/2002 |
| JP | 2004-137262 | 5/2004 |
| JP | 2006-152115 | 6/2006 |
| JP | 2006-282875 A | 10/2006 |
| JP | 2006-327990 A | 12/2006 |
| JP | 2009-013096 | 1/2009 |
| JP | 2009-215447 A | 9/2009 |
| JP | 201007470 * | 2/2010 |
| JP | 2010-097194 | 4/2010 |
| JP | 2011-090774 | 5/2011 |
| JP | 2011-201791 | 10/2011 |
| JP | 2012-063728 A | 3/2012 |
| JP | 2012-068652 A | 4/2012 |
| JP | 2012-118551 A | 6/2012 |
| JP | 2013028574 A * | 2/2013 |
| JP | WO2013/022065 A1 | 3/2015 |
| KR | 10-2003-0005419 A | 1/2003 |
| WO | WO 90/15043 A2 | 12/1990 |
| WO | WO2002/079131 | 10/2002 |
| WO | WO2006/132139 | 12/2006 |
| WO | WO2013/018302 | 2/2013 |
| WO | WO2013018302 * | 2/2013 |

OTHER PUBLICATIONS

Ching-Nan Chuang et al: "Synthesis and characterization of fluorene-derived PU as a thermo cross-linked hole-transporting layer for PLED", Polymer., vol. 53, No. 10, Apr. 1, 2012, pp. 2001-2007, XP055250560, GB.
Database CAPLUS [Online] Chemical Abstracts Service, Columbus, Ohio, US; XP002754507, retrieved from STN accession No. 80826-88-6P Databese accession No. 1978:423387 & Lewis, Terry Warren TI—Dehydration Reactions in the Organic Solid State: "Dehydration reactions in the organic solid state", INT, 1977.
Gyoo-Soon Park et al: "H-Bonding Controls the Regio-selectivities on the Acid-catalyzed Reaction of Fluorenone with Phenol Derivatives", Bulletin of the Korean Chemical Society, vol. 31, No. 7, Jul. 20, 2010, pp. 1837-1838, XP055251273, KR.
Shoji Kajigaeshi et al: "Spirofluorenes. V. Synthesis of spirofluorenes containing o-phenylene group in their system.", Nippon Kagaku Kaishi: Journal of the Chemical Society of Japan., No. 10, Jan. 1, 1989, pp. 1757-1764, XP055251263, JP.
Yoshihisa Okamoto et al: "Novel vinyl ether thermosetting resins", Polymer, Jan. 1, 1993 (Jan. 1, 1993), pp. 691-695, XP055251276.
Partial supplementary European search report in European Patent Application No. 14773950.2, dated Mar. 9, 2016.
Office Action in Korean Patent Application No. 10-2015-7030693, dated Oct. 14, 2016.
Office Action issued in Korean Patent Application No. 10-2015-7030693, dated Jun. 20, 2017.
Office Action issued in Korean Patent Application No. 10-2015-7030995, dated May 4, 2017.
Carrie Y. K. Chan et al: "Polycyclotrimerization of Dinitriles: A New Polymerization Route for the Construction of Soluble Nitrogen-Rich Polytriazines with Hyperbranched Structures and Functional Properties", Macromolecules, vol. 46, No. 24, Dec. 23, 2013 (Dec. 23, 2013), pp. 9494-9506, XP055251844, US.
Mitsuaki Yamada et al: "Synthesis of Fluorenebisphenoxy Derivatives by Acid-sulfur Compound Catalyzed Condensation Reaction", Chemistry Letters, Chemical Society of Japan, Japan, vol. 10, Jan. 1, 1998 (Jan. 1, 1998), pp. 1055-1056, XP002361848.
Nelson Felix et al., Acid-Labile, Chain-Scission Polymer Systems Used as Positive-Tone Photoresists Developable in Supercritical CO2, Chem. Mater., 2008, 20(9), pp. 2932-2936, Abstract, Fig. 2-3, Scheme 1.
Nelson M. Felix et al., Achieving Small Dimensions with an Environmentally Friendly Solvent: Photoresist Development Using Supercritical CO2, Proc. of SPIE, 2008, vol. 6923, pp. 69233L-1-69233L-11, Abstract, Fig. 6.
Sadaaki Nunomoto et al: "Properties of polymers cross-linked by a fluorene ring or siloxane-containing cross-linking agents", Designed Monomers and Polymers, vol. 4, No. 1, Mar. 1, 2001 (Mar. 1, 2001), pp. 1-8, XP055286865, NL.
Toshihide Hasegawa et al: "Diphenolic 9,9-Diarylfluorene Trimers and Derivatives Possessing Flexible Alkylene Chain Spacers: Synthesis of the Monomers, Their Polymerization, and Properties of the Resulting Polymers", Macromolecules, vol. 43, No. 1, Jan. 12, 2010 (Jan. 12, 2010), pp. 131-136, XP055251841, US.
CAS reaction database (Jun. 28, 2001)—included in the Office Action for U.S. Appl. No. 14/780,760 dated Jan. 31, 2017.
Extended European search report for European Patent Application No. 14774297.7 dated Mar. 14, 2016.
Extended European search report for European Patent Application No. 14775291.9 dated Jul. 25, 2016.

(56) References Cited

OTHER PUBLICATIONS

International Search Report for International Application No. PCT/JP2014/059308 dated Apr. 22, 2014.
Office Action for Chinese Patent Application No. 201480018794.2 dated Apr. 25, 2016.
Office Action for U.S. Appl. No. 14/780,743 dated Dec. 23, 2016.
Partial supplementary European search report for European Patent Application No. 14775291.9 dated Mar. 24, 2016.
Encyclopedia of Polymer Science and Technology, vol. 10, Mar. 2004, pp. 807-836.
Office Action issued in U.S. Appl. No. 14/780,743, dated Sep. 25, 2017.

* cited by examiner

COMPOSITION CONTAINING VINYL-GROUP-CONTAINING COMPOUND

This application is the U.S. National Phase under 35 U.S.C. § 371 of International Application PCT/JP2014/059309, filed Mar. 28, 2014, designating the U.S., and published in Japanese as WO 2014/157675 on Oct. 2, 2014, which claims priority to Japanese Patent Application No. 2013-075398, filed Mar. 29, 2013, the entire contents of which are incorporated herein by reference.

TECHNICAL FIELD

The present invention relates to a composition comprising a vinyl-group-containing compound.

BACKGROUND ART

Fused polycyclic compounds have various excellent functions and thus have been used for various applications. For example, compounds having a fluorene skeleton (for example, 9,9-bisphenylfluorene skeleton) that are fused polycyclic aromatic compounds are known to have excellent functions in terms of optical properties such as light transmittance and refractive index and thermal properties such as heat resistance. Therefore, compounds having a fluorene skeleton are used as raw materials for optical members such as lenses, prisms, filters, image display materials, optical disk substrates, optical fibers, optical waveguides, casing materials, films, and coating materials. Such compounds having a fluorene skeleton include, for example, compounds disclosed in Patent Document 1.

Patent Document 1: Japanese Unexamined Patent Application, Publication No. 2011-201791

DISCLOSURE OF THE INVENTION

Problems to be Solved by the Invention

An object of the present invention is to provide a composition comprising a novel vinyl-group-containing compound.

Means for Solving the Problems

The present inventors have made extensive and intensive studies with a view to solving the above problems. As a result, the present inventors have found compositions comprising novel vinyl-group-containing compounds, leading to the completion of the present invention. Specifically, the present invention provides the following.

According to a first aspect of the present invention, there is provided a composition comprising a vinyl-group-containing compound represented by the following general formula (1):

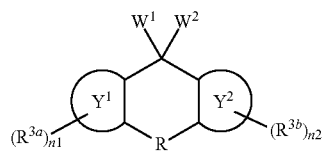

(1)

(wherein $W^1$ and $W^2$ each independently represent a group represented by the following general formula (2), a group represented by the following general formula (4), a hydroxyl group, or a (meth)acryloyloxy group, provided that $W^1$ and $W^2$ do not simultaneously represent a hydroxyl group or the group represented by the following general formula (4); a ring $Y^1$ and a ring $Y^2$, which may be the same or different, represent an aromatic hydrocarbon ring; R represents a single bond, an optionally substituted methylene group, an ethylene group that is optionally substituted and may contain a hetero atom between two carbon atoms, a group represented by —O—, a group represented by —NH—, or a group represented by —S—; $R^{3a}$ and $R^{3b}$ each independently represent a cyano group, a halogen atom, or a monovalent hydrocarbon group; and n1 and n2 each independently represent an integer of 0 to 4.)

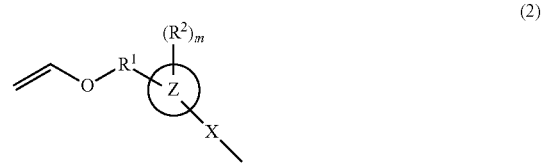

(2)

(wherein a ring Z represents an aromatic hydrocarbon ring; X represents a single bond or a group represented by —S—; $R^1$ represents a single bond or an alkylene group having 1 to 4 carbon atoms; $R^2$ represents a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; $R^{4a}$ to $R^{4d}$ each independently represent a monovalent hydrocarbon group; and m is an integer of 0 or more.)

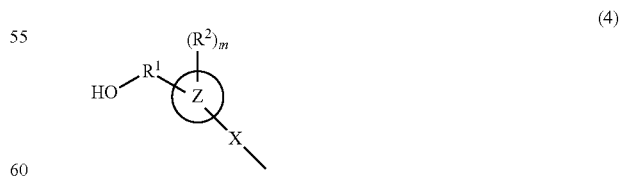

(4)

(wherein a ring Z, X, $R^1$, $R^2$, and m are as defined above.)

According to a second aspect of the present invention, there is provided a composition comprising a monovinyl-group- and mono(meth)acryloyloxy-group-containing compound represented by the following general formula (10):

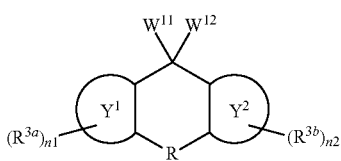
(10)

(wherein any one of $W^{11}$ and $W^{12}$ represents a group represented by the following general formula (2) while the other represents a group represented by the following general formula (11) or (12); and a ring $Y^1$, a ring $Y^2$, R, $R^{3a}$, $R^{3b}$, n1, and n2 are as defined above.)

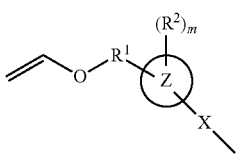
(2)

(wherein a ring Z, X, $R^1$, $R^2$, and m are as defined above.)

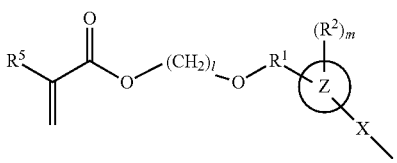
(11)

(wherein $R^5$ represents a hydrogen atom or a methyl group; l represents an integer of 1 to 4; and a ring Z, X, $R^1$, $R^2$, and m are as defined above.)

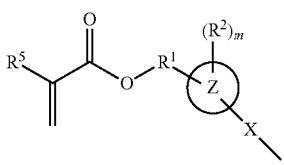
(12)

(wherein a ring Z, X, $R^1$, $R^2$, $R^5$, and m are as defined above.)

According to a third aspect of the present invention, there is provided a composition comprising a (meth)acryloyloxy-group-containing compound represented by the following general formula (19).

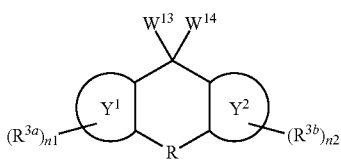
(19)

(wherein $W^{13}$ and $W^{14}$ each independently represent a group represented by the general formula (12), a hydroxyl group, or a (meth)acryloyloxy group, provided that at least one of $W^{13}$ and $W^{14}$ represents a group represented by the following general formula (12); a ring $Y^1$, a ring $Y^2$, R, $R^{3a}$, $R^{3b}$, n1, and n2 are as defined above.)

According to a fourth aspect of the present invention, there is provided a molded product comprising a cured product of the above composition that further comprises an acid generating agent or a base generating agent.

Effects of the Invention

The present invention can provide a composition comprising a novel vinyl-group-containing compound.

PREFERRED MODE FOR CARRYING OUT THE INVENTION

Composition

The composition according to the present invention comprises at least a vinyl-group-containing compound represented by the general formula (1), a monovinyl-group- and mono(meth)acryloyloxy-group-containing compound represented by the general formula (10) and/or a (meth)acryloyloxy-group-containing compound represented by the general formula (19). The composition according to the present invention, when heated, can be cured. When the composition according to the present invention comprises a photobase generating agent, a photoacid generating agent, a photopolymerization initiator, and a photopolymerizable compound such as a photopolymerizable monomer, the composition is photosensitive. Each of the components contained in the composition according to the present invention will be described in detail.

Vinyl-Group-Containing Compounds Represented by the General Formula (1)

Vinyl-group-containing compounds contained in the composition according to the present invention are represented by the following general formula (1). The vinyl-group-containing compound may be used solely or in a combination of two or more thereof.

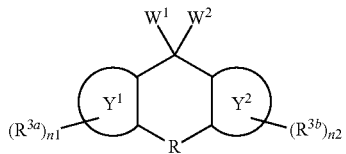
(1)

In the general formula (1), $W^1$ and $W^2$ each independently represent a group represented by the following general formula (2), a group represented by the following general formula (4), a hydroxyl group, or a (meth)acryloyloxy group, provided that $W^1$ and $W^2$ do not simultaneously represent a hydroxyl group or a group represented by the following general formula (4). Preferably, at least one of $W^1$ and $W^2$ represents a group represented by the following general formula (2). More preferably, both $W^1$ and $W^2$ represent a group represented by the following general formula (2). The term "(meth)acryloyl" as used herein means both acryloyl and methacryloyl.

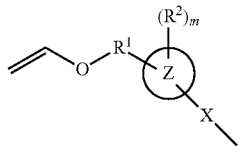
(2)

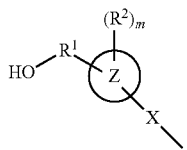

(4)

In the general formulae (2) and (4), examples of the ring Z include benzene rings and fused polycyclic aromatic hydrocarbon rings [for example, fused di- to tetracyclic aromatic hydrocarbon rings such as fused dicyclic hydrocarbon rings (for example, $C_{8-20}$ fused dicyclic hydrocarbon rings, preferably $C_{10-16}$ fused dicyclic hydrocarbon rings, such as naphthalene rings) and fused tricyclic aromatic hydrocarbon rings (for example, anthracene rings or phenanthrene rings). The ring Z is preferably a benzene ring or a naphthalene ring, more preferably a naphthalene ring. When both $W^1$ and $W^2$ represent a group represented by the general formula (2), or when one of $W^1$ and $W^2$ represents a group represented by the general formula (2) while the other represents a group represented by the general formula (4), the ring Z contained in $W^1$ may be the same as or different from the ring Z contained in $W^2$. For example, one of the rings may represent a benzene ring with the other ring representing a naphthalene ring or the like. Particularly preferably, both the rings represent a naphthalene ring. The position of substitution of the ring Z bonded through X to a carbon atom to which both $W^1$ and $W^2$ are directly connected is not particularly limited. For example, when the ring Z represents a naphthalene ring, the group corresponding to the ring Z bonded to the carbon atom may be, for example, a 1-naphthyl group or a 2-naphthyl group.

In the general formulae (2) and (4), X independently represents a single bond or a group represented by —S—, typically a single bond.

In the general formulae (2) and (4), examples of R include single bonds; and alkylene groups having 1 to 4 carbon atoms such as methylene, ethylene, trimethylene, propylene, and butane-1,2-diyl groups. Single bonds and $C_{2-4}$ alkylene groups (particularly $C_{2-3}$ alkylene groups such as ethylene and propylene groups) are preferred, and a single bond is more preferred. When both $W^1$ and $W^2$ represent a group represented by the general formula (2), or when one of $W^1$ and $W^2$ represents a group represented by the general formula (2) while the other represents a group represented by the general formula (4), $R^1$ contained in $W^1$ may be the same as or different from $R^1$ contained in $W^2$.

In the general formulae (2) and (4), examples of $R^2$ include monovalent hydrocarbon groups such as alkyl groups (for example, $C_{1-12}$ alkyl groups, preferably $C_{1-8}$ alkyl groups, more preferably $C_{1-6}$ alkyl groups such as methyl, ethyl, propyl, isopropyl, and butyl groups), cycloalkyl groups (for example, $C_{5-10}$ cycloalkyl groups, preferably $C_{5-8}$ cycloalkyl groups, more preferably $C_{5-6}$ cycloalkyl groups such as cyclohexyl groups), aryl groups (for example, $C_{6-14}$ aryl groups, preferably $C_{6-10}$ aryl groups, more preferably $C_{6-8}$ aryl groups such as phenyl, tolyl, xylyl, and naphthyl groups), and aralkyl groups (for example, $C_{6-10}$ aryl-$C_{1-4}$ alkyl groups such as benzyl and phenethyl groups); hydroxyl groups; groups represented by —$OR^{4a}$ wherein $R^{4a}$ represents a monovalent hydrocarbon group (for example, the above-exemplified monovalent hydrocarbon group) such as alkoxy groups (for example, $C_{1-12}$ alkoxy groups, preferably $C_{1-8}$ alkoxy groups, more preferably $C_{1-6}$ alkoxy groups such as methoxy, ethoxy, propoxy, and butoxy groups), cycloalkoxy groups ($C_{5-10}$ cycloalkoxy groups such as cyclohexyloxy groups), aryloxy groups ($C_{6-10}$ aryloxy groups such as phenoxy group), and aralkyloxy groups (for example, $C_{6-10}$ aryl-$C_{1-4}$ alkyloxy groups such as benzyloxy groups); groups represented by —$SR^{4b}$ wherein $R^{4b}$ represents a monovalent hydrocarbon group (for example, the above-exemplified monovalent hydrocarbon group) such as alkylthio groups (for example, $C_{1-12}$ alkylthio groups, preferably $C_{1-8}$ alkylthio groups, more preferably $C_{1-6}$ alkylthio groups such as methylthio, ethylthio, propylthio, and butylthio groups), cycloalkylthio groups (for example, $C_{5-10}$ cycloalkylthio groups such as cyclohexylthio groups), aryl thio groups ($C_{6-10}$ aryl thio groups such as phenylthio groups), and aralkyl thio groups (for example, $C_{6-10}$ aryl-$C_{1-4}$ alkylthio groups such as benzylthio groups); acyl groups ($C_{1-6}$ acyl groups such as acetyl groups); alkoxycarbonyl groups (for example, $C_{1-4}$ alkoxycarbonyl groups such as methoxycarbonyl group); halogen atoms (for example, a fluorine atom, a chlorine atom, a bromine atom, and an iodine atom); nitro groups; cyano groups; mercapto groups; carboxyl groups; amino groups; carbamoyl groups; groups represented by —$NHR^{4c}$ wherein $R^{4c}$ represents a monovalent hydrocarbon group (for example, the above-exemplified monovalent hydrocarbon group) such as alkylamino groups ($C_{1-12}$ alkylamino groups, preferably $C_{1-8}$ alkylamino groups, more preferably $C_{1-6}$ alkylamino groups such as methylamino groups, ethylamino groups, propylamino groups, and butylamino groups), cycloalkylamino groups (for example, $C_{5-10}$ cycloalkylamino groups such as cyclohexylamino groups), arylamino groups ($C_{6-10}$ aryl amino groups such as phenylamino groups), and aralkyl amino groups (for example, $C_{6-10}$ aryl-$C_{1-4}$ alkylamino groups such as benzylamino groups); groups represented by —$N(R^{4d})_2$ wherein each $R^{4d}$ independently represents a monovalent hydrocarbon group (for example, the above-exemplified monovalent hydrocarbon group) such as dialkylamino groups (di($C_{1-12}$ alkyl)amino groups, preferably di($C_{1-8}$ alkyl)amino groups, more preferably di($C_{1-6}$ alkyl)amino groups such as dimethylamino groups, diethylamino groups, dipropylamino groups, and dibutylamino groups), dicycloalkylamino groups (di($C_{5-10}$ cycloalkyl)amino groups such as dicyclohexylamino groups), diaryl amino groups (di($C_{6-10}$ aryl)amino groups such as diphenylamino groups), and diaralkyl amino groups (for example, di($C_{6-10}$ aryl $C_{1-4}$ alkyl)amino groups such as dibenzylamino groups); (meth)acryloyloxy groups; sulfo groups; and the above monovalent hydrocarbon groups, groups represented by —$OR^{4a}$, groups represented by —$SR^{4b}$, acyl groups, alkoxycarbonyl groups, groups represented by —$NHR^{4c}$, or groups obtained by substituting at least a part of hydrogen atoms bonded to carbon atoms contained in groups represented by —$N(R^{4d})_2$ with the above monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group [for example, alkoxyaryl groups (for example, $C_{1-4}$ alkoxy $C_{6-10}$ aryl groups such as methoxyphenyl groups), alkoxycarbonylaryl groups (for example, $C_{1-4}$ alkoxycarbonyl $C_{6-10}$ aryl groups such as methoxycarbonylphenyl groups and ethoxycarbonylphenyl groups)].

Among them, typical examples of $R^2$ include monovalent hydrocarbon groups, groups represented by —$OR^{4a}$, groups represented by —$SR^{4b}$, acyl groups, alkoxycarbonyl groups, halogen atoms, nitro group, cyano groups, groups represented by —NHR$^{4c}$, and groups represented by —N(R$^{4d}$)$_2$.

Examples of preferred R$^2$ include monovalent hydrocarbon groups [for example, alkyl groups (for example, C$_{1-6}$ alkyl groups), cycloalkyl groups (for example, C$_{5-8}$ cycloalkyl groups), aryl groups (for example, C$_{6-10}$ aryl groups), and aralkyl groups (for example, C$_{6-8}$ aryl-C$_{1-2}$ alkyl groups)], and alkoxy groups (for example, C$_{1-4}$ alkoxy groups). In particular, preferably, R$^{2a}$ and R$^{2b}$ represent a monovalent hydrocarbon group such as an alkyl group [for example, a C$_{1-4}$ alkyl group (particularly a methyl group)], an aryl group [for example, a C$_{6-10}$ aryl group (particularly a phenyl group)](particularly an alkyl group).

When m is an integer of 2 or more, R$^2$s may be different from or the same as each other. When both W$^1$ and W$^2$ represent a group represented by the general formula (2), or when one of W$^1$ and W$^2$ represents a group represented by the general formula (2) while the other represents a group represented by the general formula (4), R$^2$ contained in W$^1$ may be the same as or different from R$^2$ contained in W$^2$.

In the general formulae (2) and (4), the number of R$^2$s, that is m, may be selected according to the type of the ring Z and may be, for example, 0 to 4, preferably 0 to 3, more preferably 0 to 2. When both W$^1$ and W$^2$ represent a group represented by the general formula (2), or when one of W$^1$ and W$^2$ represents a group represented by the general formula (2) while the other represents a group represented by the general formula (4), m in W$^1$ may be the same as or different from m in W.

In the general formula (1), examples of the ring Y$^1$ and the ring Y$^2$ include benzene rings and fused polycyclic aromatic hydrocarbon rings [for example, fused di- to tetracyclic aromatic hydrocarbon rings such as fused dicyclic hydrocarbon rings (for example, C$_{8-20}$ fused dicyclic hydrocarbon rings, preferably C$_{10-16}$ fused dicyclic hydrocarbon rings such as naphthalene rings, and fused tricyclic aromatic hydrocarbon rings (for example, anthracene rings and phenanthrene rings)]. The ring Y$^1$ and the ring Y$^2$ are preferably a benzene ring or a naphthalene ring. The ring Y$^1$ and the ring Y$^2$ may be the same as or different from each other. For example, one of the rings may represent a benzene ring with the other ring representing a naphthalene ring or the like.

In the general formula (1), R represents a single bond, an optionally substituted methylene group, an ethylene group that is optionally substituted and may contain a hetero atom between two carbon atoms, a group represented by —O—, a group represented by —NH—, or a group represented by —S—, and is typically a single bond. Here, examples of substituents include a cyano group, halogen atoms (such as fluorine, chlorine, and bromine atoms), monovalent hydrocarbon groups [for example, alkyl groups (C$_{1-6}$ alkyl groups such as methyl, ethyl, propyl, isopropyl, butyl, and t-butyl groups), and aryl groups (C$_{6-10}$ aryl groups such as phenyl groups)]. Examples of hetero atoms include an oxygen atom, a nitrogen atom, a sulfur atom, or a silicon atom.

In the general formula (1), general examples of R$^{3a}$ and R$^{3b}$ include nonreactive substituents, for example, cyano groups, halogen atoms (for example, fluorine, chlorine, and bromine atoms), monovalent hydrocarbon groups [for example, alkyl groups and aryl groups (C$_{6-10}$ aryl groups such as phenyl groups)]. A cyano group or an alkyl group is preferred, and an alkyl group is particularly preferred. Examples of alkyl groups include C$_{1-6}$ alkyl groups (for example, C$_{1-4}$ alkyl groups, particularly methyl groups) such as methyl, ethyl, propyl, isopropyl, butyl, and t-butyl groups.

When n1 is an integer of 2 or more, R$^{3a}$ may be the same as or different from each other. When n2 is an integer of 2 or more, R$^{3b}$s may be the same as or different from each other. Further, R$^{3a}$ and R$^{3b}$ may be the same as or different from each other. The position of bonding of R$^{3a}$ and R$^{3b}$ to the the ring Y$^1$ and the ring Y$^2$ (position of substitution) is not particularly limited. The number of substituents n1 and n2 is preferably 0 (zero) or 1, particularly preferably 0 (zero). n1 and n2 may be the same as or different from each other.

Compounds represented by the general formula (1) maintain excellent optical properties and thermal properties and, at the same time, have high reactivity by virtue of the presence of a vinyloxy group and/or a (meth)acryloyloxy group. In particular, when the ring Y$^1$ and the ring Y$^2$ represent a benzene ring with R representing a single bond, compounds represented by the general formula (1) have a fluorene skeleton and thus possess further improved optical properties and thermal properties. The compounds represented by the general formula (1) can be polymerized and thus function as polymerizable monomers. In particular, when both W$^1$ and W$^2$ represent a group represented by the general formula (2), the compounds represented by the general formula (1) can be cationically polymerized and thus can function as cationically polymerizable monomers. On the other hand, when both W$^1$ and W$^2$ represent a (meth)acryloyloxy group, the compounds represented by the general formula (1) can be radically polymerized and thus function as radically polymerizable monomers. In the compounds represented by the general formula (1), when W$^1$ and W$^2$ each independently represent a group represented by the general formula (2) or a (meth)acryloyloxy group, two vinyl groups contained in the form of the vinyloxy group and/or the (meth)acryloyloxy group can be reacted with different molecules and, thus, the compounds represented by the general formula (1) are suitable as crosslinking agents. Further, the compounds represented by the general formula (1) can provide cured products having a high hardness and are preferred as a base component in the composition. In addition, when compounds represented by the general formula (1) are contained in negative-type photosensitive resin compositions, good micropatterning properties can be obtained. Compounds represented by the general formula (1) can be used in various applications, for example, alignment films and flattening films (alignment films and flattening films used, for example, in liquid crystal displays and organic EL displays; resist underlying films such as antireflection films, interlayer insulating films, and carbon hard masks; spacers and partition walls such as liquid crystal displays and organic EL displays; pixels and black matrixes in color filters of liquid crystal displays; display devices such as liquid crystal displays and organic EL displays; lenses (for example, microlenses), optical members such as optical fibers, light waveguides, prism sheets, holograms, high refractive index films, and retroreflection films; low moisture permeable membranes (for example, low moisture permeable membranes used as water vapor barrier layers; optical materials; and semiconductor materials.

Among the compounds represented by the general formula (1), particularly preferred examples thereof include compounds represented by the following formulae.

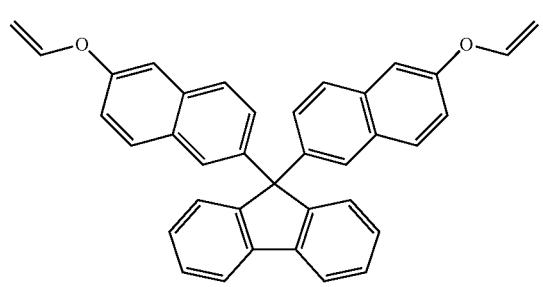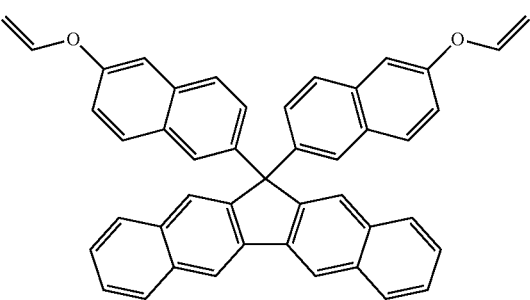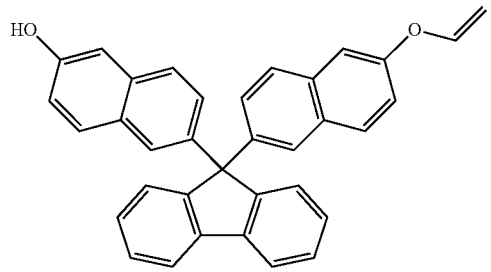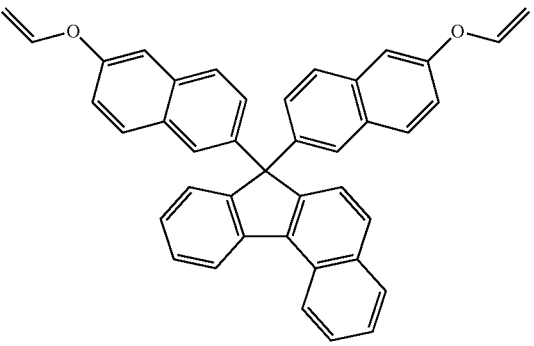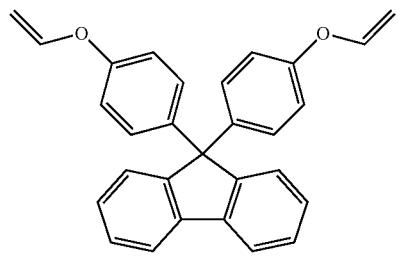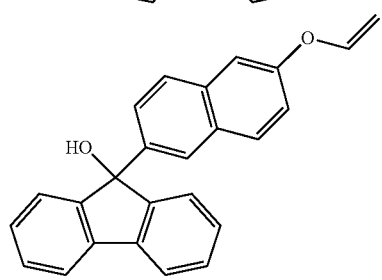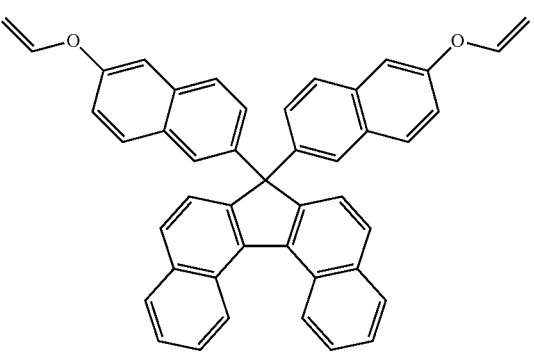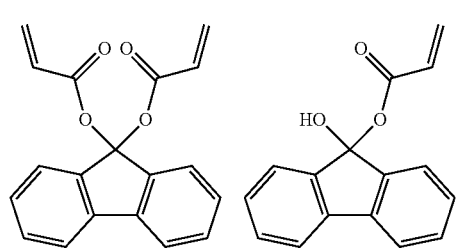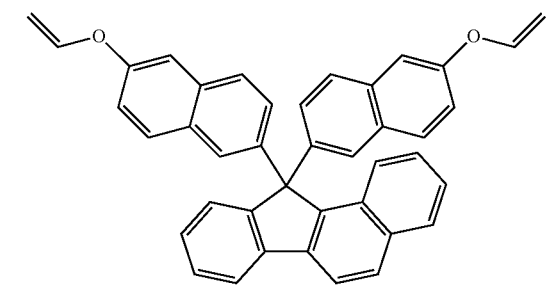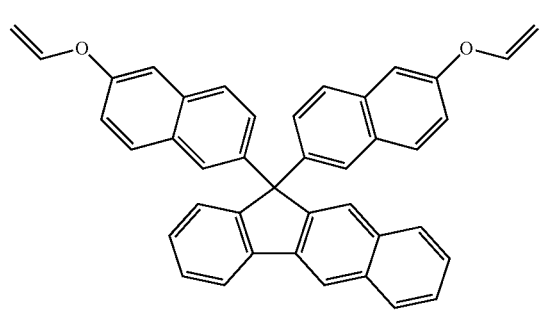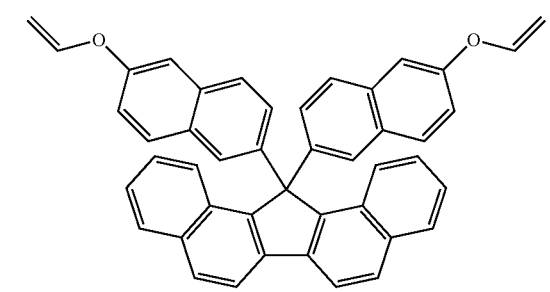

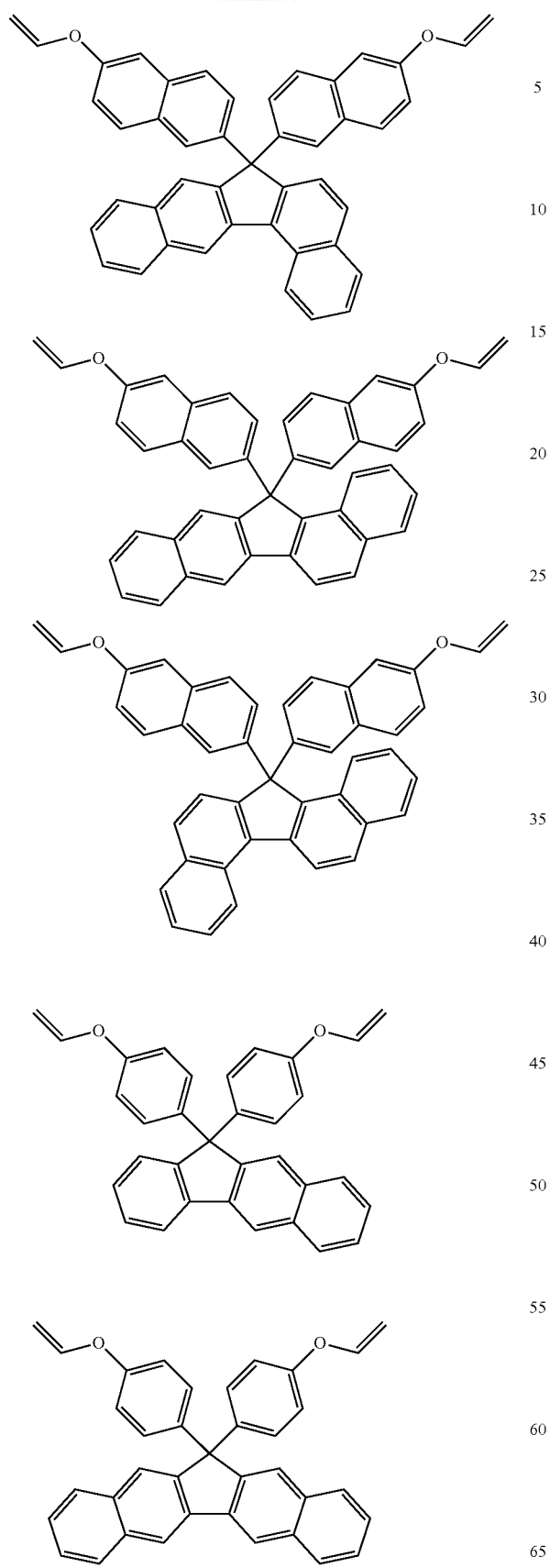

-continued

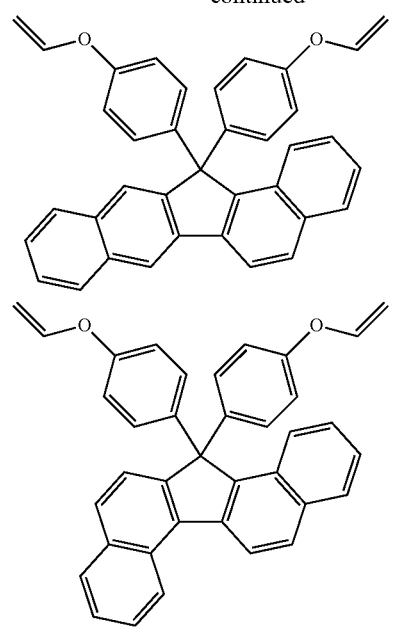

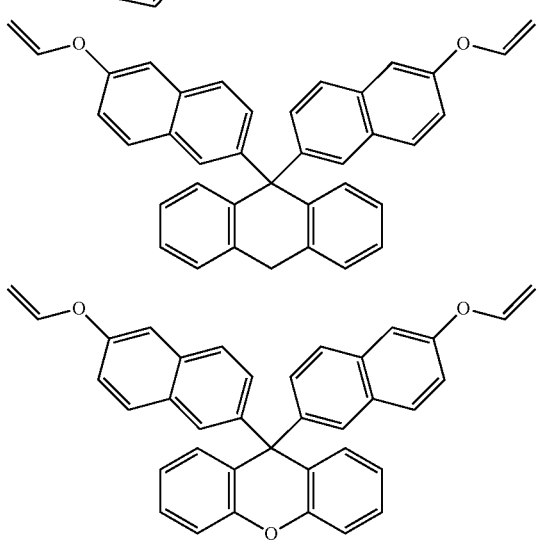

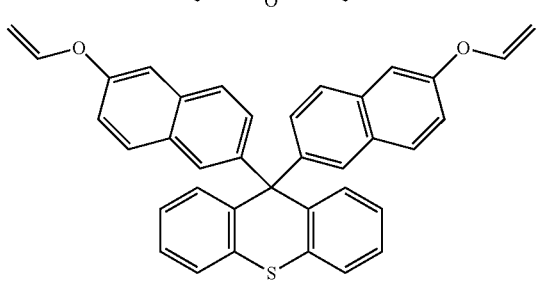

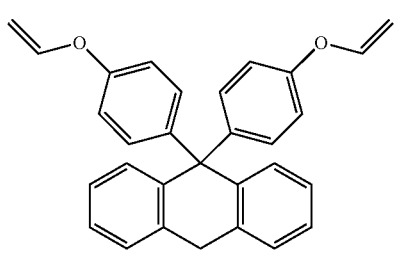

-continued

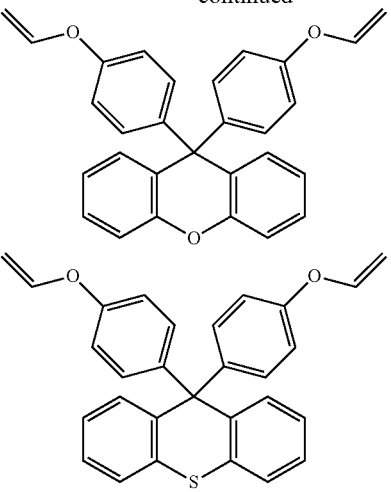

The content of the compound represented by the formula (1) is preferably 1 to 100% by mass, more preferably 3 to 80% by mass, still more preferably 5 to 50% by mass relative to the solid content of the composition according to the present invention. When the content of the compound represented by the formula (1) is in the above-defined range, an improvement in coating film forming capability and curability can easily be achieved, for example.

[Method for Producing Vinyl-Group-Containing Compounds Represented by General Formula (1a)]

Among the vinyl-group-containing compounds represented by the general formula (1), compounds represented by the following general formula (1a) can be produced by the following production methods 1 to 3.

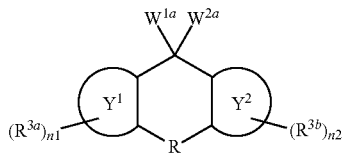

(1a)

(wherein $W^{1a}$ and $W^{2a}$ each independently represent a group represented by the general formula (2), a group represented by the general formula (4), a hydroxyl group, or a (meth)acryloyloxy group, provided that $W^{1a}$ and $W^{2a}$ do not simultaneously represent a hydroxyl group or a (meth)acryloyloxy group; and a ring $Y^1$, a ring $Y^2$, R, $R^{3a}$, $R^{3b}$, n1, and n2 are as defined above.)

Production Method 1

Vinyl-group-containing compounds represented by the general formula (1a) can be synthesized, for example, according to a production method described in JP2008-266169A by reacting a vinyl ester compound represented by the following general formula (13) with a hydroxyl group-containing compound represented by the following general formula (3) in the presence of a transition element compound catalyst and an inorganic base. The inorganic base is preferably a solid inorganic base containing not less than 10% by weight of particles having a diameter of less than 150 μm. Specifically, vinyl-group-containing compounds represented by the general formula (1a) can be synthesized as described in Synthesis Examples 1 to 3 that will be described later.

(wherein $R^6$ represents a hydrogen atom or an organic group.)

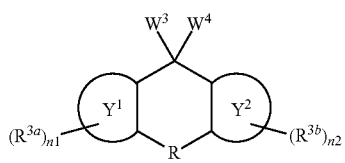

(wherein $W^3$ and $W^4$ each independently represent a group represented by the following general formula (4) or a hydroxyl group, provided that $W^3$ and $W^4$ do not simultaneously represent a hydroxyl group; and a ring $Y^1$, a ring $Y^2$, R, $R^{3a}$, $R^{3b}$, n1, and n2 are as defined above.)

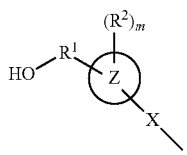

(wherein a ring Z, X, $R^1$, $R^2$, and m are as defined above.)

Compounds represented by the general formula (3) can be synthesized, for example, by reacting a compound represented by the following general formula (14) and/or a compound represented by the following general formula (15) with a compound represented by the following general formula (16) in the presence of an acid catalyst. Desired hydroxyl group-containing compounds represented by the general formula (3) can be obtained by properly regulating a combination of compounds represented by the general formula (14) and compounds represented by the general formula (15) and the addition amounts of the compounds. After the reaction, the intended hydroxyl group-containing compounds may be separated by publicly known separation methods, for example, silica gel column chromatography.

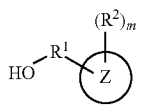

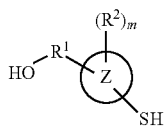

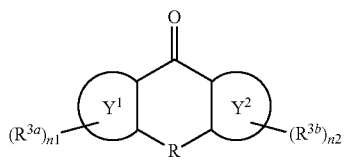

(wherein, in the general formulae (14), (15), and (16), a ring $Y^1$, a ring $Y^2$, a ring Z, R, $R^1$, $R^2$, $R^{3a}$, $R^{3b}$, m, n1, and n2 are as defined above.)

Acid catalysts usable in the synthesis of compounds represented by the general formula (3), reaction conditions and the like may be those that are described in Patent Document 1 or JP2002-255929A to the effect that are used in the production method of fluorene-based compounds described in the claims.

Production Method 2

Compounds represented by the general formula (1a) can also be synthesized by a production method that includes obtaining vinyl-group-containing compounds represented by the general formula (1a) from hydroxyl group-containing compounds represented by the general formula (3) through leaving group-containing compounds represented by the general formula (5).

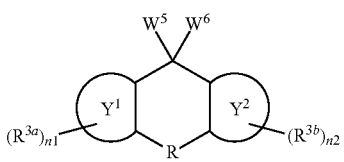

(wherein $W^5$ and $W^6$ each independently represent a group represented by the general formula (6) or a hydroxyl group, provided that $W^5$ and $W^6$ do not simultaneously represent a hydroxyl group; and a ring $Y^1$, a ring $Y^2$, R, $R^{3a}$, $R^{3b}$, n1, and n2 are as defined above.)

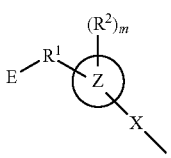

(wherein E represents an alkyloxy group having 1 to 4 carbon atoms substituted by a chlorine atom, a bromine atom, an iodine atom, a methanesulfonyloxy group, a trifluoromethanesulfonyloxy group, a p-toluenesulfonyloxy group, or a benzenesulfonyloxy group; and a ring Z, X, $R^1$, $R^2$, and m are as defined above.)

Leaving group-containing compounds represented by the general formula (5) can be synthesized, for example, by reacting hydroxyl group-containing compounds represented by the general formula (3) with leaving group-containing compounds. Leaving group-containing compounds include, for example, thionyl chloride, and compounds represented by the following formula. The temperature of the reaction may be, for example, −20 to 150° C., preferably −10 to 140° C., more preferably 30 to 130° C.

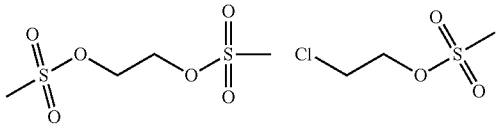

Vinyl-group-containing compounds represented by the general formula (1a) can be synthesized, for example, by reacting leaving group-containing compounds represented by the general formula (5) with vinylating agents. Vinylating agents include, for example, sodium hydroxide, triethylamine, diisopropyl ethylamine, 1,4-diazabicyclo[2.2.2]octane, diazabicyclo undecene, sodium methoxide, sodium ethoxide, sodium ethoxide, and potassium t-butoxide. Preferred are diazabicyclo undecene, sodium ethoxide, and potassium t-butoxide. More preferred is potassium t-butoxide. The temperature of the reaction is, for example, −20 to 150° C., preferably −10 to 100° C., more preferably 0 to 60° C.

Production Method 3

Compounds represented by the general formula (1a) can also be synthesized, for example, by a production method that includes obtaining vinyl-group-containing compounds represented by the general formula (1a) from hydroxyalkyloxy group-containing compounds represented by the general formula (7) through leaving group-containing compounds represented by the general formula (5). Specifically, compounds represented by the general formula (1a) can be synthesized as described in Synthesis Examples 4 and 5 and Synthesis Examples 12 and 13 to be described later.

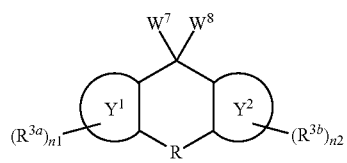
(7)

(wherein W$^7$ and W$^8$ each independently represent a group represented by the general formula (8) or a hydroxyl group, provided that W$^7$ and W$^8$ do not simultaneously represent a hydroxyl group; and a ring Y$^1$, a ring Y$^2$, R, R$^{3a}$, R$^{3b}$, n1, and n2 are as defined above.)

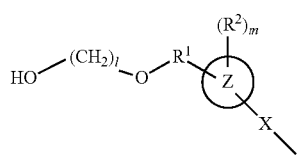
(8)

(wherein l represents an integer of 1 to 4; and a ring Z, X, R$^1$, R$^2$, and m are as defined above.)

Hydroxyalkyloxy group-containing compounds represented by the general formula (7) can be synthesized, for example, by reacting compounds represented by the following general formula (17) and/or compounds represented by the following general formula (18) with compounds represented by the general formula (16) in the presence of an acid catalyst. Desired hydroxyalkyloxy group-containing compounds represented by the general formula (7) can be obtained by properly regulating a combination of compounds represented by the following general formula (17) and compounds represented by the following general formula (18) and the addition amounts of the compounds. After the reaction, the intended hydroxyalkyloxy group-containing compounds may be separated, for example, by publicly known separation methods such as silica gel column chromatography. Acid catalysts, reaction conditions and the like usable in the synthesis of compounds represented by the general formula (7) may be, for example, those that are exemplified in the description of the synthesis method of compounds represented by the general formula (3).

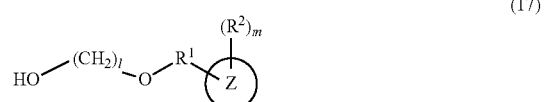
(17)

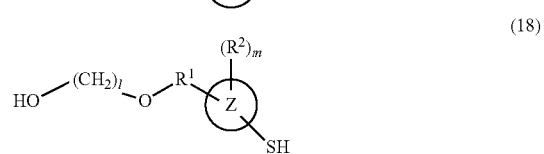
(18)

(wherein, in the general formulae (17) and (18), a ring Z, R$^1$, R$^2$, and m are as defined above.)

Leaving group-containing compounds represented by the general formula (5) can be synthesized, for example, by reacting hydroxy alkyloxy group-containing compounds represented by the general formula (7) with a leaving group-containing compound. The leaving group-containing compound and the reaction temperature may be those that are exemplified in the description of the production method 2.

Vinyl-group-containing compounds represented by the general formula (1a) can be synthesized, for example, by reacting leaving group-containing compounds represented by the general formula (5) with vinylating agents. The vinylating agent and the reaction temperature may be, for example, those that are exemplified in the production method 2.

According to a production method 3, compounds represented by the general formula (1a) can be obtained from hydroxyalkyloxy group-containing compounds represented by the general formula (7) at a high yield. For example, the yield of 9,9'-bis(6-vinyloxy-2-naphthyl)fluorene was 77% in Synthesis Examples 4 and 5, and the yield of 9,9'-bis(4-vinyloxyphenyl)fluorene was 79% in Synthesis Examples 12 and 13. According to the production method 3, the load in the step of purification of compounds represented by the general formula (1a) can be reduced. Further in the production method 3, the reaction can be carried out at ordinary pressure, and thus special reaction facilities such as heat-resistant vessels are unnecessary, making it possible to use simpler apparatuses. Further, in the production method 3, flammable gases such as acetylene gas are not used, and thus compounds represented by the general formula (1a) can be produced more safely.

Purification Method

Vinyl-group-containing compounds represented by the general formula (1) may be purified after the completion of the synthesis. The purification method is not particularly limited, and conventional methods such as silica gel column chromatography may be mentioned as the purification method. The purification can realize an improvement in purity of the vinyl-group-containing compound represented by the general formula (1) and a reduction in the content of the metallic component. The purified vinyl-group-containing compound has improved reactivity and effectively suppresses coloring during the reaction.

Leaving Group-Containing Compounds Represented by the General Formula (5)

Leaving group-containing compounds represented by the general formula (5) are useful as intermediates for the production of vinyl-group-containing compounds represented by the general formula (1a). Leaving group-containing compounds represented by the general formula (5) can be synthesized, for example, by methods described above in connection with the production method 2 or 3.

Monovinyl-Group-Containing Compounds Represented by the General Formula (9) and Production Method Thereof Monovinyl-group-containing compounds represented by the following general formula (9) are useful as intermediates for the production of vinyl-group-containing compounds represented by the general formula (1a).

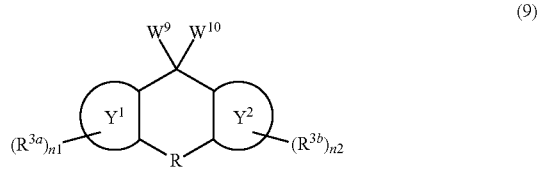

(9)

(wherein any one of $W^9$ and $W^{10}$ represents a group represented by the general formula (2) while the other represents a group represented by the general formula (6); and a ring $Y^1$, a ring $Y^2$, R, $R^{3a}$, $R^{3b}$, n1, and n2 are as defined above.)

Monovinyl-group-containing compounds represented by the general formula (9) can be synthesized by a production method that includes obtaining monovinyl-group-containing compounds represented by the general formula (9) from leaving group-containing compounds represented by the following general formula (5a). Specifically, monovinyl-group-containing compounds represented by the general formula (9) can be synthesized as described in Synthesis Examples 8 and 11 that will be described later. That is, monovinyl-group-containing compounds represented by the general formula (9) can be synthesized, for example, by reacting leaving group-containing compounds represented by the general formula (5a) with vinylating agents. The vinylating agent and the reaction temperature may be, for example, those that are exemplified in the production method 2. The amount of the vinylating agent used is preferably 0.1 to 10 moles, more preferably 0.5 to 5 moles, still more preferably 0.8 to 2 moles per mole of the leaving group in the leaving group-containing compound represented by the general formula (5a).

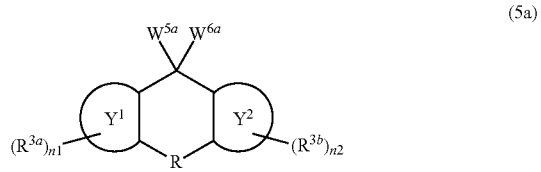

(5a)

(wherein W and $W^{6a}$ represent a group represented by the general formula (6); and a ring $Y^1$, a ring $Y^2$, R, $R^{3a}$, $R^{3b}$, n1, and n2 are as defined above.)

Monovinyl-Group- and mono(meth)acryloyloxy-Group-Containing Compounds Represented by General Formula (10)

Monovinyl-group- and mono(meth)acryloyloxy-group-containing compounds contained in the composition according to the present invention are represented by the following general formula (10). The monovinyl-group- and mono (meth)acryloyloxy-group-containing compounds may be used solely or in a combination of two or more thereof. This compound has high reactivity by virtue of the presence of the vinyloxy group and the (meth)acryloyloxy group while maintaining excellent optical properties and thermal properties. In particular, when the ring $Y^1$ and the ring $Y^2$ represent a benzene ring with R representing a single bond, compounds represented by the following general formula (10) have a fluorene skeleton and have further improved optical properties and thermal properties. As with vinyl-group-containing compounds represented by the general formula (1), compounds represented by the following general formula (10) can be polymerized and thus function as polymerizable monomers and, further, are suitable for use as crosslinking agents. Further, compounds represented by the general formula (10) can provide cured products having a high hardness and thus are preferred as a base component in the composition. In addition, when compounds represented by the general formula (10) are incorporated in negative-type photosensitive resin compositions, good micropatterning properties can be obtained. Compounds represented by the following general formula (10) can be used in various applications, for example, in applications specifically exemplified for compounds represented by the general formula (1).

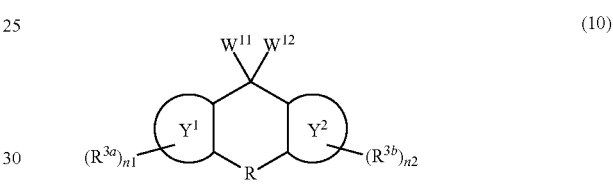

(10)

(wherein any one of $W^{11}$ and $W^{12}$ represents a group represented by the general formula (2) while the other represents a group represented by the following general formula (11) or (12); a ring $Y^1$, a ring $Y^2$, R, $R^{3a}$, $R^{3b}$, n1, and n2 are as defined above.)

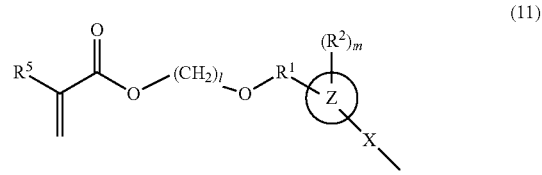

(11)

(wherein $R^5$ represents a hydrogen atom or a methyl group; a ring Z, X, $R^1$, $R^2$, m, and l are as defined above.)

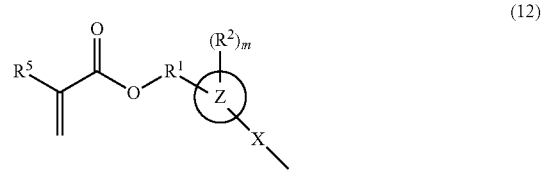

(12)

(wherein a ring Z, X, $R^1$, $R^2$, $R^5$, and m are as defined above.)

The content of the compound represented by the formula (10) is preferably 1 to 100% by mass, more preferably 3 to 80% by mass, still more preferably 5 to 50% by mass relative to the solid content of the composition according to the present invention. When the content of the compound represented by the formula (10) is in the above-defined range, an improvement in coating film forming capability and curability can easily be achieved, for example.

(Meth)acryloyloxy-Group-Containing Compounds Represented by the General Formula (19)

(Meth)acryloyloxy-group-containing compounds contained in the composition according to the present invention are represented by the following general formula (19). The (meth)acryloyloxy-group-containing compound may be used solely or in a combination of two or more thereof. This compound has high reactivity by virtue of the presence of the (meth)acryloyloxy group while maintaining excellent optical properties and thermal properties. In particular, when the ring $Y^1$ and the ring $Y^2$ represent a benzene ring with R representing a single bond, compounds represented by the following general formula (19) have a fluorene skeleton and thus possess further improved optical properties and thermal properties. As with vinyl-group-containing compounds represented by the general formula (1), compounds represented by the following general formula (19) can be polymerized and thus function as polymerizable monomers and, further, are suitable for use as crosslinking agents. Further, compounds represented by the general formula (19) can provide cured products having a high hardness and thus are preferred as a base component in the composition. In addition, when compounds represented by the general formula (19) are incorporated in negative-type photosensitive resin compositions, good micropatterning properties can be obtained. Compounds represented by the general formula (19) can be used in various applications, for example, in applications specifically exemplified for compounds represented by the general formula (1).

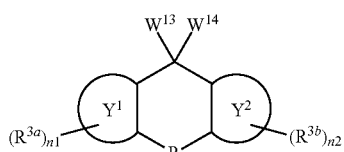
(19)

(wherein $W^{13}$ and $W^{14}$ each independently represent a group represented by the general formula (12), a hydroxyl group, or a (meth)acryloyloxy group, provided that at least one of $W^{13}$ and $W^{14}$ represents a group represented by the general formula (12); and a ring $Y^1$, a ring $Y^2$, R, $R^{3a}$, $R^{3b}$, n1, and n2 are as defined above.)

Among compounds represented by the general formula (19), specific examples of particularly preferred compounds include compounds represented by the following formulae.

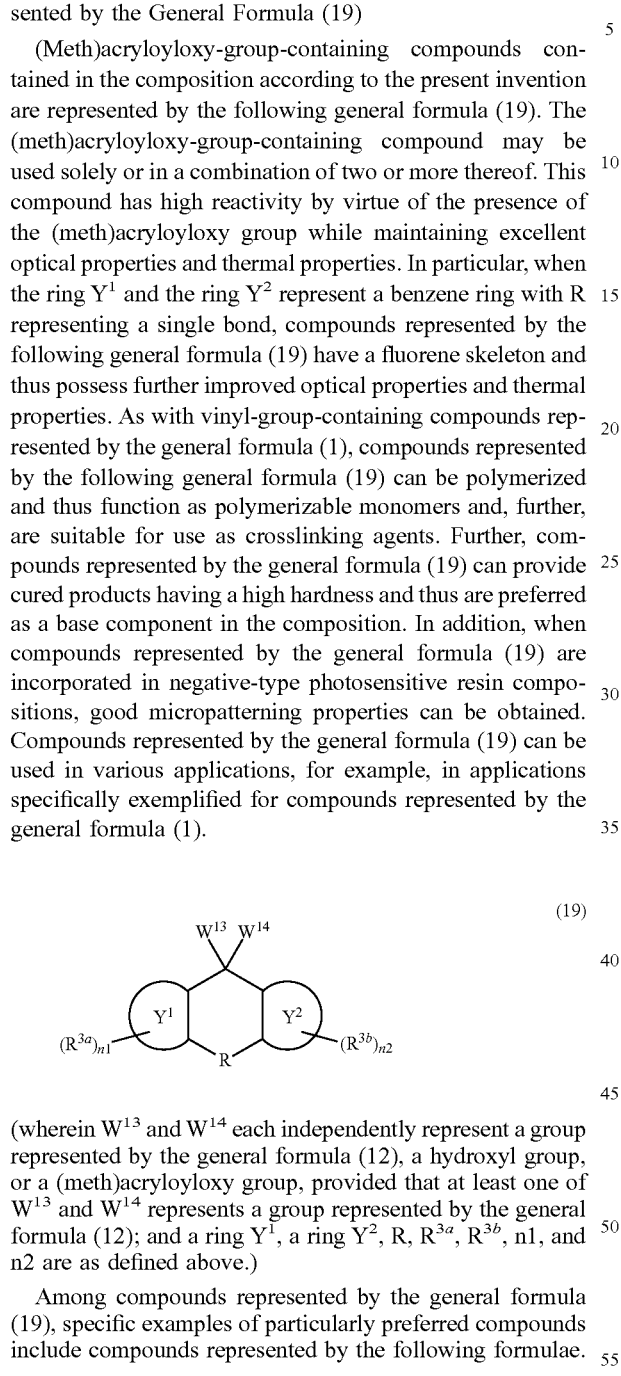

23
-continued
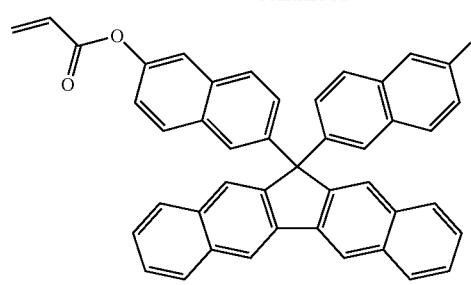
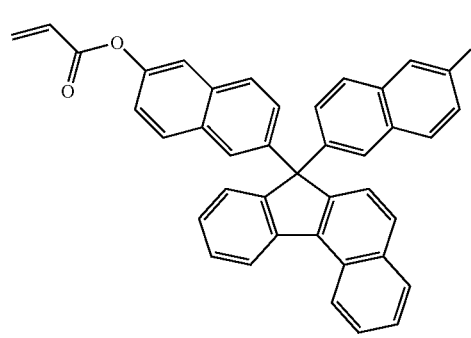
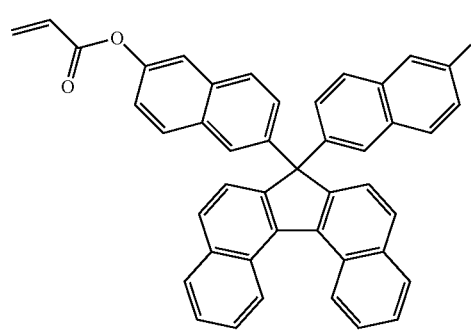
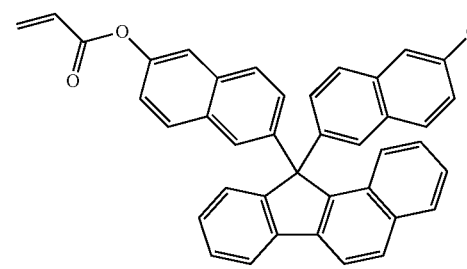
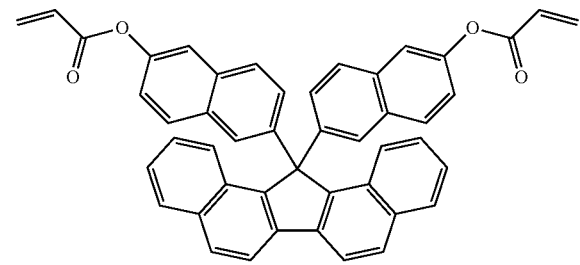
24
-continued
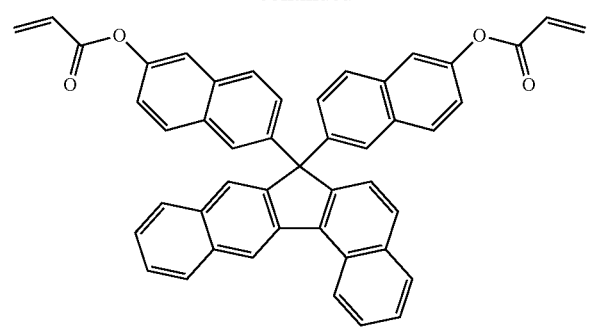
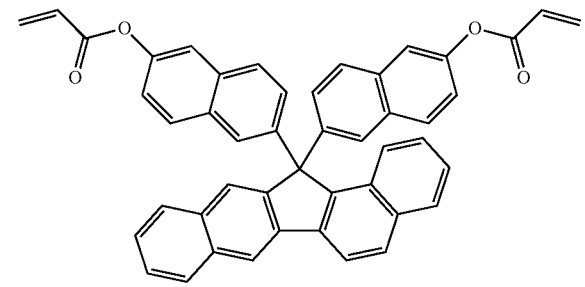
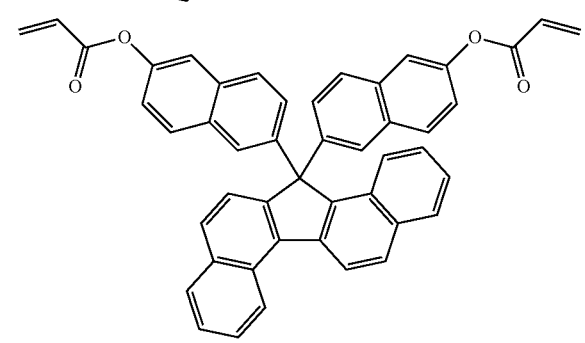
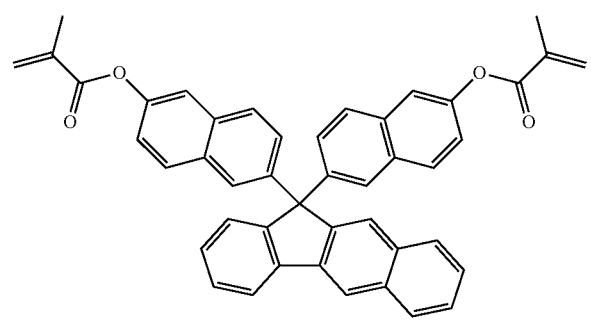
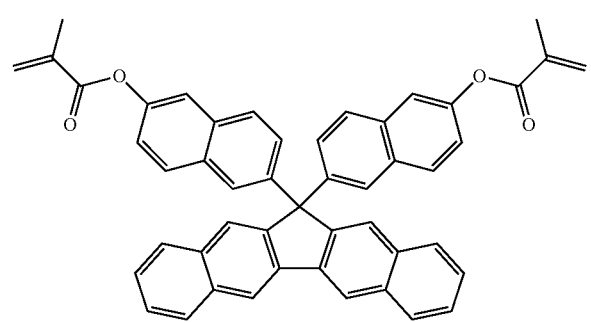

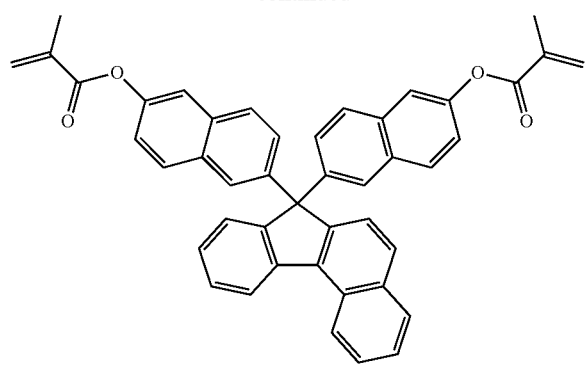

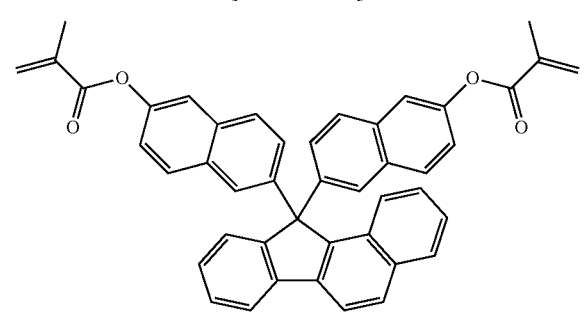

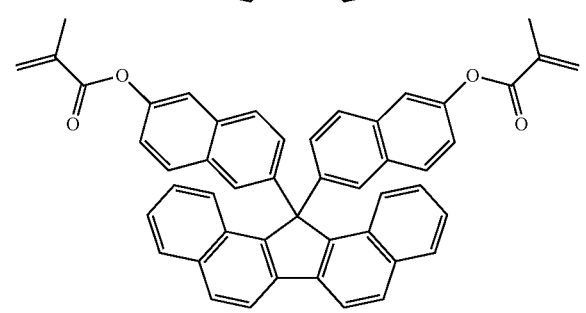

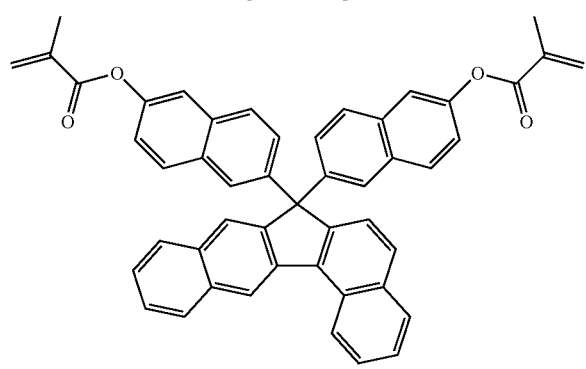

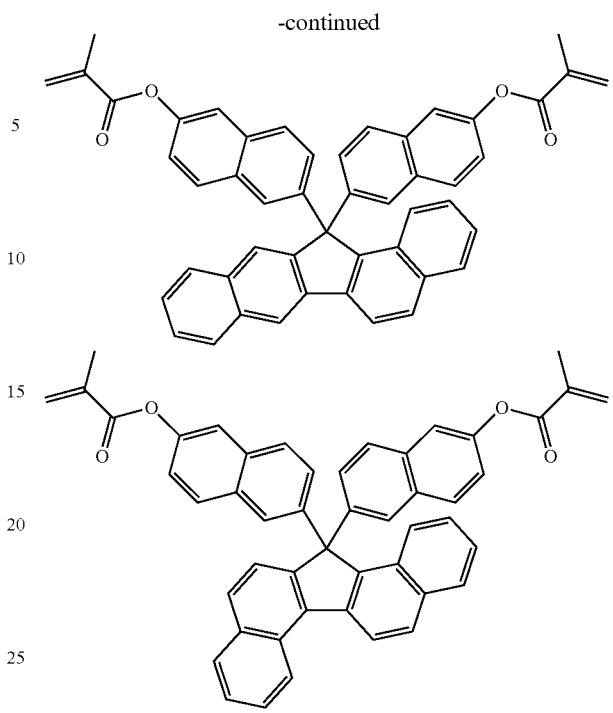

The content of the compound represented by the formula (19) is preferably 1 to 100% by mass, more preferably 3 to 80% by mass, still more preferably 5 to 50% by mass relative to the solid content of the composition according to the present invention. When the content of the compound represented by the formula (19) is in the above-defined range, an improvement in coating film forming capability and curability can easily be achieved, for example.

[Production Method of (Meth)acryloyloxy Group-Containing Compounds Represented by General Formula (19)]

Compounds represented by the general formula (19) can be synthesized, for example, by a production method that includes obtaining a (meth)acryloyloxy group-containing compound represented by the general formula (19) from hydroxyl group-containing compounds represented by the general formula (3). Specifically, compounds represented by the general formula (19) can be synthesized as described in Synthesis Examples 14 and 15 that will be described later.

Compounds represented by the general formula (19) can be synthesized, for example, by reacting hydroxyl group-containing compounds represented by the general formula (3) with (meth)acrylating agents. Examples of (meth)acrylating agents include (meth)acryloyl halides such as (meth)acryloyl chlorides; and (meth)acrylic anhydrides. Preferred are (meth)acryloyl halides. More preferred are (meth)acryloyl chlorides. The reaction temperature may be, for example, −20 to 150° C., preferably −10 to 100° C., more preferably 0 to 60° C. The term "(meth)acrylating agent" as used herein refers to both acrylating agents and methacrylating agents, and the term "(meth)acrylic anhydride" refers to both acrylic anhydride and methacrylic anhydride.

Compounds represented by the general formula (19) may be purified after the completion of the synthesis. The purification method is not particularly limited, and conventional methods such as silica gel column chromatography may be mentioned as the purification method. The purification can realize an improvement in purity of the compound represented by the general formula (19) and a reduction in the content of the metallic component. The purified compound has improved reactivity and effectively suppresses coloring during the reaction.

Base ingredients other than vinyl-group-containing compounds represented by the general formula (1), monovinyl-group- and mono(meth)acryloyloxy-group-containing compounds represented by the general formula (10), and (meth) acryloyloxy-group-containing compounds represented by the general formula (19)

The composition according to the present invention may further contain base ingredients other than the compounds represented by the general formula (1), the compounds represented by the general formula (10) and the compound represented by the general formula (19) (hereinafter referred to simply as "base ingredients"). The base ingredients, together with the compound represented by the general formula (1), the compound represented by the general formula (10) and/or the compound represented by the general formula (19), can form cured products and the like. For example, at least one compound or resin selected from the group consisting of addition-polymerizable compounds, addition-condensable compounds, and condensation-polymerizable compounds may be mentioned as the base ingredient. The base ingredient may be used solely or in a combination of two or more thereof.

[Addition-Polymerizable Compounds, Addition-Condensable Compounds and/or Condensation-Polymerizable Compounds]

Examples of addition-polymerizable compounds include compounds having an ethylenically unsaturated bond. Examples of compounds having an ethylenically unsaturated bond include monofunctional monomers and polyfunctional monomers exemplified as photopolymerizable monomers in the composition of the first embodiment that will be described later, and vinyl-group-containing compounds other than compounds represented by the general formula (1), compounds represented by the general formula (10), and compounds represented by the general formula (19).

Addition-condensable compounds include phenols, aldehydes, and epichlorohydrin. Addition condensation occurs between phenols and aldehydes and between phenols, particularly bisphenols, and epichlorohydrin. Phenols and aldehydes may be those exemplified in the composition according to the second embodiment that will be described later.

Condensation-polymerizable compounds include, for example, acid dianhydrides and diamines, and condensation polymerization occurs between acid dianhydride and diamine. Acid dianhydrides and diamines include those exemplified in the composition of the third or fourth embodiment that will be described later.

The content of at least one compound selected from the group consisting of addition-polymerizable compounds, addition-condensable compounds, and condensation-polymerizable compounds is preferably 0 to 99% by mass, more preferably 5 to 80% by mass, and further preferably 10 to 50% by mass relative to the solid content of the composition according to the present invention. When the content of the at least one compound is in the above-defined range, an improvement in coating film forming capability can easily be achieved, for example.

[Resins]

Resins include, for example, resins having a cardo structure, resins having a phenolic hydroxyl group, polyimide precursors, polyimide resins, acrylic resins, and epoxy resins. Alkali-soluble resins are preferred as the resin. Specific examples of resins include those exemplified in the description of the compositions of the first to sixth embodiments that will be described later.

The term "alkali-soluble resin" as used herein refers to one that, when a resin film having a thickness of 1 μm is formed on a substrate with a resin solution having a resin concentration of 20% by mass (solvent: propylene glycol monomethyl ether acetate) and is then immersed in a 2.38% (by mass) aqueous tetramethylammonium hydroxide (TMAH) solution for one min, not less than 0.01 μm thickness of the resin film is dissolved in the aqueous solution.

The content of the resin is preferably 0 to 99% by mass, more preferably 5 to 80% by mass, and further preferably 15 to 50% by mass relative to the solid content of the composition according to the present invention. When the content of the resin is in the above-defined range, an improvement in coating film forming capability can easily be achieved, for example.

Organic Solvent

The composition according to the present invention may further contain an organic solvent. Examples of organic solvents include those exemplified in the composition of the first embodiment that will be described later. The organic solvent may be used solely or in a combination of two or more thereof.

The content of the organic solvent is such that the solid content concentration of the composition according to the present invention is preferably 0.5 to 70% by mass, more preferably 1 to 50% by mass, and further more preferably 5 to 30% by mass.

Other Ingredients

The composition according to the present invention may, if desired, contain photopolymerization initiators, photopolymerizable monomers, acid crosslinking substances, acid generating agents (for example, photoacid generating agent, thermal acid generating agents), base generating agents (for example, photobase generating agents, thermal base generating agents), coloring agents, dispersants, sensitizers, silicon-containing compounds, inorganic fillers, hydroxyl-group-containing compounds, carboxyl-group-containing compounds, and other various additives. Specific examples of these ingredients include those exemplified in the description on the first to sixth embodiments that will be described later. Further, the composition according to the present invention may, if desired, contain crystallization inhibitors, adhesion enhancers, and surfactants. When the composition according to the present invention contains a crystallization inhibitor, cracking is less likely to occur in the resultant cured product. When the composition according to the present invention contains an adhesion enhancer, the resultant cured product is likely to have improved adhesion to a base material and the like. Examples of surfactants include silicone-based surfactants and fluorine-based surfactants. When the composition according to the present invention contains a surfactant, the resultant cured product is likely to have an improved wettability and, consequently, a desired interface effect can easily be attained.

Examples of Composition

For example, the following first to tenth embodiments may be mentioned as the composition according to the present invention. These compositions, when heated, can be cured. Further, as described below, when these compositions contain photobase generating agents, photoacid generating agents, photopolymerization initiators, or photopolymerizable compounds such as a photopolymerizable monomer, the compositions are photosensitive. The compositions of the first to tenth embodiments will be described.

(1) Composition of First Embodiment

The composition of the first embodiment comprises: at least one of an alkali-soluble resin, a photopolymerizable monomer, and an organic solvent, a compound represented by the general formula (1), a compound represented by the general formula (10) and/or a compound represented by the general formula (19). The composition of the first embodiment may further contain a photopolymerization initiator.

Specific examples of the composition of the first embodiment include a non-photosensitive composition (1-1) comprising a compound represented by the general formula (1), a compound represented by the general formula (10) and/or a compound represented by the general formula (19) and an organic solvent, and a non-photosensitive resin composition (1-2) comprising an alkali-soluble resin, a compound represented by the general formula (1), a compound represented by the general formula (10) and/or a compound represented by the general formula (19). The non-photosensitive resin composition (1-2) may further contain an organic solvent.

A composition (1-3) comprising a photopolymerizable monomer, a compound represented by the general formula (1), a compound represented by the general formula (10) and/or a compound represented by the general formula (19) may also be mentioned as a specific example of the composition of the first embodiment. The composition (1-3) may further contain an organic solvent. When the photopolymerizable monomer is a compound that is liquid at room temperature, the composition may be prepared as a composition free from an organic solvent. Such photopolymerizable monomers include monofunctional or polyfunctional (meth)acrylate compounds, and monofunctional or difunctional (meth)acrylate compounds are preferred. Examples of such photopolymerizable monomers include lauryl (meth)acrylate, methoxytriethylene glycol (meth)acrylate, 1,6-hexanediol di(meth)acrylate, methoxyethylene glycol (meth)acrylate, ethylene glycol (meth)acrylate, propylene glycol (meth)acrylate, dipropylene glycol (meth)acrylate, and polyethylene glycol diacrylate. The composition (1-3) may further contain a photopolymerization initiator. When the photopolymerizable monomer contains a substance that initiates the polymerization reaction through the action of light or heat, the composition (1-3) may be prepared as a composition free from the photopolymerization initiator.

Further, a negative-type photosensitive resin composition (1-4) comprising an alkali-soluble resin, a photopolymerizable monomer, a photopolymerization initiator, a compound represented by the general formula (1), a compound represented by the general formula (10) and/or a compound represented by the general formula (19) may also be mentioned as a specific example of the composition of the first embodiment. The negative-type photosensitive resin composition (1-4) may further comprise an organic solvent.

As the alkali-soluble resin contained in the composition of the first embodiment, conventional publicly known alkali-soluble resins are usable without particular limitation. The alkali-soluble resin may be one which has an ethylenic unsaturated group or one which does not have any ethylenic unsaturated group.

As the alkali-soluble resin having an ethylenic unsaturated group, for example, resins obtainable by reacting a reaction product of an epoxy compound and unsaturated carboxylic acid with a polybasic acid anhydride are usable.

Among them, a resin having a cardo structure represented by the following general formula (r-1) is preferred. The resin represented by the formula (r-1) is preferred since the resin itself has high photo-curability. The resin represented by the formula (r-1) is preferred since the resin itself has high photo-curability.

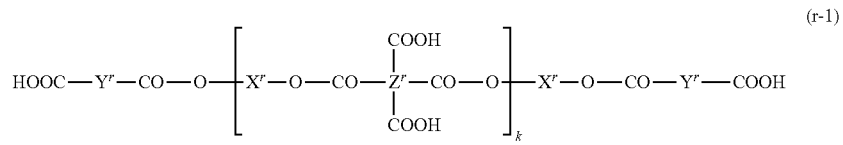

(r-1)

In the above formula (r-1), $X^r$ represents a group represented by the following general formula (r-2).

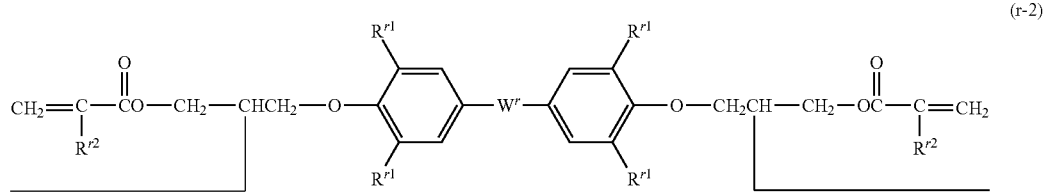

(r-2)

In the general formula (r-2), $R^{r1}$ each independently represent a hydrogen atom, a hydrocarbon group having 1 to 6 carbon atoms, or a halogen atom; $R^{r2}$ each independently represent a hydrogen atom or a methyl group; and $W^r$ represents a single bond or a group represented by the following general formula (r-3).

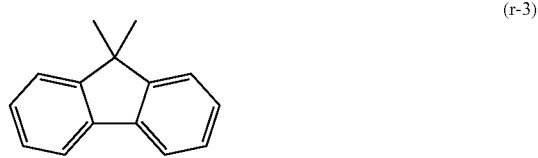

(r-3)

Also, in the general formula (r-1), $Y^r$ represents a residue obtainable by removing an acid anhydride group (—CO—O—CO—) from dicarboxylic anhydride. Examples of the dicarboxylic anhydride include maleic anhydride, succinic anhydride, itaconic anhydride, phthalic anhydride, tetrahydrophthalic anhydride, hexahydrophthalic anhydride, methylendomethylenetetrahydrophthalic anhydride, chlorendic anhydride, methyltetrahydrophthalic anhydride, anhydrous glutaric acid, and the like.

In the formula (r-1), $Z^r$ represents a residue obtainable by removing 2 acid anhydride groups from tetracarboxylic acid dianhydride. Examples of the tetracarboxylic acid dianhydride include pyromellitic dianhydride, benzophenonetetracarboxylic dianhydride, biphenyltetracarboxylic dianhydride, biphenylethertetracarboxylic dianhydride, and the like.

In the formula (r-1), k represents an integer of 0 to 20.

As the alkali-soluble resin having an ethylenic unsaturated group, polyester(meth)acrylate obtainable by causing a reaction between a polyester prepolymer obtained by condensation of polyvalent alcohols with monobasic acid or polybasic acid and (meth)acrylic acid; polyurethane(meth)acrylate obtainable by causing a reaction between polyol and a compound having 2 isocyanate groups and then performing a reaction with (meth)acrylic acid; an epoxy(meth)acrylate resin obtainable by causing a reaction between an epoxy resin such as bisphenol A-type epoxy resin, bisphenol F-type epoxy resin, bisphenol S-type epoxy resin, phenol or cresol novolac-type epoxy resin, resol-type epoxy resin, triphenolmethane-type epoxy resin, polycarboxylic acid polyglycidyl ester, polyol polyglycidyl ester, an aliphatic or alicyclic epoxy resin, an amine epoxy resin, and a dihydroxybenzene-type epoxy resin and a (meth)acrylic acid may be used.

The term "(meth)acrylic acid" as used herein means both acrylic acid and methacrylic acid. Likewise, the term "(meth)acrylate" means both acrylate and methacrylate. Further, "(meth)acrylamide" means both acrylamide and methacrylamide.

As the alkali-soluble resin which does not have any ethylenic unsaturated group, a resin which is obtainable by copolymerizing at least an unsaturated carboxylic acid, an epoxy group-containing unsaturated compound which does not have any alicyclic groups, and an alicyclic group-containing unsaturated compound may be used.

Examples of the unsaturated carboxylic acid include monocarboxylic acid such as (meth)acrylic acid and crotonic acid; dicarboxylic acid such as maleic acid, fumaric acid, citraconic acid, mesaconic acid, and itaconic acid; anhydrides of these dicarboxylic acids; and the like. Among these, (meth)acrylic acid and maleic anhydride are preferred from the viewpoints of copolymerization reactivity, alkali solubility of the obtained resin, easy availability, and so forth. These unsaturated carboxylic acids may be used alone or in combination of two or more kinds thereof.

Examples of the epoxy group-containing unsaturated compound which does not have any alicyclic groups include (meth)acrylic acid epoxyalkyl esters such as glycidyl (meth)acrylate, 2-methylglycidyl (meth)acrylate, 3,4-epoxybutyl (meth)acrylate, 6,7-epoxyheptyl (meth)acrylate, 3,4-epoxycyclohexyl (meth)acrylate; α-alkylacrylic acid epoxyalkyl esters such as glycidyl α-ethylacrylate, glycidyl α-n-propylacrylate, glycidyl α-n-butylacrylate, and 6,7-epoxyheptyl α-ethylacrylate; glycidyl ethers such as o-vinylbenzyl glycidyl ether, m-vinylbenzyl glycidyl ether, and p-vinylbenzyl glycidyl ether; and the like. Among these, glycidyl (meth)acrylate, 2-methylglycidyl (meth)acrylate, 6,7-epoxyheptyl (meth)acrylate, o-vinylbenzyl glycidyl ether, m-vinylbenzyl glycidyl ether and p-vinylbenzyl glycidyl ether are preferred from the viewpoints of copolymer reactivity, resin strength after curing, and so forth. These epoxy group-containing unsaturated compounds may be used alone or in combination of two or more kinds thereof.

As the alicyclic group-containing unsaturated compound, an unsaturated compound may be used without particular limitation insofar as the unsaturated compound has an alicyclic group. The alicyclic group may be monocyclic or polycyclic. Examples of monocyclic alicyclic groups include a cyclopentyl group, a cyclohexyl group, and the like. Examples of polycyclic alicyclic groups include an adamantyl group, a norbornyl group, an isobornyl group, a tricyclononyl group, a tricyclodecyl group, a tetracyclododecyl group, and the like. More specifically, examples of the alicyclic group-containing unsaturated compound include compounds represented by the following formula.

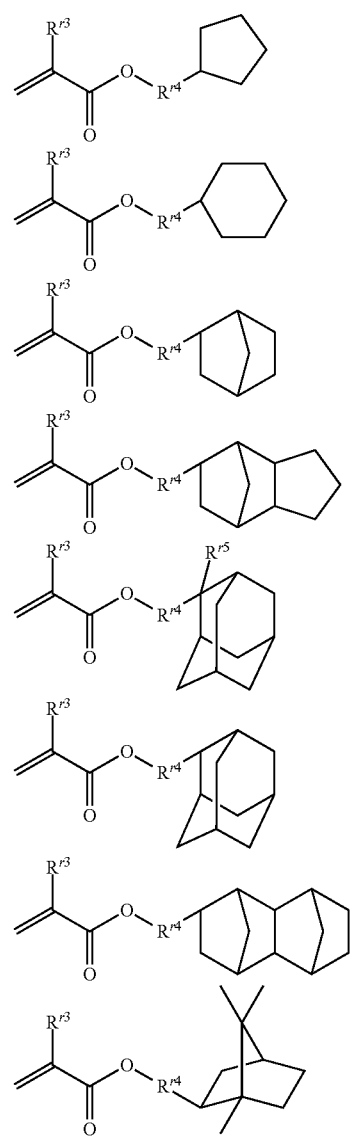

In the above formula, $R^{r3}$ represents a hydrogen atom or a methyl group; $R^{r4}$ represents a single bond or a divalent aliphatic saturated hydrocarbon group having 1 to 6 carbon atoms; and $R^{r5}$ represents a hydrogen atom or an alkyl group having 1 to 5 carbon atoms. As $R^{r4}$, a single bond and a straight chain or branched chain alkylene group such as a methylene group, an ethylene group, a propylene group, a tetramethylene group, an ethylethylene group, a pentamethylene group, and a hexamethylene group are preferred. As $R^{r5}$, a methyl group and an ethyl group are preferred.

In the alkali-soluble resin, a ratio of a constitutional unit derived from the unsaturated carboxylic acid is preferably 3 to 25 mass %, more preferably 5 to 25 mass %. Also, a ratio of a constitutional unit derived from the epoxy group-containing unsaturated compound is preferably 71 to 95 mass %, more preferably 75 to 90 mass %. Also, a ratio of a constitutional unit derived from the alicyclic group-containing unsaturated compound is preferably 1 to 25 mass %, more preferably 3 to 20 mass %, further preferably 5 to 15 mass %. With the above-specified ranges, it is possible to enhance the adhesiveness of the composition to substrates and the strength of the composition after curing while maintaining alkali solubility of the obtained resin at an appropriate level.

The mass average molecular weight of the alkali-soluble resin is preferably 1000 to 40000, more preferably 2000 to 30000. A mass average molecular weight in the above-defined range is advantageous in that satisfactory heat resistance and film strength can be obtained and, when the composition of the first embodiment is a negative-type photosensitive resin composition, good developability can be realized.

The content of the alkali-soluble resin is preferably 5 to 80% by mass, more preferably 15 to 50% by mass, relative to the solid content of the composition of the first embodiment. An alkali-soluble resin content in the above-defined range is advantageous in that an improvement in a coating film forming capability of the composition of the first embodiment can easily be achieved and, when the composition of the first embodiment is a negative-type photosensitive resin composition, a good balance of developability can be realized.

Monofunctional monomers and polyfunctional monomers may be mentioned as the photopolymerizable monomer in the composition of the first embodiment.

Examples of the monofunctional monomer include (meth) acryl amide, methylol(meth)acrylamide, methoxymethyl (meth)acrylamide, ethoxymethyl(meth)acrylamide, propoxymethyl(meth)acrylamide, butoxymethoxymethyl (meth)acrylamide, N-methylol(meth)acrylamide, N-hydroxymethyl(meth)acrylamide, (meth)acrylic acid, fumaric acid, maleic acid, maleic anhydride, itaconic acid, itaconic anhydride, citraconic acid, citraconic anhydride, crotonic acid, 2-acrylamide-2-methylpropanesulfonic acid, tert-butylacrylamidesulfonic acid, methyl (meth)acrylate, ethyl (meth)acrylate, butyl (meth)acrylate, 2-ethylhexyl (meth) acrylate, lauryl (meth)acrylate, cyclohexyl (meth)acrylate, 2-hydroxyethyl (meth)acrylate, 2-hydroxypropyl (meth) acrylate, 2-hydroxybutyl (meth)acrylate, 2-phenoxy-2-hydroxypropyl (meth)acrylate, 2-(meth)acryloyloxy-2-hydroxypropyl phthalate, glycerin mono(meth)acrylate, tetrahydrofurfuryl (meth)acrylate, dimethylamino (meth) acrylate, glycidyl (meth)acrylate, 2,2,2-trifluoroethyl (meth) acrylate, 2,2,3,3-tetrafluoropropyl (meth)acrylate, half (meth)acrylate of a phthalic acid derivative, and the like. These monofunctional monomers may be used alone or in combination of two or more kinds thereof.

Meanwhile, examples of the polyfunctional monomer include ethylene glycol di(meth)acrylate, diethylene glycol di(meth)acrylate, tetraethylene glycol di(meth)acrylate, propylene glycol di(meth)acrylate, polypropylene glycol di(meth)acrylate, butylene glycol di(meth)acrylate, neopentyl glycol di(meth)acrylate, 1,6-hexane glycol di(meth)acrylate, trimethylolpropane tri(meth)acrylate, glycerin di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri (meth)acrylate, pentaerythritol tetra(meth)acrylate, dipentaerythritol penta(meth)acrylate, dipentaerythritol hexa (meth)acrylate, 2,2-bis(4-(meth)acryloxydiethoxyphenyl) propane, 2,2-bis(4-(meth)acryloxypolyethoxyphenyl) propane, 2-hydroxy-3-(meth)acryloyloxypropyl (meth) acrylate, ethylene glycol diglycidyl ether di(meth)acrylate, diethylene glycol diglycidyl ether di(meth)acrylate, phthalic acid diglycidyl ester di(meth)acrylate, glycerin triacrylate, glycerin polyglycidyl ether poly(meth)acrylate, urethane (meth)acrylate (i.e. tolylene diisocyanate), a reaction product of trimethylhexamethylene diisocyanate, hexamethylene diisocyanate, and 2-hydroxyethyl (meth)acrylate, methylene bis(meth)acrylamide, (meth)acrylamide methylene ether, a polyfunctional monomer such as a condensate of a polyvalent alcohol and N-methylol(meth)acrylamide, triacryl formal, and the like. These polyfunctional monomers may be used alone or in combination of two or more kinds thereof.

The content of the photopolymerizable monomer is preferably 1 to 30% by mass, more preferably 5 to 20% by mass, relative to the solid content of the composition of the first embodiment. The content in the above-defined range is advantageous in that a good balance between the sensitivity, the developability, and the resolution is likely to be realized.

The photopolymerization initiator in the composition of the first embodiment is not particularly limited, and conventional photopolymerization initiators may be used.

Specific examples of the photopolymerization initiator include 1-hydroxy-cyclohexylphenylketone, 2-hydroxy-2-methyl-1-phenylpropan-1-one, 1-[4-(2-hydroxyethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4-dimethylaminophenyl)ketone, 2-methyl-1-[4-(methylthio) phenyl]-2-morpholinopropan-1-one, 2-benzyl-2-dimethylamino-1-(4-morpholinophenyl)-butan-1-one, ethanone, 1-[9-ethyl-6-(2-methylbenzoyl)-9H-carbozol-3-yl], 1-(o-acetyloxime), 2,4,6-trimethylbenzoyldiphenylphosphineoxide, 4-benzoyl-4'-methyldimethylsulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexylbenzoic acid, 4-dimethylamino-2-isoamylbenzoic acid, benzyl-β-methoxyethylacetal, benzyldimethylketal, 1-phenyl-1,2-propanedione-2-(o-ethoxycarbonyl)oxime, methyl o-benzoylbenzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene peroxide, 2-mercaptobenzimidazole, 2-mercaptobenzoxazole, 2-mercaptobenzothiazole, 2-(o-chlorophenyl)-4,5-diphenylimidazole dimers, 2-(o-chlorophenyl)4,5-di(methoxyphenyl)imidazole dimers, 2-(o-fluorophenyl)-4,5-diphenylimidazole dimers, 2-(o-methoxyphenyl)-4,5-diphenylimidazole dimers, 2-(p-methoxyphenyl)-4,5-diphenylimidazole dimers, 2,4,5-triarylimidazole dimers, benzophenone, 2-chlorobenzophenone, 4,4'-bisdiethylaminobenzophenone (i.e. Michler's ketone), 4,4'-bisdiethylaminobenzophenone (i.e. ethyl Michler's ketone), 4,4'-dichlorobenzophenone, 3,3-dimethyl-4-methoxybenzophenone, benzyl, benzoin, benzoin methyl ether, benzoin ethyl ether, benzoin isopropyl ether, benzoin-n-butyl ether, benzoin isobutyl ether, benzoin butyl ether, acetophenone, 2,2-diethoxyacetophenone, p-dimethylacetophenone, p-dimethylaminopropiophenone, dichloroacetophenone, trichloroacetophenone, p-tert-butylacetophenone, p-dimethylaminoacetophenone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl-4-dimethylamino benzoate, 9-phenylacridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy)styrylphenyl-s-triazine, 2,4-bis-trichloromethyl-6-(2-bromo-4-methoxy) styrylphenyl-s-triazine, and the like. Among them, oxime-based photopolymerization initiators are preferably used from the viewpoint of sensitivity. These photopolymerization initiators may be used solely or in a combination of two or more thereof.

The content of the photopolymerization initiator is preferably 0.5 to 20 parts by mass relative to 100 parts by mass of the solid content of the composition of the first embodiment. A photopolymerization initiator content in the above-defined range is advantageous in that satisfactory heat resistance and chemical resistance can be realized and, at the same time, an improvement in coating film forming capability and the suppression of a failure to cure can can be realized.

As described above, the composition of the first embodiment comprises a compound represented by the general formula (1), a compound represented by the general formula (10) and/or a compound represented by the general formula (19). Cured products having a high hardness can easily be obtained from the composition containing this compound. Further, when this compound is incorporated in a negative-type photosensitive resin composition, good micropatterning properties can be realized.

The content of the compound represented by the general formula (1), the compound represented by the general formula (10) and/or the compound represented by the general formula (19) is preferably 1 to 100% by mass, more preferably 3 to 80% by mass, further preferably 5 to 50% by mass, relative to the solid content of the composition of the first embodiment. In particular, when the composition of the first embodiment contains at least a of the alkali-soluble resin, the photopolymerizable monomer, and the photopolymerization initiator, the content is preferably 1 to 99% by mass, more preferably 3 to 80% by mass, further preferably 5 to 50% by mass, relative to the solid content of the composition of the first embodiment. A content in the above-defined range is advantageous in that an improvement in coating film forming capability and curability of the composition of the first embodiment can easily be realized and, when the composition of the first embodiment is a negative-type photosensitive resin composition, good micropatterning properties can be provided while realizing good developability.

The composition of the first embodiment may further comprise a coloring agent. When the coloring agent is contained, the composition is favorably used, for example, for the formation of color filters of liquid crystal displays. Also, when the composition of the first embodiment contains a light shielding agent as the coloring agent, it is favorably used, for example, for the formation of black matrixes in color filters.

The coloring agent is not particularly limited, but it is preferable to use, for example, compounds which are classified "Pigment" in the Color Index (C.I.; published by The Society of Dyers and Colorist), and specifically those having the following color index (C.I.) numbers.

C.I. pigment yellow 1 (hereinafter, "C.I. pigment yellow" is omitted, and only the numbers are listed) 3, 11, 12, 13, 14, 15, 16, 17, 20, 24, 31, 53, 55, 60, 61, 65, 71, 73, 74, 81, 83, 86, 93, 95, 97, 98, 99, 100, 101, 104, 106, 108, 109, 110, 113, 114, 116, 117, 119, 120, 125, 126, 127, 128, 129, 137, 138, 139, 147, 148, 150, 151, 152, 153, 154, 155, 156, 166, 167, 168, 175, 180, 185;

C.I. pigment orange 1 (hereinafter, "C.I. pigment orange" is omitted, and only the numbers are listed) 5, 13, 14, 16, 17, 24, 34, 36, 38, 40, 43, 46, 49, 51, 55, 59, 61, 63, 64, 71, 73;

C.I. pigment violet 1 (hereinafter, "C.I. pigment violet" is omitted, and only the numbers are listed) 19, 23, 29, 30, 32, 36, 37, 38, 39, 40, 50;

C.I. pigment red 1 (hereinafter, "C.I. pigment red" is omitted, and only the numbers are listed) 2, 3, 4, 5, 6, 7, 8, 9, 10, 11, 12, 14, 15, 16, 17, 18, 19, 21, 22, 23, 30, 31, 32, 37, 38, 40, 41, 42, 48:1, 48:2, 48:3, 48:4, 49:1, 49:2, 50:1, 52:1, 53:1, 57, 57:1, 57:2, 58:2, 58:4, 60:1, 63:1, 63:2, 64:1, 81:1, 83, 88, 90:1, 97, 101, 102, 104, 105, 106, 108, 112, 113, 114, 122, 123, 144, 146, 149, 150, 151, 155, 166, 168, 170, 171, 172, 174, 175, 176, 177, 178, 179, 180, 185, 187, 188, 190, 192, 193, 194, 202, 206, 207, 208, 209, 215, 216, 217, 220, 223, 224, 226, 227, 228, 240, 242, 243, 245, 254, 255, 264, 265;

C.I. pigment blue 1 (hereinafter, "C.I. pigment blue" is omitted, and only the numbers are listed) 2, 15, 15:3, 15:4, 15:6, 16, 22, 60, 64, 66;

C.I. pigment green 7, C.I. pigment green 36, and C.I. pigment green 37;

C.I. pigment brown 23, C.I. pigment brown 25, C.I. pigment brown 26, and C.I. pigment brown 28; and C.I. pigment black 1 and C.I. pigment black 7.

In the case where the light shielding agent is used as the coloring agent, it is preferable to use a black pigment as the light shielding agent. Examples of the black pigment include various types of pigments irrespective of whether it is an organic substance or an inorganic substance, such as carbon black, titanium black, and a metal oxide, composite oxide, metal sulfide, metal sulfate, and metal carbonate of copper, iron, manganese, cobalt, chromium, nickel, zinc, calcium, silver, or the like. Among these, it is preferable to use carbon black, which has a high light shielding property.

As the carbon black, known carbon black such as channel black, furnace black, thermal black, and lamp black are usable, and it is preferable to use channel black, which has excellent light shielding properties. A resin-coated carbon black may also be used.

Since the resin coated carbon black has lower conductivity than the carbon black without resin coating, it is less subject to electric current leakage when used for black matrixes of liquid crystal display devices and enables production of highly reliable displays with low power consumption.

Each of the above organic pigments may be added as an auxiliary pigment as required in order to adjust a color tone of the carbon black.

Further, a dispersant may be used for uniformly dispersing the coloring agent in the negative-type photosensitive resin composition. As the dispersant, polyethylene imine-based, urethane resin-based, and acryl resin-based polymer dispersants are preferably used. Particularly, in the case where carbon black is used as the coloring agent, it is preferable to use the acryl resin-based dispersant as the dispersant.

Also, the inorganic pigments and the organic pigments may be used alone or in combination, and, in the case of combined use, the organic pigment may be used within the range of 10 to 80 parts by mass, more preferably within the range of 20 to 40 parts by mass, relative to 100 parts by mass in total of the inorganic pigment and the organic pigment.

A content of the coloring agent may appropriately be determined depending on the usage of the composition of the first embodiment, and, as one example, the content is preferably 5 to 70 parts by mass, more preferably 25 to 60 parts by mass, relative to 100 parts by mass of the solid content of the composition of the first embodiment.

Particularly, in the case of forming a black matrix by using the composition of the first embodiment, it is preferable to adjust the amount of the light shielding agent in the negative-type photosensitive resin composition so that an OD value per 1 μm of film thickness of the black matrix is 4 or more. With an OD value of 4 or more per 1 μm of film thickness in the black matrix, it is possible to attain satisfactory display contrast when the negative-type photosensitive resin composition is used for black matrixes of liquid crystal displays.

It is preferable to add to the negative-type photosensitive resin composition the coloring agent as a dispersion which is obtained by dispersing the coloring agent at an appropriate concentration by using a dispersant.

Examples of the organic solvent in the composition of the first embodiment include (poly)alkylene glycol monoalkyl ethers such as ethylene glycol monomethyl ether, ethylene glycol monoethyl ether, ethylene glycol-n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether, propylene glycol monoethyl ether, propylene glycol mono-n-propyl ether, propylene glycol mono-n-butyl ether, dipropylene glycol monomethyl ether, dipropylene glycol monoethyl ether, dipropylene glycol mono-n-propyl ether, dipropylene glycol mono-n-butyl ether, tripropylene glycol monomethyl ether, and tripropylene glycol monoethyl ether; (poly)alkylene glycol monoalkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, and propylene glycol monoethyl ether acetate; other ethers such as diethylene glycol dimethyl ether, diethylene glycol methylethyl ether, diethylene glycol diethyl ether, and tetrahydrofuran; ketones such as methyl ethyl ketone, cyclohexanone, 2-heptanone, and 3-heptanone; alkyl ester lactates such as methyl 2-hydroxypropionate and ethyl 2-hydroxypropionate; other esters such as ethyl 2-hydroxy-2-methylpropionate, methyl 3-methoxypropionate, ethyl 3-methoxy propionate, methyl 3-ethoxypropionate, ethyl 3-ethoxypropionate, ethyl ethoxyacetate, ethyl hydroxyacetate, methyl 2-hydroxy-3-methylbutanoate, 3-methyl-3-methoxybutylacetate, 3-methyl-3-methoxybutylpropionate, ethyl acetate, n-propyl acetate, isopropyl acetate, n-butyl acetate, isobutyl acetate, n-pentyl formate, isopentyl acetate, n-butyl propionate, ethyl butyrate, n-propyl butyrate, isopropyl butyrate, n-butyl butyrate, methyl pyruvate, ethyl pyruvate, n-propyl pyruvate, methyl acetoacetate, ethyl acetoacetate, and ethyl 2-oxobutanoate; aromatic hydrocarbons such as toluene and xylene; amides such as N-methylpyrrolidone, N,N-dimethylformamide, and N,N-dimethylacetamide; and the like. These organic solvents may be used alone or in combination of two or more kinds thereof.

Among the above organic solvents, propylene glycol monomethyl ether, ethylene glycol monomethyl ether acetate, propylene glycol monomethyl ether acetate, propyleneglycol monoethyl ether acetate, diethylene glycol dimethyl ether, diethylene glycol methylethyl ether, cyclohexanone, 3-methoxybutyl acetate are preferred since they exhibit excellent solubility with respect to the alkali-soluble resin, the photopolymerizable monomer, the photopolymerization initiator, and the compound represented by the formula (1) and improve a dispersing property of the coloring agent, and it is particularly preferable to use propylene glycol monomethyl ether acetate or 3-methoxybutyl acetate.

A content of the organic solvent is preferably such that a solid content concentration of the composition of the first embodiment is 1 to 50 mass %, more preferably 5 to 30 mass %.

The composition of the first embodiment may contain various additives as required. Examples of the additives include a sensitizer, a curing accelerator, a filler, an adhesion accelerator, an antioxidant, an ultraviolet ray absorber, a flocculation inhibitor, a thermal polymerization inhibitor, an anti-foaming agent, a surfactant, and the like.

(2) Composition of Second Embodiment

The composition of the second embodiment is a resin composition comprising an alkali-soluble resin containing a phenolic hydroxyl group, an alkali-soluble resin containing a naphtholic hydroxyl group, an alkali-soluble resin containing a thiophenolic thiol group and/or an alkali-soluble resin containing a thionaphtholic thiol group, a compound represented by the general formula (1), a compound represented by the general formula (10), and/or a compound represented by the general formula (19). The composition of the second embodiment may further contain an acid cross-linking substance, a photoacid generating agent, and/or an organic solvent. When the composition of the second embodiment does not contain the photoacid generating agent, the composition is a non-photosensitive resin composition. However, when the composition contains a photoacid generating agent, the composition is photosensitive.

When the composition of the second embodiment is photosensitive, specific examples thereof include negative-type photosensitive resin compositions comprising an alkali-soluble resin containing a phenolic hydroxyl group, an alkali-soluble resin containing a naphtholic hydroxyl group, an alkali-soluble resin containing a thiophenolic thiol group and/or an alkali-soluble resin containing a thionaphtholic thiol group, a photoacid generating agent, a compound represented by the general formula (1), a compound represented by the general formula (10), and/or a compound represented by the general formula (19). The negative-type photosensitive resin composition may further contain an acid crosslinking substance and/or an organic solvent.

For example, polyhydroxystyrene-based resins may be used as the alkali-soluble resin having a phenolic hydroxyl group in the composition of the second embodiment.

The polyhydroxystyrene-based resin contains at least a constituent unit derived from a hydroxystyrene.

Here, "hydroxystyrene" is taken as a concept including hydroxystyrene, and hydroxystyrene derivatives where the hydrogen atom bonded at the α-position of the hydroxystyrene is substituted with another substituent group such as a halogen atom, an alkyl group, a halogenated alkyl group and the like, as well as derivatives thereof (monomers).

"Hydroxystyrene derivatives" encompasses those where at least a benzene ring and a hydroxyl group bonded thereto are maintained, for example those where the hydrogen atom bonded at the α-position of the hydroxystyrene is substituted with another substituent group such as a halogen atom, an alkyl group having 1 to 5 carbon atoms, a halogenated alkyl group and the like, and those where at the benzene ring to which the hydroxyl group of the hydroxystyrene is bonded, an alkyl group having 1 to 5 carbon atoms is further bonded, or where at the benzene group to which this hydroxyl group is bonded, 1 to 2 hydroxyl groups are further bonded (when this is the case, the total number of hydroxyl groups is 2 to 3), or the like.

As the halogen atom, a chlorine atom, a fluorine atom, a bromine atom and the like may be mentioned, and a fluorine atom is preferable.

Further, the "α-position of the hydroxystyrene", unless otherwise noted, refers to the carbon atom bonded to the benzene ring.

These constituent units derived from hydroxystyrene are represented, for example, by the following general formula (s-1).

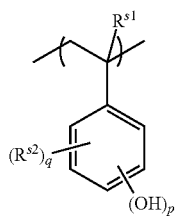

(s-1)

In the general formula (s-1), $R^{s1}$ represents a hydrogen atom, an alkyl group, a halogen atom, or a a halogenated alkyl group, $R^{s2}$ represents an alkyl group having 1 to 5 carbon atoms, p represents an integer of 1 to 3, and q represents an integer of 0 to 2.

The alkyl group represented by $R^{s1}$ preferably has 1 to 5 carbon atoms. Further, a straight chain or branched chain alkyl group is preferable, and a methyl group, an ethyl group, a propyl group, an isopropyl group, an n-butyl group, a tert-butyl group, a pentyl group, an isopentyl group, a neopentyl group, and the like may also be used. Among these, a methyl group is preferable from the viewpoint of industry.

As the halogen atom, a fluorine atom, chlorine atom, a bromine atom, an iodine atom and the like may be mentioned, and a fluorine atom is preferred.

The halogenated alkyl group is one where a portion or all of the hydrogen atoms of the above described alkyl group having 1 to 5 carbon atoms is substituted with a halogen atom. Among these, it is preferable for all of the hydrogen atoms to be substituted with fluorine atoms. Further, a straight chain or branched chain fluorinated alkyl group is preferable, and a trifluoromethyl group, a hexafluoroethyl group, a heptafluoropropyl group, a nonafluorobutyl group and the like are preferable, and a trifluoromethyl group ($-CF_3$) is most preferable.

As $R^{s1}$, a hydrogen atom or methyl group is preferable, and a hydrogen atom is more preferable.

As the alkyl group having 1 to 5 carbon atoms of $R^{s2}$, the same as for $R^{s1}$ may be mentioned.

q is an integer of 0 to 2. Among these, 0 or 1 is preferable, and 0 is particularly preferable industrially.

The substitution position of $R^{s2}$ may be any of the ortho position, meta position, or para position in the case that q is 1, and further, may be any arbitrary combination of substitution positions when q is 2.

p is an integer of 1 to 3, and is preferably 1.

The substitution position of the hydroxyl group may be any of the ortho position, meta position, or para position when p is 1, and the para position is preferable because it is readily available at low cost. Further, when p is 2 or 3, arbitrary substitution positions may be combined.

The constituent unit represented by the general formula (s-1) may be used alone or in combinations of two or more thereof.

In the polyhydroxystyrene resin, the proportion of constituent units derived from hydroxystyrene is preferably 60 to 100 mol % with respect to all of the constituent units constituting the polyhydroxystyrene, more preferably 70 to 100 mol %, and even more preferably 80 to 100 mol %. With the above range, it is possible to obtain proper alkali solubility when making the negative-type photosensitive resin composition.

The polyhydroxystyrene resin preferably further has constituent units derived from styrene.

Herein, "constituent units derived from styrene" encompasses constituent units wherein the ethylenic double bond of styrene or styrene derivatives (however, not including hydroxystyrene) is cleaved.

"Styrene derivatives" encompass those where a hydrogen atom bonded to the α-position of the styrene is substituted with another substituent group such as a halogen atom, alkyl group, halogenated alkyl group and the like, and those where the hydrogen atom of the phenyl group of the styrene is substituted with a substituent group such as an alkyl group having 1 to 5 carbon atoms, and the like.

As the halogen atom, a chlorine atom, fluorine atom, bromine atom and the like may be mentioned, and a fluorine atom is preferable.

Further, the "α-position of the styrene", unless otherwise noted, refers to the carbon atom bonded to the benzene ring.

The constituent units derived from the styrene are represented, for example, by the following general formula (s-2). In the formula, $R^{s1}$, $R^{s2}$, and q are the same as for the general formula (s-1).

(s-2)

As $R^{s1}$ and $R^{s2}$, the same as the respective $R^{s1}$ and $R^{s2}$ of the general formula (s-1) may be mentioned.

q is an integer of 0 to 2. Among these, 0 or 1 is preferable, and 0 is especially preferable industrially.

The substitution position of $R^{s2}$ may be an ortho position, meta position, or para position when q is 1, and further, when q is 2, arbitrary substitution positions may be combined.

The constituent units represented by the general formula (s-2) may be used alone or in combinations of two or more thereof.

In the polyhydroxystyrene resin, the proportion of constituent units derived from styrene is preferably 40 mol % or less with respect to all of the constituent units constituting the polyhydroxystyrene, more preferably 30 mol % or less, and even more preferably 20 mol % or less. With the above range, it is possible to obtain proper alkali solubility when making the negative-type photosensitive resin composition, and the balance with the other constituent units also becomes favorable.

Further, the polyhydroxystyrene resin may have constituent units other than the constituent units derived from hydroxystyrene and the constituent units derived from styrene. More preferably, the above polyhydroxystyrene resin is a polymer consisting only of constituent units derived from hydroxystyrene, or a copolymer consisting of constituent units derived from hydroxystyrene and constituent units derived from styrene.

The mass average molecular weight of the polyhydroxystyrene resin is not particularly limited, but is preferably 1500 to 40000, more preferably 2000 to 8000.

Further, as the alkali-soluble resin having a phenolic hydroxyl group, a novolak resin may be used. This novolak resin may be obtained by addition condensation of a phenol and an aldehyde under the presence of an acid catalyst.

As the phenol, cresols such as phenol, o-cresol, m-cresol, p-cresol and the like; xylenols such as 2,3-xylenol, 2,4-xylenol, 2,5-xylenol, 2,6-xylenol, 3,4-xylenol, 3,5-xylenol and the like; alkylphenols such as o-ethylphenol, m-ethylphenol, p-ethylphenol, 2-isopropylphenol, 3-isopropylphenol, 4-isopropylphenol, o-butylphenol, m-butylphenol, p-butylphenol, p-tert-butylphenol and the like; trialkylphenols such as 2,3,5-trimethylphenol, 3,4,5-trimethylphenol and the like; polyphenols such as resorcinol, catechol, hydroquinone, hydroquinone monomethyl ether, pyrogallol, phluoroglucinol and the like; alkyl polyphenols such as alkylresorcinol, alkyl catechol, alkyl hydroquinone and the like (where all alkyl groups have 1 to 4 carbon atoms); α-naphthol, β-naphthol, hydroxydiphenyl, bisphenol A, bisphenol F, bisphenol S and the like, may be mentioned. These phenols may be used alone or in combinations of two or more kinds thereof.

Even among these phenols, m-cresol and p-cresol are preferable, and the combined use of m-cresol and p-cresol is more preferable. In this case, by adjusting the mixing ratio of the two, it is possible to adjust various characteristics such as the sensitivity and the like.

As the aldehyde, formaldehyde, paraformaldehyde, furfural, benzaldehyde, nitrobenzaldehyde, acetaldehyde and the like can be used. These aldehydes may be used alone or in combinations of two or more kinds thereof.

As the acid catalyst, inorganic acids such as hydrochloric acid, sulfuric acid, nitric acid, phosphoric acid, phosphonic acid, and the like; and organic acids such as formic acid, oxalic acid, acetic acid, diethyl sulfate, paratoluenesulfonic acid and the like; metal salts such as zinc acetate and the like; and the like may be mentioned. These acid catalysts may be used alone or in combinations of two or more kinds thereof.

As novolak resins which can be obtained in this way, specifically, phenol/formaldehyde condensation novolak resin, cresol/formaldehyde condensation novolak resin, phenol-naphthol/formaldehyde condensation novolak resin and the like may be mentioned.

The mass average molecular weight of the novolak resin is not particularly limited, but is preferably 1000 to 30000, more preferably 3,000 to 25000.

Further, as the alkali-soluble resin having a phenolic hydroxyl group, phenol-xylylene glycol condensation resin, cresol-xylylene glycol condensation resin, and phenol-dicyclopentadiene condensation resin and the like may be used.

Alkali-soluble resins containing a naphtholic hydroxyl group include, for example, resins exemplified as alkali-soluble resins containing a phenolic hydroxyl group with the hydroxyphenyl group replaced by a hydroxynaphthyl group, more specifically, for example, polyhydroxystyrene-based resins with the hydroxyphenyl group replaced by a hydroxynaphthyl group.

Alkali-soluble resins containing a thiophenolic thiol group include, for example, resins exemplified as alkali-soluble resins containing a phenolic hydroxyl group with the hydroxyphenyl group replaced by a mercaptophenyl group, more specifically, for example, polyhydroxystyrene-based resins with the hydroxyphenyl group replaced by a mercaptophenyl group.

Alkali-soluble resins containing a thionaphtholic thiol group include, for example, resins exemplified as alkali-soluble resins containing a phenolic hydroxyl group with the hydroxyphenyl group replaced by a mercaptonaphthyl group, more specifically, for example, polyhydroxystyrene-based resins with the hydroxyphenyl group replaced by a mercaptonaphthyl group.

The content of the alkali-soluble resin containing a phenolic hydroxyl group, the alkali-soluble resin containing a naphtholic hydroxyl group, the alkali-soluble resin containing a thiophenolic thiol group and/or the alkali-soluble resin containing a thionaphtholic thiol group is preferably 20 to 80% by mass, more preferably 35 to 65% by mass, relative to the solid content of the composition of the second embodiment. The content in the above-defined range is advantageous in that an improvement in coating film forming capability and the like of the composition of the second embodiment can easily be realized and, when the composition of the second embodiment is a negative-type photosensitive resin composition, a good balance of developability can easily be realized.

In the composition of the second embodiment, the acid crosslinking substance is not particularly limited, and conventional acid crosslinking substances may be used.

As the acid crosslinking substance, specifically, an amino resin having a hydroxyl group or an alkyoxy group, for example a melamine resin, a urea resin, a guanamine resin, an acetoguanamine resin, a benzoguanamine resin, a glycoluril-formaldehyde resin, a succinyl amide-formaldehyde resin, an ethylene urea-formaldehyde resin, and the like may be mentioned. These acid crosslinking substances are readily obtained by reacting melamine, urea, guanamine, acetoguanamine, benzoguanamine, glycoluril, succinyl amide, ethylene urea with formalin in boiling water and methylolating, or further reacting these with a lower alcohol, and alkoxylating. Practically, they may be obtained as a melamine resin such as Nikalac MX-750, Nikalac MW-30, Nikalac MW$^{100}$LM and the like, or a urea resin such as Nikalac MX-290 and the like (all manufactured by Sanwa Chemical Co. Ltd.). Further, benzoguanamine resins may also be obtained as commercial products such as Cymel 1123 and Cymel 1128 (manufactured by Mitsui Cyanade Co., Ltd.).

Further, a benzene compound having an alkoxy group such as 1,3,5-tris(methoxymethoxy)benzene, 1,2,4-tris(isopropoxymethoxy)benzene, 1,4-bis(sec-butoxymethoxy)benzene and the like, and a phenol compound having a hydroxyl group or an alkoxy group such as 2,6-dihydroxymethyl-p-tert-butylphenol and the like may be used.

These acid crosslinking substances may be used alone or in combinations of two or more kinds thereof.

The content of these acid crosslinking substances is preferably 5 to 50 parts by mass, more preferably 10 to 30 parts by mass, with respect to 100 parts by mass of the alkali-soluble resin having a phenolic hydroxyl group. The content in the above-defined range is advantageous in that an improvement in curability of the composition of the second embodiment can easily be realized and, when the composition of the second embodiment is a negative-type photosensitive resin composition, good patterning properties can be realized.

In the composition of the second embodiment, the photoacid generating agent is not particularly limited, and conventional photoacid generating agents may be used.

As the photoacid generating agent, specifically, an onium salt acid generating agent such as iodonium salt or sulfonium salt or the like, an oxime sulfonate acid generating agent, a halogen-containing triazine compound, a diazomethane acid generating agent, a nitrobenzyl sulfonate acid generating agent (nitrobenzyl derivative), iminosulfonate acid generating agent, disulfone acid generating agent, and the like may be mentioned.

As a preferable sulfonium salt acid generating agent, a compound represented by the following general formula (t-1) may be mentioned, for example.

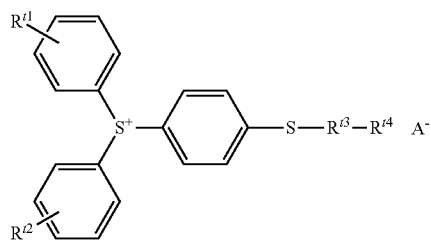

(t-1)

In the general formula (t-1), $R^{t1}$ and $R^{t2}$ respectively and independently represent a hydrogen atom, a halogen atom, an oxygen atom or a hydrocarbon group which may have a halogen atom, or an alkoxy group which may have a substituent group; $R^{t3}$ represents a p-phenylene group which may have a halogen atom or an alkyl group; $R^{t4}$ represents a halogen atom, an oxygen atom or a hydrocarbon group which may have a halogen atom, a benzoyl group which may have a substituent group, or a polyphenyl group which may have a substituent group; and $A^-$ represents a counterion to the onium ion.

As $A^-$, specifically, $SbF_6^-$, $PF_6^-$, $AsF_6^-$, $BF_4^-$, $SbCl_6^-$, $ClO_4^-$, $CF_3SO_3^-$, $CH_3SO_3^-$, $FSO_3^-$, $F_2PO_2^-$, p-toluenesulfonate, nonafluorobutanesulfonate, adamantane carboxylate, tetraaryl borate, fluorinated alkyl fluorophosphate anions represented by the following general formula (t-2), and the like may be mentioned.

$$[(Rf)_g PF_{6-g}]^- \qquad (t-2)$$

In the general formula (t-2), Rf represents an alkyl group where 80% or more of the hydrogen atoms have been substituted with a fluorine atom. g is the counter thereof and represents an integer of 1 to 5. The g units of Rf may each be the same, or may be different.

As the photoacid generating agent represented by the general formula (t-1), 4-(2-chloro-4-benzoylphenylthio)phenyldiphenylsulfonium hexafluoroantimonate, 4-(2-chloro-4-benzoylphenylthio)phenylbis(4-fluorophenyl)sulfonium hexafluoroantimonate, 4-(2-chloro-4-benzoylphenylthio)phenylbis(4-chlorophenyl)sulfonium hexafluoroantimonate, 4-(2-chloro-4-benzoylphenylthio)phenylbis(4-methylphenyl)sulfonium hexafluoroantimonate, 4-(2-chloro-4-benzoylphenylthio)phenylbis(4-(β-hydroxyethoxy)phenyl)sulfonium hexafluoroantimonate, 4-(2-methyl-4-benzoylphenylthio)phenylbis(4-fluorophenyl)sulfonium hexafluoroantimonate, 4-(3-methyl-4-benzoylphenylthio)phenylbis(4-fluorophenyl)sulfonium hexafluoroantimonate, 4-(2-fluoro-4-benzoylphenylthio)phenylbis(4-fluorophenyl)sulfonium hexafluoroantimonate, 4-(2-methyl-4-benzoylphenylthio)phenylbis(4-fluorophenyl)sulfonium hexafluoroantimonate, 4-(2,3,5,6-tetramethyl-4-benzoylphenylthio)phenylbis(4-fluorophenyl)sulfonium hexafluoroantimonate, 4-(2,6-dichloro-4-benzoylphenylthio)phenylbis(4-fluorophenyl)sulfonium hexafluoroantimonate, 4-(2,6-dimethyl-4-benzoylphenylthio)phenylbis(4-fluorophenyl)sulfonium hexafluoroantimonate, 4-(2,3-dimethyl-4-benzoylphenylthio)phenylbis(4-fluorophenyl)sulfonium hexafluoroantimonate, 4-(2-methyl-4-benzoylphenylthio)phenylbis(4-chlorophenyl)sulfonium hexafluoroantimonate, 4-(3-methyl-4-benzoylphenylthio)phenylbis(4-chlorophenyl)sulfonium hexafluoroantimonate, 4-(2-fluoro-4-benzoylphenylthio)phenylbis(4-chlorophenyl)sulfonium hexafluoroantimonate, 4-(2-methyl-4-benzoylphenylthio)phenylbis(4-chlorophenyl)sulfonium hexafluoroantimonate, 4-(2,3,5,6-tetramethyl-4-benzoylphenylthio)phenylbis(4-chlorophenyl)sulfonium hexafluoroantimonate, 4-(2,6-dichloro-4-benzoylphenylthio)phenylbis(4-chlorophenyl)sulfonium hexafluoroantimonate, 4-(2,6-dimethyl-4-benzoylphenylthio)phenylbis(4-chlorophenyl)sulfonium hexafluoroantimonate, 4-(2,3-dimethyl-4-benzoylphenylthio)phenylbis(4-chlorophenyl)sulfonium hexafluoroantimonate, 4-(2-chloro-4-acetylphenylthio)phenyldiphenylsulfonium hexafluoroantimonate, 4-(2-chloro-4-(4-methylbenzoyl)phenylthio)phenyldiphenylsulfonium hexafluoroantimonate, 4-(2-chloro-4-(4-fluorobenzoyl)phenylthio)phenyldiphenylsulfonium hexafluoroantimonate, 4-(2-chloro-4-(4-methoxybenzoyl)phenylthio)phenyldiphenylsulfonium hexafluoroantimonate, 4-(2-chloro-4-dodecanoylphenylthio)phenyldiphenylsulfonium hexafluoroantimonate, 4-(2-chloro-4-acetylphenylthio)phenylbis(4-fluorophenyl)sulfonium hexafluoroantimonate, 4-(2-chloro-4-(4-methylbenzoyl)phenylthio)phenylbis(4-fluorophenyl)sulfonium hexafluoroantimonate, 4-(2-chloro-4-(4-fluorobenzoyl)phenylthio)phenylbis(4-fluorophenyl)sulfonium hexafluoroantimonate, 4-(2-chloro-4-(4-methoxybenzoyl)phenylthio)phenylbis(4-fluorophenyl)sulfonium hexafluoroantimonate, 4-(2-chloro-4-dodecanoylphenylthio)phenylbis(4-fluorophenyl)sulfonium hexafluoroantimonate, 4-(2-chloro-4-acetylphenylthio)phenylbis(4-chlorophenyl)sulfonium hexafluoroantimonate, 4-(2-chloro-4-(4-methylbenzoyl)phenylthio)phenylbis(4-chlorophenyl)sulfonium hexafluoroantimonate, 4-(2-chloro-4-(4-fluorobenzoyl)phenylthio)phenylbis(4-chlorophenyl)sulfonium hexafluoroantimonate, 4-(2-chloro-4-(4-methoxybenzoyl)phenylthio)phenylbis(4-chlorophenyl)sulfonium hexafluoroantimonate, 4-(2-chloro-4- dodecanoylphenylthio)phenylbis(4-chlorophenyl)sulfonium hexafluoroantimonate, 4-(2-chloro-4-benzoylphenylthio) phenyldiphenylsulfonium hexafluorophosphate, 4-(2-chloro-4-benzoylphenylthio)phenyldiphenylsulfonium tetrafluoroborate, 4-(2-chloro-4-benzoylphenylthio) phenyldiphenylsulfonium perchlorate, 4-(2-chloro-4-benzoylphenylthio)phenyldiphenylsulfonium trifluoromethanesulfonate, 4-(2-chloro-4-benzoylphenyl-thio)phenylbis(4-fluorophenyl)sulfonium hexafluorophosphate, 4-(2-chloro-4-benzoylphenylthio)phenylbis(4-fluorophenyl)sulfonium tetrafluoroborate, 4-(2-chloro-4-benzoylphenylthio)phenylbis(4-fluorophenyl)sulfonium perchlorate, 4-(2-chloro-4-benzoylphenylthio)phenylbis(4-fluorophenyl)sulfonium trifluoromethanesulfonate, 4-(2-chloro-4-benzoylphenylthio)phenylbis(4-fluorophenyl)sulfonium p-toluenesulfonate, 4-(2-chloro-4-benzoylphenylthio)phenylbis(4-fluorophenyl)sulfonium camphorsulfonate, 4-(2-chloro-4-benzoylphenylthio)phe-nylbis(4-fluorophenyl)sulfonium nonafluorobutanesulfonate, 4-(2-chloro-4-benzoylphenylthio)phenylbis(4-chlorophenyl)sulfonium hexafluorophosphate, 4-(2-chloro-4-benzoylphenylthio)phenylbis(4-chlorophenyl)sulfonium tetrafluoroborate, 4-(2-chloro-4-benzoylphenylthio)phenyl-bis(4-chlorophenyl)sulfonium perchlorate, 4-(2-chloro-4-benzoylphenylthio)phenylbis(4-chlorophenyl)sulfonium trifluoromethanesulfonate, diphenyl[4-(phenylthio)phenyl] sulfonium trifluorotrispentafluoroethylphosphate, diphenyl [4-(p-terphenylthio)phenyl]sulfonium hexafluoroantimonate, diphenyl[4-(p-terphenylthio)phenyl] sulfonium trifluorotrispentafluoroethylphosphate and the like may be mentioned.

As other onium salt acid generating agents, for example, the cation portion of the general formula (t-1) may be replaced with, for example, sulfonium cations such as triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-ditert-butoxyphenyl) diphenylsulfonium, bis(3,4-ditert-butoxyphenyl) phenylsulfonium, tris(3,4-ditert-butoxyphenyl)sulfonium, diphenyl(4-thiophenoxyphenyl)sulfonium, (4-tert-butoxy-carbonylmethyloxyphenyl)diphenylsulfonium, tris(4-tert-butoxycarbonylmethyloxyphenyl)sulfonium, (4-tert-bu-toxyphenyl)bis(4-dimethylaminophenyl)sulfonium, tris(4-dimethylaminophenyl)sulfonium,
2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohex-ylcyclohexylmethylsulfonium, trinaphthylsulfonium, tribenzylsulfonium and the like; or iodinium cations such as aryl iodinium cations such as diphenyl iodinium, bis(4-tert-butylphenyl) iodinium, (4-tert-butoxyphenyl)phenyl iodinium, (4-methoxyphenyl)phenyl iodinium and the like may be mentioned.

As the oxime sulfonate acid generating agent, [2-(propyl-sulfonyloxyimino)-2,3-dihydrothiophene-3-ylidene](o-tolyl)acetonitrile, α-(p-toluenesulfonyloxyimino)-phenylac-etonitrile, α-(benzenesulfoniumoxyimino)-2,4-dichlorophenylacetonitrile, α-(benznenesulfonyloxyimino)-2,6-dichlorophenylacetonitrile, α-(2-chlorobenzenesulfonyloxyimino)-4-methoxyphenylacetonitrile, α-(ethylsulfonyloxyimino)-1-cyclopentenylacetonitrile, and the like may be mentioned.

Further, besides the above, the compounds represented by the following general formula (t-3) may be mentioned.

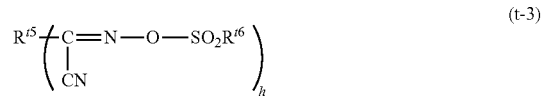

In the general formula (t-3), $R^{t5}$ represents a monovalent, divalent or trivalent organic group, $R^{t6}$ represents a substituted or unsubstituted saturated hydrocarbon group, unsaturated hydrocarbon group, or aromatic compound group, and h is an integer of 1 to 6.

As $R^{t5}$, an aromatic compound group is particularly preferable, and as such an aromatic compound group, an aromatic hydrocarbon group such as a phenyl group, naphthyl group and the like; or a heterocyclic group such as a furyl group, thienyl group or the like may be mentioned. These may have one or more suitable substituent group on the ring, for example, a halogen atom, alkyl group, alkoxy group, nitro group and the like. As $R^{t6}$, an alkyl group having 1 to 6 carbon atoms is particularly preferable, and a methyl group, ethyl group, propyl group, and butyl group may be mentioned. Further, h is preferably an integer of 1 to 3, and 1 or 2 is more preferable.

As the photoacid generating agent represented by the general formula (t-3), when h=1, compounds where $R^{t5}$ is any one of a phenyl group, methylphenyl group, and methoxyphenyl group, and where $R^{t6}$ is a methyl group may be mentioned. More specifically, as the photoacid generating agent represented by the general formula (t-3), α-(methyl-sulfonyloxyimino)-1-phenylacetonitrile, α-(methylsulfony-loxyimino)-1-(p-methylphenyl)acetonitrile, and α-(methyl-sulfonyloxyimino)-1-(p-methoxyphenyl)acetonitrile may be mentioned.

As the photoacid generating agent represented by the general formula (t-3), when h=2, the photoacid generating agents represented by the following formula may be mentioned.

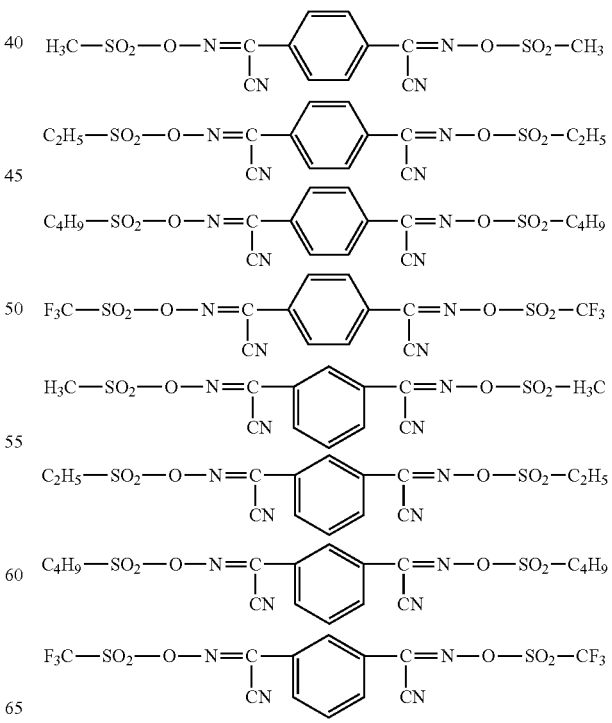

As the halogen group-containing triazine compound, halogen-containing compounds such as 2,4-bis(trichloromethyl)-6-piperonyl-1,3,5-triazine, 2,4-bis(trichloromethyl)-6-[2-(2-furyl)ethenyl]-s-triazine, 2,4-bis(trichloromethyl)-6-[2-(5-methyl-2-furyl)ethenyl]-s-triazine, 2,4-bis(trichloromethyl)-6-[2-(5-ethyl-2-furyl)ethenyl]-s-triazine, 2,4-bis(trichloromethyl)-6-[2-(5-propyl-2-furyl)ethenyl]-s-triazine, 2,4-bis(trichloromethyl)-6-[2-(3,5-dimethoxyphenyl)ethenyl]-s-triazine, 2,4-bis(trichloromethyl)-6-[2-(3,5-diethoxyphenyl)ethenyl]-s-triazine, 2,4-bis(trichloromethyl)-6-[2-(3,5-dipropoxyphenyl)ethenyl]-s-triazine, 2,4-bis(trichloromethyl)-6-[2-(3-methoxy-5-ethoxyphenyl)ethenyl]-s-triazine, 2,4-bis(trichloromethyl)-6-[2-(3-methoxy-5-propoxyphenyl)ethenyl]-s-triazine, 2,4-bis(trichloromethyl)-6-[2-(3,4-methylenedioxyphenyl) ethenyl]-s-triazine, 2,4-bis(trichloromethyl)-6-(3,4-methylenedioxyphenyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(2-bromo-4-methoxy)styrylphenyl-s-triazine, 2,4-bis-trichloromethyl-6-(3-bromo-4-methoxy)styrylphenyl-s-triazine, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis(trichloromethyl)-1,3,5-triazine, tris(1,3-dibromopropyl)-1,3,5-triazine, tris(2,3-dibromopropyl)-1,3,5-triazine and the like; and halogen-containing triazine compounds represented by the following general formula (t-4) such as tris(2,3-dibromopropyl)isocyanurate and the like, may be mentioned.

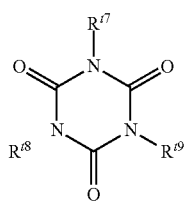

(t-4)

In the general formula (t-4), $R^{t7}$, $R^{t8}$, and $R^{t9}$ respectively and independently represent halogenated alkyl groups with 1 to 6 carbon atoms.

Further, as other photoacid generating agents, bissulfonyldiazomethanes such as bis(p-toluenesulfonyl)diazomethane, methylsulfonyl-p-toluenesulfonyldiazomethane, 1-cyclohexylsulfonyl-1-(1,1-dimethylethylsulfonyl)diazomethane, bis(1,1-dimethylethylsulfonyl)diazomethane, bis(1-methylethylsulfonyl)diazomethane, bis(cyclohexylsulfonyl)diazomethane, bis(2,4-dimethylphenylsulfonyl)diazomethane, bis(4-ethylphenylsulfonyl)diazomethane, bis(3-methylphenylsulfonyl)diazomethane, bis(4-methoxyphenylsulfonyl)diazomethane, bis(4-fluorophenylsulfonyl)diazomethane, bis(4-chlorophenylsulfonyl)diazomethane, and bis(4-tert-butylphenylsulfonyl)diazomethane; sulfonylcarbonylalkanes such as 2-methyl-2-(p-toluenesulfonyl)propiophenone, 2-(cyclohexylcarbonyl)-2-(p-toluenesulfonyl)propane, 2-methanesulfonyl-2-methyl-(p-methylthio)propiophenone, and 2,4-dimethyl-2-(p-toluenesulfonyl)pentane-3-one; sulfonylcarbonyldiazomethanes such as 1-p-toluenesulfonyl-1-cyclohexylcarbonyldiazomethane, 1-diazo-1-methylsulfonyl-4-phenyl-2-butanone, 1-cyclohexylsulfonyl-1-cyclohexylcarbonyldiazomethane, 1-diazo-1-cyclohexylsulfonyl-3,3-dimethyl-2-butanone, 1-diazo-1-(1,1-dimethylethylsulfonyl)-3,3-dimethyl-2-butanone, 1-acetyl-1-(1-methylethylsulfonyl)diazomethane, 1-diazo-1-(p-toluenesulfonyl)-3,3-dimethyl-2-butanone, 1-diazo-1-benzenesulfonyl-3,3-dimethyl-2-butanone, 1-diazo-1-(p-toluenesulfonyl)-3-methyl-2-butanone, cyclohexyl 2-diazo-2-(p-toluenesulfonyl)acetate, tert-butyl 2-diazo-2-benzenesulfonylacetate, isopropyl 2-diazo-2-methanesulfonylacetate, cyclohexyl 2-diazo-2-benznesulfonylacetate, and tert-butyl 2-diazo-2-(p-toluenesulfonyl)acetate; nitrobenzyl derivatives such as 2-nitrobenzyl p-toluenesulfonate, 2,6-dinitrobenzyl p-toluenesulfonate, and 2,4-dinitrobenzyl p-trifluoromethylbenzenesulfonate; esters of polyhydroxy compounds and aliphatic or aromatic sulfonic acids such as methanesulfonic acid ester of pyrogallol, benzenesulfonic acid ester of pyrogallol, p-toluenesulfonic acid ester of pyrogallol, p-methoxybenznesulfonic acid ester of pyrogallol, mesitylenesulfonic acid ester of pyrogallol, benzylsulfonic acid ester of pyrogallol, methanesulfonic acid ester of alkyl gallate, benzenesulfonic acid ester of alkyl gallate, p-toluenesulfonic acid ester of alkyl gallate, p-methoxybenzenesulfonic acid ester of alkyl gallate (the alkyl group has 1 to 15 carbon atoms), mesitylenesulfonic acid ester of alkyl gallate, and benzylsulfonic acid ester of alkyl gallate; and the like may be mentioned.

These photoacid generating agents may be used alone or in combinations of two or more kinds thereof.

The content of the photoacid generating agent is preferably from 0.05 to 30 parts by mass with respect to 100 parts by mass of the alkali-soluble resin having a phenolic hydroxyl group, and more preferably 0.1 to 10 parts by mass. With the above range, the curing properties of the composition of the second embodiment become favorable.

As described above, the composition of the second embodiment comprises a compound represented by the general formula (1), a compound represented by the general formula (10), and/or a compound represented by the general formula (19). Cured products having a high hardness can easily be obtained from the composition containing this compound. Further, when this compound is incorporated in a negative-type photosensitive resin composition, good micropatterning properties can be obtained.

The content of the compound represented by the general formula (1), the compound represented by the general formula (10) and/or the compound represented by the general formula (19) is preferably 1 to 80% by mass, more preferably 3 to 65% by mass, further preferably 5 to 50% by mass, relative to the solid content of the composition of the second embodiment. A content in the above-defined range is advantageous in that an improvement in coating film forming capability and curability of the composition of the second embodiment can easily be realized and, when the composition of the second embodiment is a negative-type photosensitive resin composition, good micropatterning properties can be provided while realizing good developability.

The composition of the second embodiment may also further comprise a compound with a molecular weight of less than 2000 and having 4 or more phenolic hydroxyl groups.

As such compounds, specifically, in addition to benzophenone compounds such as various types of tetrahydroxybenzophenones, pentahydroxybenzophenones, hexahydroxybenzophenones, heptahydroxybenzophenones and the like; hydroxyaryl compounds such as bis[2-hydroxy-3-(2'-hydroxy-5'-methylbenzyl)-5-methylphenyl]methane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3,5-dimethylphenyl)-2,4-dihydroxyphenylmethane, bis(4-hydroxy-2,5-dimethylphenyl)-2,4-dihydroxyphenylmethane, bis(3-cyclohexyl-4-hydroxy-6-methylphenyl)-3,4-dihydroxyphenylmethane, bis(3-cyclohexyl-6-hydroxy-4-methylphenyl)-3,4-dihydroxyphenylmethane, bis(4-hydroxy-2,3,5-trimethylphenyl)-3,4-dihydroxyphenylmethane and the like; bis(hydroxyphenyl)alkane compounds such as 2-(2,3,4-trihydroxyphenyl)-2-(2',3',4'-trihydroxyphenyl)propane, 2-(2,4-dihydroxyphenyl)-2-(2',4'-dihydroxyphenyl)propane and the like; polyhydroxystyrene compounds with a molecular weight less than 2000 such as poly(o-hydroxystyrene), poly(m-hydroxystyrene), poly(p-hydroxystyrene), poly(α-methyl-p-hydroxystyrene), poly(4-hydroxy-3-methylstyrene) and the like; and the like may be mentioned. These benzophenone compounds, hydroxyaryl compounds, bis(hydroxyphenyl)alkane compounds, and polyhydroxystearene compounds may have a substituent group other than a hydroxyl group.

These compounds may be used alone or in combinations of two or more kinds thereof.

The content of compounds that contain four or more phenolic hydroxyl groups and have a molecular weight of less than 2000 is preferably 0.5 to 5 parts by mass relative to 100 parts by mass of the alkali-soluble resin containing a phenolic hydroxyl group. When the composition of the second embodiment is a negative-type photosensitive resin composition, the content in the above-defined range is advantageous in that a tapering phenomenon in patterning of the composition of the second embodiment can be suppressed.

Organic solvents exemplified in the composition of the first embodiment may be mentioned as organic solvents usable in the composition of the second embodiment.

The content of the organic solvent is such that the solid content concentration of the composition of the second embodiment is preferably 1 to 50% by mass, more preferably 5 to 30% by mass.

(3) Composition of Third Embodiment

The composition of the third embodiment is a negative-type photosensitive resin composition comprising a photosensitive polyimide precursor, a photopolymerizable monomer, a photopolymerization initiator, a compound represented by the general formula (1), a compound represented by the general formula (10), and a compound represented by the general formula (19). The composition of the third embodiment may further contain an organic solvent.

For example, a photosensitive polyimide precursor comprising a constituent unit represented by the following general formula (u-1) and containing an acid functional group and a photosensitive group in its molecule may be used as the photosensitive polyimide precursor in the composition of the third embodiment.

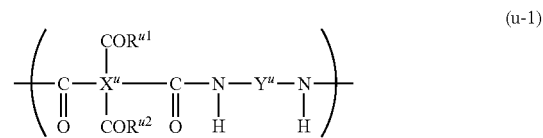

In the general formula (u-1), $X^u$ represents a tetravalent organic group free from an atom having an unshared electron pair in a skeleton connecting two amide groups bonded to $X^u$; $Y^u$ represents a divalent organic group free from an atom having an unshared electron pair in a skeleton connecting two amide groups bonded to $Y^u$; and $R^{u1}$ and $R^{u2}$ each independently represent a hydroxyl group or a monovalent organic group.

In the definitions of $X^u$ and $Y^u$, the "skeleton connecting two amide groups" means a skeleton consisting only of atoms constituting a chain of bonds binding the two amide bonds. Accordingly, atoms which are present as terminals such as hydrogen atoms and fluorine atoms and the like, which do not form the chain of bonds connecting the two amide bonds, are not included in the above "skeleton". However, in the case of including atoms which constitute a ring (aromatic ring or aliphatic ring) in this skeleton, all of the atoms constituting this ring are considered to be included in the above "skeleton". For example, in the case of including a benzene ring or a cyclohexyl ring, the 6 carbon atoms constituting the benzene ring or cyclohexyl ring itself are considered to be included in the above "skeleton". Further, substituent groups or hydrogen atoms bonded to the benzene ring or cyclohexyl ring are not included in the "skeleton".

Accordingly, in the case that a carbonyl bond is present on the skeleton, what constitutes the chain connecting the above two amide groups is only the carbon atom of the carbonyl group, thus the oxygen atom of the carbonyl group is not considered to be a constituent of the above "skeleton". Further, concerning a 2,2-propylidene bond or a hexafluoro-2,2-propylidene bond, only the carbon atom present in the center (2-position) is considered to constitute the skeleton, and the carbon atoms at both ends (the 1- and 3-positions) are not considered to constitute the above "skeleton". As an example of an "atom having an unshared electron pair", an oxygen atom, nitrogen atom, sulfur atom and the like may be mentioned; on the other hand, as an "atom not having an unshared electron pair", a carbon atom and a silicon atom and the like may be mentioned.

In the photosensitive polyimide precursor, when $X^u$ does not contain an atom having an unshared electron pair in the skeleton as described above, the swelling when alkali-developing is small and thus is preferable. For the same reason, it is preferable that $Y^u$ does not contain an atom having an unshared electron pair in the skeleton.

Further, in the photosensitive polyimide precursor, instead of having $Y^u$ in the constituent units, one having $Y^{u2}$ which has silicon atoms as a part thereof; for example, one having a siloxane bond, is preferable because a higher substrate adhesion can be imparted. In this case, the proportion thereof is preferably 1 to 20 mol % among all of the diamine residues forming the photosensitive polyimide precursor.

As the $X^u$ and $Y^u$ in the general formula (u-1), an alkyl group or cycloalkyl group with 4 to 20 carbon atoms, or an aromatic ring such as a benzene ring or a naphthyl ring, with 6 to 20 carbon atoms or the like, or ones where 2 to 10 of these aromatic rings are bonded via a single bond, alkylene group, fluorinated alkylene group, carbonyl group or the like may be mentioned as preferable. Further, these may have a substituent group such as a hydrocarbon group, halogenated hydrocarbon group, halogen atom or the like on the aromatic ring. Further, among the $X^u$ and $Y^u$, those where the atoms directly bonded to the atoms constituting the above described skeleton are also "atoms not having unshared electron pairs" and have a higher effect and are preferable. Further, in this definition, those where a carbon atom constituting the skeleton is directly bonded to an oxygen atom, such as a carbonyl group, or those where a fluorine atom is bonded to a carbon atom constituting the skeleton, are excluded. Furthermore, $X^u$ and $Y^u$ preferably do not include a fluorine atom.

As the acid functional group included in the molecule of the photosensitive polyimide precursor, a carboxyl group, phenolic hydroxyl group, sulfonic acid group and the like may be mentioned, and among these a carboxyl group is preferable. Further, as the photosensitive group, a vinyl group, aryl group, acrylolyl group, methacrylolyl group, acryloxy group, methacryloxy group and the like comprising an ethylenic unsaturated bond are preferable, and among these, an acrylolyl group, methacrylolyl group, acryloxy group, and methacryloxy group are preferable.

In the photosensitive polyimide precursor, the acid functional group is preferably one in which $R^{u1}$ or $R^{u1}$ in the constituent unit of the general formula (u-1) represents a hydroxyl group (that is, forming a carboxyl group) or is present in a diamine residue represented by $Y^u$. The photosensitive group is preferably present in a side chain represented by $R^{u1}$ or $R^{u2}$ in the general formula (u-1), or in a diamine residue represented by $Y^u$, for example, as a group bonded to an aromatic ring in a diamine residue containing an aromatic ring.

In $R^{u1}$ and $R^{u2}$, examples of the monovalent organic group containing a photosensitive group may be those represented by the following general formula.

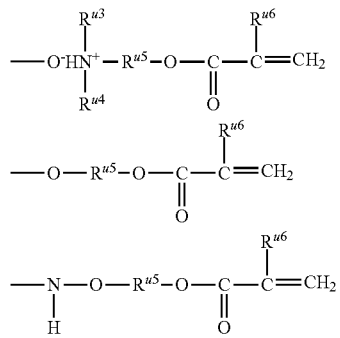

$R^{u3}$ and $R^{u4}$ in the general formula each independently represent a monovalent hydrocarbon group having 1 to 6 carbon atoms, $R^{u5}$ represents a divalent hydrocarbon group having 1 to 10 carbon atoms, and $R^{u6}$ represents a hydrogen atom or a methyl group.

Further, in $R^{u1}$ and $R^{u2}$, an alkoxy or alkylamino group having 1 to 15 carbon atoms may be mentioned as the monovalent organic group free from the photosensitive group.

The photosensitive polyimide precursor preferably contains 50 to 100% by mole of a constituent unit represented by the general formula (u-1). More preferably, the photosensitive polyimide precursor consists of a constituent unit represented by the general formula (u-1) only, or comprises a constituent unit represented by the general formula (u-1) and a constituent unit that is the same as the constituent unit represented by the general formula (u-1) except that $Y^u$ in the general formula (u-1) represents a divalent organic group containing a silicon atom.

For the photosensitive polyimide precursor, it is possible to obtain as ingredients a tetracarboxylic dianhydride, a diamine, and a compound having a photosensitive group, and various known production methods may be applied.

As a tetracarboxylic dianhydride, as one providing $X^u$, for example, pyromellitic dianhydride, 3,3',4,4'-biphenyltetracarboxylic dianhydride, 1,2,5,6-naphthalenetetracaroxylic dianhydride, 2,3,6,7-naphthalenetetracaroxylic dianhydride, 1,4,5,8-naphthalenetetracaroxylic dianhydride, 3,4,9,10-perylenetetracarboxylic dianhydride, m-terphenyl-3,3',4,4'-tetracaroxylic dianhydride, p-terphenyl-3,3',4,4'-tetracaroxylic dianhydride, 4,4'-hexafluoroisopropylidenediphthalic dianhydride, 3,3',4,4'-benzophenonetetracaroxylic dianhydride and the like may be mentioned. These tetracarboxylic dianhydrides may be used alone or in combinations of two or more kinds thereof.

As the diamine, as one for providing $Y^u$, for example, 2,2'-dimethyl-4,4'-diaminobiphenyl, 3,3'-dimethyl-4,4'-diaminobiphenyl, 2,2',6,6'-tetramethyl-4,4'-diaminobiphenyl, 3,3',5,5'-tetramethyl-4,4'diaminobiphenyl, 4,4'-(or 3,4-, 3,3'-, 2,4-, 2,2'-)diaminodiphenylmethane, p-xylylenediamine, m-xylylenediamine, 4,4'-methylene-bis-(2,6-diethylaniline), 4,4'-methylene-bis-(2,6-diisopropylaniline), 1,5-diaminonaphthalene, 3,3'-dimethyl-4,4'-diaminodiphenylmethane, 3,3',5,5'-tetramethyl-4,4'-diaminodiphenylmethane, 2,2-bis(4-aminophenyl)propane, 2,2'-hexafluorodimethyl-4,4'-diaminobiphenyl, 3,3'-hexafluorodimethyl-4,4'-diaminobiphenyl, 4,4'-hexafluoroisopropylidenedianiline, 1,1,1,3,3,3-hexafluoro-2,2-bis(4-aminophenyl)propane, 2,3,5,6-tetramethyl-1,4-phenylenediamine, 2,5-dimethyl-1,4-phenylenediamine, 2,4-diaminotoluene, 2,6-diaminotoluene, 2,4,6-trimethyl-1,3-phenylenediamine, 2,7-diaminofluorene, 4,4-diaminooctafluorobiphenyl, 2,2-hexafluorodimethyl-4,4'-diaminobiphenyl and the may be mentioned as preferable, and these diamines may be used alone or in combinations of two or more kinds thereof.

Further, for a bifunctional amine not including an atom having an unshared electron pair at the skeleton connecting the amino group, $Y^u$ may have at least one phenolic hydroxyl group or carboxyl group as an acid functional group. For example, 2,5-diaminobenzoic acid, 3,4-diaminobenzoic acid, 3,5-diaminobenzoic acid, 2,5-diaminoterephthalic acid, bis(4-amino-3-carboxyphenol)methylene, 4,4'-diamino-3,3'-dicarboxybiphenyl, 4,4'-diamino-5,5'-dicarboxy-2,2'-dimethylbiphenyl, 1,3-diamino-4-hydroxybenzene, 1,3-diamino-5-hydroxybenzene, 3,3'-diamino-4,4'-dihydroxybiphenyl, 4,4'-diamino-3,3'-dihydroxybiphenyl, bis(3-amino-4-hydroxyphenyl)hexafluoropropane, bis(4-amino-3-hydroxyphenyl)hexafluoropropane, bis(4-amino-3-carboxyphenyl)methane, 4,4'-diamino-2,2'-dicarboxybiphenyl and the like may be mentioned as being preferable. These may be used alone or in combinations of two or more kinds thereof together with diamines.

Further, as one providing a $Y^{u2}$ including a silicon atom, an aliphatic diamine such as the diaminopolysiloxanes represented by the following general formula (u-2) may be mentioned.

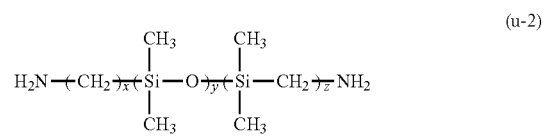

In the general formula (u-2), x, y, and z respectively and independently represent integers from 1 to 10.

In the case of using such an aliphatic diamine, from the viewpoint that swelling when developing is low and the heat resistance of the film when forming the film and the like, it is preferable that its content is 20 mol % or less of the whole diamine.

For making the polyimide precursor having the photosensitive group, a method of making the polyimide precursor wherein a compound having an ethylenically unsaturated bond and an amino group or a quaternary salt group thereof, is provided in a form where a part of the amino group or quaternary salt group thereof is ionically bonded with a carboxylic group of a polyamic acid, or a method of introducing an ethylenically unsaturated bond at a side chain via a shared bond such as an ester bond, amide bond or the like may be mentioned.

Among these, in particular, a photosensitive polyimide precursor (polyamic ester) of a form where an ethylenically unsaturated bond is introduced by an ester bond, is suitable for alkali developing. In the case of introducing the ethylenically unsaturated bond by an ester bond, the introduced amount of the compound having the ethylenically unsaturated bond, from the viewpoint making the alkali solubility, curing properties, heat resistance and the like compatible with the reactivity, is preferably an amount of 85 to 25 mol % with respect to the total amount of the carboxyl groups belonging to the polyamic acid, and the remainder is left as carboxyl groups (namely, a polyamic partial ester).

As examples of the compound introducing ethylenically unsaturated bonds by an ester bond, 2-hydroxyethyl acrylate, 3-hydroxypropyl acrylate, 2-hydroxyethyl methacrylate, 3-hydroxypropyl methacrylate, 4-hydroxybutyl acrylate, 4-hydroxybutyl methacrylate, pentaerythritol diacrylate monostearate, pentaerythritol triacrylate, pentaerythritol trimethacrylate, caprolactone 2-(methacryloyloxy)ethyl ester, dicaprolactone 2-(methacryloyloxy)ethyl ester, caprolactone 2-(acryloyloxy)ethyl ester, dicaprolactone 2-(acryloyloxy)ethyl ester and the like may be mentioned.

The mass average molecular weight of the photosensitive polyimide precursor is preferably 5000 to 80000.

The content of the photosensitive polyimide precursor is preferably 4 to 95% by mass, more preferably 55 to 90% by mass, relative to the solid content of the composition of the third embodiment. The content in the above-defined range is advantageous in that a good balance of developability can easily be realized.

Examples of photopolymerizable monomers in the composition of the third embodiment include those exemplified in the composition of the first embodiment.

The content of the photopolymerizable monomer is preferably 5 to 100 parts by mass, more preferably 5 to 40 parts by mass, relative to 100 parts by mass of the photosensitive polyimide precursor. The content in the above-defined range is advantageous in that a good balance of sensitivity, developability, and resolution can easily be realized.

Examples of photopolymerization initiators in the composition of the third embodiment include those exemplified in the composition of the first embodiment.

The content of the photopolymerization initiator is preferably 0.01 to 40 parts by mass relative to 100 parts by mass of the photosensitive polyimide precursor. The content in the above-defined range is advantageous in that satisfactory heat resistance and chemical resistance can be provided, an improvement in coating film forming capability can be realized, and failure to cure can be suppressed.

As described above, the composition of the third embodiment comprises a compound represented by the general formula (1), a compound represented by the general formula (10) and/or a compound represented by the general formula (19). Cured products having a high hardness can easily be obtained from the composition containing this compound. Further, when this compound is incorporated in a negative-type photosensitive resin composition, good micropatterning properties can be realized.

The content of the compound represented by the general formula (1), the compound represented by the general formula (10) and/or the compound represented by the general formula (19) is preferably 0.5 to 50% by mass, more preferably 1 to 20% by mass, relative to the above solid content. The content in the above-defined range is advantageous in that an improvement in coating film forming capability and curability of the composition of the third embodiment can easily be realized and good micropatterning properties can be provided while realizing good developability.

Organic solvents in the composition of the third embodiment may be those exemplified in the composition of the first embodiment. Among these, polar solvents which completely dissolve the generated polyimide are preferable. As such polar solvents, N-methyl-2-pyrrolidone, N,N-dimethyl acetamide, N,N-dimethyl formamide, dimethyl sulfoxide, tetramethyl urea, hexamethylphosphoric triamide, γ-butyl lactone and the like may be mentioned.

The content of the organic solvent is preferably an amount such that the solid content concentration of the composition of the third embodiment is 1 to 50 mass %, and more preferably an amount such that the solid content concentration is 5 to 30 mass %.

(4) Composition of Fourth Embodiment

The composition of the fourth embodiment comprises a polyimide precursor, a compound represented by the general formula (1), a compound represented by the general formula (10), and/or a compound represented by the general formula (19). The composition of the fourth embodiment may further contain a photobase generating agent and/or an organic solvent. When the composition of the fourth embodiment does not contain a photobase generating agent, the composition is a non-photosensitive resin composition. On the other hand, when the composition contains a photobase generating agent, the composition is photosensitive.

When the composition of the fourth embodiment is photosensitive, a specific example thereof is a negative-type photosensitive resin composition comprising a polyimide precursor, a photobase generating agent, a compound represented by the general formula (1), a compound represented by the general formula (10) and/or a compound represented by the general formula (19). The negative-type photosensitive resin composition may further contain an organic solvent.

For example, polyamic acids containing a constituent unit represented by the following general formula (v-1) may be used as the polyimide precursor in the composition of the fourth embodiment.

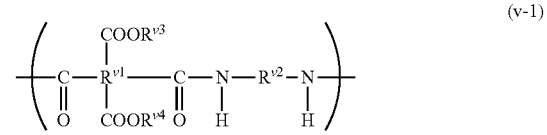

(v-1)

In the general formula (v-1), $R^{v1}$ represents a tetravalent organic group, $R^{v2}$ represents a divalent organic group, and $R^{v3}$ and $R^{v4}$ represent a hydrogen atom or a monovalent organic group.

In the case that $R^{v3}$ and $R^{v4}$ are monovalent organic groups, for example, an alkyl group, alkenyl group, alkynyl group, aryl group, or a structure where an ester bond is included with these groups represented by $C_iH_{2i}OC_jH_{2j+1}$ and the like, and the like may be mentioned.

As the polyimide precursor, a polyamic acid such that $R^{v3}$ and $R^{v4}$ are hydrogen atoms is suitable from the point of alkali developability.

Further, the tetravalence of $R^{v1}$ represents only a valence number for bonding with acids, but it may have further functional groups. In the same way, the divalence of $R^{v2}$ represents only a valence number for bonding with amines, but it may have further functional groups.

The polyamic acid can be obtained by reacting an acid dianhydride and a diamine, but from the viewpoint of imparting excellent heat resistance and dimensional stability to the finally obtained polyimide, in the general formula (v-1), it is preferable for $R^{v1}$ or $R^{v2}$ to be an aromatic group, and more preferable for $R^{v1}$ and $R^{v2}$ to be aromatic groups. In this case, in $R^{v1}$ of the general formula (v-1), the four groups ((—CO—)$_2$(—COOH)$_2$) bonded to this $R^{v1}$ may be bonded to the same aromatic ring, or may be bonded to different aromatic rings. In the same way, in $R^{v2}$ of the general formula (v-1), the two groups ((—NH—)$_2$) bonded to this $R^{v2}$ may be bonded to the same aromatic ring, or may be bonded to different aromatic rings.

The polyamic acid represented by the general formula (v-1) may consist of a single constituent unit, or may consist of 2 or more repeating units.

As the method of producing the polyimide precursor, a conventionally known process may be applied. For example, (1) a process of synthesizing a polyamic acid which is a precursor from an acid dianhydride and a diamine; (2) a process of synthesizing a polyamide precursor by reacting a diamino compound or its derivative at a carboxylic acid of an ester acid or amic acid monomer which are synthesized by reacting a primary alcohol, amino compound, epoxy compound or the like with an acid dianhydride; and the like may be mentioned.

As the acid dianhydride applicable to the reaction for obtaining the polyimide precursor, aliphatic tetracarboxylic acid dianhydrides such as ethylenetetracarboxylic acid dianhydride, butanetetracarboxylic acid dianhydride, cyclobutanetetracarboxylic acid dianhydride, methylcyclobutanetetracarboxylic acid dianhydride, and cyclopentanetetracarboxylic acid dianhydride; aromatic tetracarboxylic acid dianhydrides such as pyromellitic dianhydride, 3,3',4,4'-benzophenonetetracarboxylic acid dianhydride, 2,2',3,3'-benzophenonetetracarboxylic acid dianhydride, 2,3',3,4'-benzophenonetetracarboxylic acid dianhydride, 3,3',4,4'-biphenyltetracarboxylic acid dianhydride, 2,2',3,3'-biphenyltetracarboxylic acid dianhydride, 2,3',3,4'-biphenyltetracarboxylic acid dianhydride, 2,2',6,6'-biphenyltetracarboxylic acid dianhydride, 2,2-bis(3,4-dicarboxyphenyl)propane dianhydride, 2,2-bis(2,3-dicarboxyphenyl)propane dianhydride, bis(3,4-dicarboxyphenyl)ether dianhydride, bis(3,4-dicarboxyphenyl)sulphone dianhydride, 1,1-bis(2,3-dicarboxyphenyl)ethane dianhydride, bis(2,3-dicarboxyphenyl)methane dianhydride, bis(3,4-dicarboxyphenyl)methane dianhydride, 2,2-bis(3,4-dicarboxyphenyl)-1,1,1,3,3,3-hexafluoroproane dianhydride, 2,2-bis(2,3-dicarboxyphenyl)-1,1,1,3,3,3-hexafluoroproane dianhydride, 1,3-bis[(3,4-dicarboxy)benzoyl]benzene dianhydride, 1,4-bis[(3,4-dicarboxy)benzoyl]benzene dianhydride, 2,2-bis{4-[4-(1,2-dicarboxy)phenoxy]phenyl}propane dianhydride, 2,2-bis{4-[3-(1,2-dicarboxy)phenoxy]phenyl}propane dianhydride, bis{4-[4-(1,2-dicarboxy)phenoxy]phenyl}ketone dianhydride, bis{4-[3-(1,2-dicarboxy)phenoxy]phenyl}ketone dianhydride, 4,4'-bis[4-(1,2-dicarboxy)phenoxy]biphenyl dianhydride, 4,4'-bis[3-(1,2-dicarboxy)phenoxy]biphenyl dianhydride, bis{4-[4-(1,2-dicarboxy)phenoxy]phenyl}ketone dianhydride, bis{4-[3-(1,2-dicarboxy)phenoxy]phenyl}ketone dianhydride, bis{4-[4-(1,2-dicarboxy)phenoxy]phenyl}sulfone dianhydride, bis{4-[3-(1,2-dicarboxy)phenoxy]phenyl}sulfone dianhydride, bis{4-[4-(1,2-dicarboxy)phenoxy]phenyl}sulfide dianhydride, bis{4-[3-(1,2-dicarboxy)phenoxy]phenyl}sulfide dianhydride, 2,2-bis{4-[4-(1,2-dicarboxy)phenoxy]phenyl}-1,1,1,3,3,3-hexafluoroproane dianhydride, 2,2-bis{4-[3-(1,2-dicarboxy)phenoxy]phenyl}-1,1,1,3,3,3-hexafluoroproane dianhydride, 2,3,6,7-naphthalenetetracarboxylic dianhydride, 1,1,1,3,3,3-hexafluoro-2,2-bis(2,3- or 3,4-dicarboxyphenyl)propane dianhydride, 1,4,5,8-naphthalenetetracarboxylic dianhydride, 1,2,5,6-naphthalenetetracarboxylic dianhydride, 1,2,3,4-benzenetetracarboxylic dianhydride, 3,4,9,10-perylenetetracarboxylic dianhydride, 2,3,6,7-anthracenetetracarboxylic dianhydride, 1,2,7,8-phenanthrenetetracarboxylic dianhydride, pyridinetetracarboxylic dianhydride, sulfonyldiphthalic acid anhydride, m-terphenyl-3,3',4,4'-tetracarboxylic dianhydride, and p-terphenyl-3,3',4,4'-tetracarboxylic dianhydride may be mentioned.

These acid dianhydrides may be used alone or in combinations of two or more kinds thereof.

As the diamine applicable to the reaction for obtaining the polyimide precursor, for example, aromatic amines such as p-phenyline diamine, m-phenyline diamine, o-phenyline diamine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenyl sulfone, 3,4'-diaminodiphenyl sulfone, 4,4'-diaminodiphenyl sulfone, 3,3'-diaminobenzophenone, 4,4'-diaminobenzophenone, 3,4'-diaminobenzophenone, 3,3'-diaminodiphenylmethane, 4,4'-diaminodiphenylmethane, 3,4'-diaminodiphenylmethane, 2,2-di(3-aminophenyl)propane, 2,2-di(4-aminophenyl)propane, 2-(3-aminophenyl)-2-(4-aminophenyl)propane, 2,2-di(3-aminophenyl)-1,1,1,3,3,3-hexafluoropropane, 2,2-di(4-aminophenyl)-1,1,1,3,3,3-hexafluoropropane, 2-(3-aminophenyl)-2-(4-aminophenyl)-1,1,1,3,3,3-hexafluoropropane, 1,1-di(3-aminophenyl)-1-phenylethane, 1,1-di(4-aminophenyl)-1-phenylethane, 1-(3-aminophenyl)-1-(4-aminophenyl)-1-phenylethane, 1,3-bis(3-aminophenoxy)benzene, 1,3-bis(4-aminophenoxy)benzene, 1,4-bis(3-aminophenoxy)benzene, 1,4-bis(4-aminophenoxy)benzene, 1,3-bis(3-aminobenzoyl)benzene, 1,3-bis(4-aminobenzoyl)benzene, 1,4-bis(3-aminobenzoyl)benzene, 1,4-bis(4-aminobenzoyl)benzene, 1,3-bis(3-amino-α,α-dimethylbenzyl)benzene, 1,3-bis(4-amino-α,α-dimethylbenzyl)benzene, 1,4-bis(3-amino-α,α-dimethylbenzyl)benzene, 1,4-bis(4-amino-α,α-dimethylbenzyl)benzene, 1,3-bis(3-amino-α,α-ditrifluoromethylbenzyl)benzene, 1,3-bis(4-amino-α,α-ditrifluoromethylbenzyl)benzene, 1,4-bis(3-amino-α,α-ditrifluoromethylbenzyl)benzene, 1,4-bis(4-amino-α,α-ditrifluoromethylbenzyl)benzene, 2,6-bis(3-aminophenoxy)benzonitrile, 2,6-bis(3-aminophenoxy)pyridine, 4,4'-bis(3-aminophenoxy)biphenyl, 4,4'-bis(4-aminophenoxy)biphenyl, bis[4-(3-aminophenoxy)phenyl]ketone, bis[4-(4-aminophenoxy)phenyl]ketone, bis[4-(3-aminophenoxy)

phenyl]sulfide, bis[4-(4-aminophenoxy)phenyl]sulfide, bis [4-(3-aminophenoxy)phenyl]sulfone, bis[4-(4-aminophenoxy)phenyl]sulfone, bis[4-(3-aminophenoxy) phenyl]ether, bis[4-(4-aminophenoxy)phenyl]ether, 2,2-bis [4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoro propane, 2,2-bis[4-(4-aminophenoxy)phenyl]-1,1,1,3,3,3-hexafluoro propane, 1,3-bis[4-(3-aminophenoxy)benzoyl]benzene, 1,3-bis[4-(4-aminophenoxy)benzoyl]benzene, 1,4-bis[4-(3-aminophenoxy)benzoyl]benzene, 1,4-bis[4-(4-aminophenoxy)benzoyl]benzene, 1,3-bis[4-(3-aminophenoxy)-α,α-dimethylbenzyl]benzene, 1,3-bis[4-(4-aminophenoxy)-α,α-dimethylbenzyl]benzene, 1,4-bis[4-(3-aminophenoxy)-α,α-dimethylbenzyl]benzene, 1,4-bis[4-(4-aminophenoxy)-α,α-dimethylbenzyl]benzene, 4,4'-bis[4-(4-aminophenoxy) benzoyl]diphenyl ether, 4,4'-bis[4-(4-amino-α,α-dimethylbenzyl)phenoxy]benzophenone, 4,4'-bis[4-(4-amino-α,α-dimethylbenzyl)phenoxy]diphenyl sulfone, 4,4'-bis[4-(4-aminophenoxy)phenoxy]diphenyl sulfone, 3,3'-diamino-4,4'-diphenoxybenzophenone, 3,3'-diamino-4,4'-dibiphenoxybenzophenone, 3,3'-diamino-4-phenoxybenzophenone, 3,3'-diamino-4-biphenoxybenzophenone, 6,6'-bis(3-aminophenoxy)-3,3,3', 3'-tetramethyl-1,1'-spirobiindan, and 6,6'-bis(4-aminophenoxy)-3,3,3',3'-tetramethyl-1,1'-spirobiindan; aliphatic amines such as 1,3-bis(3-aminopropyl)tetramethyldisiloxane, 1,3-bis(4-aminobutyl)tetramethyldisiloxane, α,ω-bis(3-aminopropyl)polydimethylsiloxane, α,ω-bis(3-aminobutyl)polydimethylsiloxane, bis(aminomethyl)ether, bis(2-aminoethyl)ether, bis(3-aminopropyl)ether, bis[(2-aminomethoxy)ethyl]ether, bis[2-(2-aminoethoxy)ethyl] ether, bis[2-(3-aminopropoxy)ethyl]ether, 1,2-bis(aminomethoxy)ethane, 1,2-bis(2-aminoethoxy)ethane, 1,2-bis[2-(aminomethoxy)ethoxy]ethane, 1,2-bis[2-(2-aminoethoxy) ethoxy]ethane, ethyleneglycolbis(3-aminopropyl)ether, diethyleneglycolbis(3-aminopropyl)ether, triethyleneglycolbis(3-aminopropyl)ether, ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, and 1,12-diaminododecane; alicyclic amines such as 1,2-diaminocyclohexane, 1,3-diaminocyclohexane, 1,4-diaminocyclohexane, 1,2-di(2-aminoethyl)cyclohexane, 1,3-di(2-aminoethyl)cyclohexane, 1,4-di(2-aminoethyl)cyclohexane, bis(4-aminocyclohexyl)methane, 2,6-bis(aminomethyl)bicyclo[2.2.1]heptane, and 2,5-bis (aminomethyl)bicyclo[2.2.1]heptane; and the like may be mentioned. Further, it is also possible to use a diamine where part or all of the hydrogen atoms on the aromatic rings of the above diamines are substituted with a substituent group selected from the group consisting of a fluoro group, methyl group, methoxy group, trifluoromethyl group, and trifluoromethoxy group.

These diamines may be used alone or in combinations of two or more kinds thereof.

The content of the polyimide precursor is preferably 50 to 99% by mass, more preferably 70 to 95% by mass, relative to the solid content of the composition of the fourth embodiment. The content in the above-defined range is advantageous in that an improvement in a coating film forming capability can be realized.

The photobase generating agent in the composition of the fourth embodiment is not particularly limited and conventional photobase generating agents may be used. Preferred photobase generating agents include, for example, photoactive carbamates such as triphenyl methanol, benzyl carbamate, and benzoin carbamate; amides such as O-carbamoyl-hydroxylamides, O-carbamoyloximes, aromatic sulfonamidse, α-lactam, N-(2-allylethynyl)amides and other amides; oxime esters; α-aminoacetophenone; cobalt complexes; 1-(anthraquinon-2-yl)ethylimidazole carboxylate; and compounds represented by the following general formula (v-2).

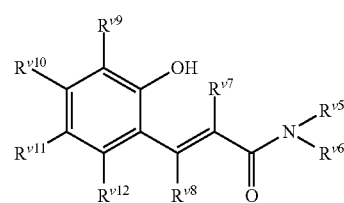

(v-2)

(wherein $R^{v5}$ and $R^{v6}$ each independently represent a hydrogen atom or an organic group and may be the same as or different from each other; $R^{v5}$ and $R^{v6}$ may be combined to form a cyclic structure or may contain a bond of hetero atom; provided that at least one of $R^{v5}$ and $R^{v6}$ represents an organic group; $R^{v7}$ and $R^{v8}$ each independently represent a hydrogen atom, a halogen atom or a hydroxyl, mercapto, sulfide, siliyl, silanol, nitro, nitroso, sulfino, sulfo, sulfonato, phosphino, phosphinyl, phosphono, phosphonato, or organic group and may be the same as or different from each other. $R^{v9}$, $R^{v10}$, $R^{v11}$, and $R^{v12}$ represent a hydrogen atom, a halogen atom, hydroxyl, mercapto, sulfide, siliyl, silanol, nitro, nitroso, sulfino, sulfo, sulfonato, phosphino, phosphinyl, phosphono, phosphonato, amino, ammonio, or organic group and may be the same as or different from each other, provided that any of $R^{v9}$, $R^{v10}$, $R^{V11}$, and $R^{v12}$ has a partial structure represented by the following general formula (v-3); two or more of $R^{v9}$, $R^{v10}$, $R^{v11}$, and $R^{v12}$ may be combined to form a cyclic structure or may contain a bond of a hetero atom.)

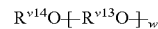

(v-3)

(wherein $R^{v13}$ represents a linking group bondable to two oxygen atoms; $R^{v14}$ represents a hydrogen atom, a silyl, silanol, phosphino, phosphinyl, phosphono, or organic group; and w is an integer of 1 or more.)

The content of the photobase generating agent is preferably 0.1 to 49.9% by mass relative to the whole solid content of the composition of the fourth embodiment. The photobase generating agent content in the above-defined range is advantageous in that satisfactory heat resistance and chemical resistance can be provided, an improvement in coating film forming capability can be realized, and failure to cure can be suppressed.

As described above, the composition of the fourth embodiment comprises a compound represented by the general formula (1), a compound represented by the general formula (10) and/or a compound represented by the general formula (19) Cured products having a high hardness can easily be obtained from the composition containing this compound. Further, when this compound is incorporated in a negative-type photosensitive resin composition, good micropatterning properties can be realized.

The content of the compound represented by the general formula (1), the compound represented by the general formula (10) and/or the compound represented by the general formula (19) is preferably 0.01 to 40% by mass relative to 100 parts by mass of the polyimide precursor. The content in the above-defined range is advantageous in that an improvement in coating film forming capability and curability of the composition of the fourth embodiment can easily be realized and, when the composition of the fourth embodiment is a negative-type photosensitive resin composition, good micropatterning properties can be provided while realizing good developability.

Organic solvents exemplified in the composition of the first embodiment may be mentioned as organic solvents usable in the composition of the fourth embodiment. Among these, polar solvents such as propylene glycol monomethyl ether, methyl ethyl ketone, cyclopentanone, cyclohexanone, ethyl acetate, propylene glycol monomethyl ether acetate, N,N-dimethylacetoamide, N-methyl-2-pyrrolidone, γ-butyrolactone and the like, and aromatic hydrocarbons such as toluene and the like, and mixtures thereof, are preferable.

The content of the organic solvent is preferably an amount such that the solid content concentration of the composition of the fourth embodiment is 1 to 50 mass %, and more preferably an amount such that the solid content concentration is 5 to 30 mass %.

(5) Composition of Fifth Embodiment

The composition of the fifth embodiment comprises an epoxy compound, a compound represented by the general formula (1), a compound represented by the general formula (10), and/or a compound represented by the general formula (19). The composition of the fifth embodiment may further contain a photobase generating agent or a photoacid generating agent and/or an organic solvent. When the composition of the fifth embodiment does not contain a photobase generating agent and a photoacid generating agent, the composition is a non-photosensitive resin composition. On the other hand, when the composition contains a photobase generating agent or a photoacid generating agent, the composition is photosensitive.

When the composition of the fifth embodiment is photosensitive, an specific example thereof is a negative-type photosensitive resin composition comprising an epoxy compound, a photobase generating agent or a photoacid generating agent, a compound represented by the general formula (1), a compound represented by the general formula (10) and/or a compound represented by the general formula (19). This negative-type photosensitive resin composition may further contain an organic solvent.

As the epoxy compound in the composition of the fifth embodiment, for example, a bisphenol A-type epoxy resin derived from bisphenol A and epichlorohydrin, a bisphenol F-type epoxy resin derived from bisphenol F and epichlorohydrin, a bisphenol S-type epoxy resin, a phenol novolak-type epoxy resin, a cresol novolak-type epoxy resin, a bisphenol A novolak-type epoxy resin, a bisphenol F novolak-type epoxy resin, an alicyclic epoxy resin, a diphenyl ether-type epoxy resin, a hydroquinone-type epoxy resin, a naphthalene-type epoxy resin, a biphenyl-type epoxy resin, a fluorene-type epoxy resin, a polyfunctional-type epoxy resin such as a trifunctional-type epoxy resin or tetrafunctional-type epoxy resin, a glycidyl ester-type epoxy resin, a glycidyl amine-type epoxy resin, a hydantoin-type epoxy resin, an isocyanurate-type epoxy resin, an aliphatic chain epoxy resin and the like may be mentioned. These epoxy resins may be halogenated, and may be hydrogenated. Examples of epoxy compounds in the composition of the fifth embodiment include compounds represented by any of the following formulae.

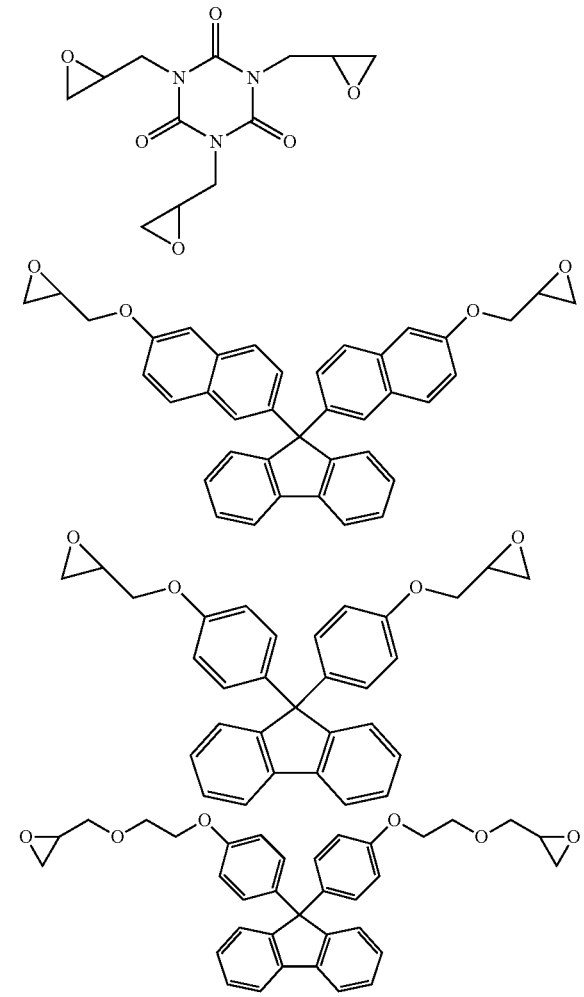

As commercially available epoxy compound products, for example JER Coat 828, 1001, 801N, 806, 807, 152, 604, 630, 871, YX8000, YX8034, and YX4000 by Japan Epoxy Resin Co., Epiclon 830, EXA835LV, HP4032D, and HP820 by DIC Corporation, the EP4100 series, EP4000 series, and EPU series by ADEKA Corporation, the Celloxide series (2021, 2021P, 2083, 2085, 3000, 8000, and the like), the EPOLEAD series, and the EHPE series by Daicel Corporation, the YD series, YDF series, YDCN series, YDB series, and phenoxy resins (polyhydroxy polyethers synthesized from bisphenols and epichlorohydrin, and containing epoxy groups at both terminals; YP series and the like) by New Nippon Steel Chemical Co., Ltd., the Denacol series by Nagase Chemtex Corporation, the EPO LIGHT series by Kyoeisha Chemical Co., Ltd., and the like may be mentioned, without being limited to these.

These epoxy resins may be used alone or in combinations of two or more kinds thereof.

The content of the epoxy compound is preferably 55 to 99 mass % with respect to the solid content of the composition of the fifth embodiment, more preferably 70 to 95 mass %. The content in the above-defined range is advantageous in that an improvement in a coating film forming capability can be realized.

Examples of photobase generating agents in the composition of the fifth embodiment include those exemplified in the composition of the fourth embodiment. Examples of photoacid generating agents in the composition of the fifth embodiment include those exemplified in the composition of the second embodiment.

The content of the photobase generating agent or the photoacid generating agent is preferably 0.1 to 49.9% by mass relative to the whole solid content of the composition of the fifth embodiment. The content in the above-defined range is advantageous in that satisfactory heat resistance and chemical resistance can be realized and, at the same time, an improvement in coating film forming capability and the suppression of a failure to cure can be realized.

As described above, the composition of the fifth embodiment comprises a compound represented by the general formula (1), a compound represented by the general formula (10) and/or a compound represented by the general formula (19). Cured products having a high hardness can be easily obtained from the composition containing this compound. Further, when this compound is incorporated in a negative-type photosensitive resin composition, good micropatterning properties can be realized.

The content of the compound represented by the general formula (1), the compound represented by the general formula (10) and/or the compound represented by the general formula (19) is preferably 1 to 200 parts by mass, more preferably 5 to 150 parts by mass, relative to 100 parts by mass of the epoxy compound. The content in the above-defined range is advantageous in that an improvement in coating film forming capability and curability of the composition of the fifth embodiment can easily be realized and, when the composition of the fifth embodiment is a negative-type photosensitive resin composition, good micropatterning properties can be provided while realizing good developability.

Organic solvents and organic acids exemplified in the composition of the first embodiment may be mentioned as organic solvents usable in the composition of the fifth embodiment. Organic acids include carboxylic acids such as acetic acid and propionic acid. Among these, polar solvents such as propylene glycol monomethyl ether, methyl ethyl ketone, cyclopentanone, cyclohexanone, ethyl acetate, propylene glycol monomethyl ether acetate, N,N-dimethylacetoamide, N-methyl-2-pyrrolidone, γ-butyrolactone and the like, aromatic hydrocarbons such as toluene and the like, organic acids such as acetic acid, and mixtures thereof, are preferable. In particular, when the composition of the fifth embodiment is free from the photobase generating agent and the photoacid generating agent, organic acids such as acetic acid are preferred from the viewpoint of curability. Organic acids are considered to function as a proton donor.

The content of the organic solvent is such that the solid content concentration of the composition of the fifth embodiment is preferably 1 to 50% by mass, more preferably 5 to 30% by mass.

(6) Composition of Sixth Embodiment

The composition of the sixth embodiment comprises an epoxy-group-containing polycarboxylic acid resin, a compound represented by the general formula (1), a compound represented by the general formula (10), and/or a compound represented by the general formula (19). The composition of the sixth embodiment may further contain a photobase generating agent or a photoacid generating agent and/or an organic solvent. When the composition of the sixth embodiment does not contain a photobase generating agent and a photoacid generating agent, the composition is a non-photosensitive resin composition. On the other hand, when the composition contains a photobase generating agent or a photoacid generating agent, the composition is photosensitive.

When the composition of the sixth embodiment is photosensitive, a specific example thereof is a negative-type photosensitive resin composition comprising an epoxy-group-containing polycarboxylic acid resin, a photobase generating agent or a photoacid generating agent, a compound represented by the general formula (1), a compound represented by the general formula (10) and/or a compound represented by the general formula (19). This negative-type photosensitive resin composition may further contain an organic solvent As the epoxy group-containing polycarbonate resin in the composition of the sixth embodiment, for example, it is possible to use one obtained by reacting an epoxy compound having two or more epoxy groups per molecule with a monocarboxylic acid having one or more alcoholic hydroxyl groups per molecule, and further reacting the reaction product thereof with a polybasic acid anhydride.

As the epoxy compound having two or more epoxy groups per molecule, for example, a novolak-type epoxy resin, a bisphenol-type epoxy resin, a trisphenolmethane-type epoxy resin, tris(2,3-epoxypropyl)isocyanurate, biphenyl diglycidyl ether, an alicyclic epoxy resin, and copolymer-type epoxy resins may be mentioned.

As the novolak-type epoxy resin, for example, one obtained by reacting epichlorohydrin or methylepichlorohydrin with a novolak obtained by reacting a phenol such as phenol, cresol, halogenated phenol, alkylphenol and the like with formaldehyde under the presence of an acid catalyst, and the like may be mentioned. As commercially available products, EOCN-102S, EOCN-103S, EOCN-104S, EOCN-1027, EPPN-201, and BREN-S (all by Nippon Kayaku Co., Ltd.); DEN-431, DEN-439 (both by the Dow Chemical Company); N-730, N-770, N-865, N-665, N-673, and VH-4150 (all by Dainippon Ink and Chemicals Co.), and the like may be mentioned.

As the bisphenol-type epoxy resin, for example, one obtained by reacting an epichlorohydrin or methylepichlorohydrin with a bisphenol such as bisphenol A, bisphenol F, bisphenol S, tetrabromobisphenol A and the like; or those obtained by reacting an epichlorohydrin or methylepichlorohydrin with a diglycidyl ether of bisphenol A or bisphenol F and a condensate of the above bisphenol; and the like may be mentioned. As commercially available products, Epicoat 1004, Epicoat 1002, Epicoat 4002, and Epicoat 4004 (all by Yuka Shell Epoxy Co.) and the like may be mentioned.

As the trisphenolmethane-type epoxy resin, for example, one obtained by reacting an epichlorohydrin or methyl-epichlorohydrin with trisphenolmethane or triscresolmethane may be mentioned. As commercially available products, EPPN-501 and EPPN-502 (both by Nippon Kayaku Co., Ltd.) and the like may be mentioned.

As the alicyclic epoxy resin, Celloxide 2021 by Daicel Corporation, Epomic VG-3101 by Mitsui Chemicals, Inc., E-1031S by Yuka Shell Epoxy Co., and EPB-13 and EPB-27 by Nippon Soda Co., Ltd and the like may be mentioned. Further, as the copolymer-type epoxy resin, CP-50M and CP-50S by NOF Corporation, which are copolymers of glycidyl methacrylate and styrene and α-methylstyrene, or copolymers of glycidyl methacrylate and cyclohexy maleide and the like may be mentioned.

As being especially preferable among these epoxy resins having two or more epoxy groups per molecule, for example cresol novolak-type epoxy resin, phenol novolak-type epoxy resin, bisphenol-type epoxy resin, trisphenolmethane-type epoxy resin and the like may be mentioned. In particular, a condensation polymer of α-hydroxyphenyl-ω-hydropoly(biphenyldimethylene-hydroxyphenylene) and 1-chloro-2,3-epoxypropane; and α-2,3-epoxypropoxyphenyl-ω-hydropoly{2-(2,3-epoxypropoxy)-benzylidine-2,3-epoxypropoxyphenylene} are preferable.

As the monocarboxylic acid having one or more alcoholic hydroxyl groups per molecule, for example, hydroxymonocarboxylic acids such as dimethylolpropionic acid, dimethylol acetate, dimethylol butyrate, dimethylol valerate, dimethylol caproic acetate, hydroxypivulic acid and the like may be mentioned. Among these, monocarboxylic acids having 1 to 5 alcoholic hydroxyl groups per molecule are preferable.

As the polybasic acid anhydride, for example, succinic anhydride, maleic anhydride, phthalic anhydride, tetrahydro phthalic anhydride, hexahydro phthalic anhydride, methyl-endomethylene tetrahydro phthalic anhydride, trimellitic anhydride, pyromellitic anhydride and the like may be mentioned.

The reaction of the above described epoxy compound and the above described monocarboxylic acid is preferably of 0.1 to 0.7 mol of the monocarboxylic acid with respect to 1 equivalent of epoxy of the epoxy compound, more preferably 0.2 to 0.5 mol. In this reaction, it is preferable to use an organic solvent which dos not react with the epoxy compound or the polybasic acid anhydride, and which does not have hydroxyl groups or carboxyl groups. Further, a catalyst for promoting the reaction (for example, triphenylphosphine, benzyldimethylamine, trialkylammonium chloride, triphenyl stibine and the like) may be used. In the case of using a catalyst, particularly after the reaction is finished, deactivating the catalyst using an organic peroxide or the like stably maintains the shelf life which is preferable. The content of the catalyst is preferably 0.1 to 10 wt % with respect to the reaction mixture, and the reaction temperature is preferably 60 to 150° C. In this way, it is possible to obtain a reactant from the above described epoxy compound and the above described monocarboxylic acid.

In the reaction between this reactant and a polybasic acid anhydride, the polybasic acid anhydride is preferably reacted in such an amount that the acid value of the finally obtained epoxy group-containing polycarboxylic acid resin is 50 to 150 mgKOH/g. The reaction temperature is preferably 60 to 150° C. In this way, it is possible to obtain an epoxy group-containing polycarboxylic acid resin.

These epoxy group-containing polycarboxylic acid resins may be used alone or in combinations of two or more kinds thereof.

The content of the epoxy group-containing polycarboxylic acid resin is preferably 30 to 80 mass % with respect to the solid content of the composition of the sixth embodiment, and more preferably 40 to 70 mass %. The content in the above-defined range is advantageous in that an improvement in a coating film forming capability can be realized.

Examples of photobase generating agents in the composition of the sixth embodiment include those exemplified in the composition of the fourth embodiment. Examples of photoacid generating agents in the composition of the sixth embodiment include those exemplified in the composition of the second embodiment.

The content of the photobase generating agent or the photoacid generating agent is preferably 0.5 to 30% by mass, more preferably 1 to 20% by mass, relative to the solid content of the composition of the sixth embodiment. The content in the above-defined range is advantageous in that good curability of the composition of the sixth embodiment can be realized.

As described above, the composition of the sixth embodiment comprises a compound represented by the general formula (1), a compound represented by the general formula (10) and/or a compound represented by the general formula (19). Cured products having a high hardness can easily be obtained from the composition containing this compound. Further, when this compound is incorporated in a negative-type photosensitive resin composition, good micropatterning properties can be realized.

The content of the compound represented by the general formula (1), the compound represented by the general formula (10) and/or the compound represented by the general formula (19) is preferably 20 to 70% by mass, more preferably 30 to 60% by mass, further preferably 5 to 50% by mass, relative to the solid content of the composition of the sixth composition. The content in the above-defined range is advantageous in that an improvement in coating film forming capability and curability of the composition of the sixth embodiment can easily be realized and, when the composition of the sixth embodiment is a negative-type photosensitive resin composition, good micropatterning properties can be provided while realizing good developability.

The composition of the sixth embodiment may further comprise a sensitizing agent. As the sensitizing agent, for example, an anthracene compound having an alkoxy group at the 9-position and 10-position (9,10-dialkoxy-anthracene derivative) is preferable. As the alkoxy group, an alkoxy group with 1 to 4 carbon atoms may be mentioned. The 9,10-dialkoxy-anthracene derivative may have a further substituent group. As the substituent group, a halogen atom, an alkyl group with 1 to 4 carbon atoms, a sulfonic acid alkyl ester group, a carboxylic acid alkyl ester group and the like may be mentioned. As the alkyl group in the sulfonic acid alkyl ester group or carboxylic acid alkyl ester group, an alkyl group with 1 to 4 carbon atoms may be mentioned. The substitution position of these substitutents is preferably the 2-position.

As the 9,10-dialkoxy-anthracene derivative, for example, 9,10-dimethoxy-anthracene, 9,10-diethoxy-anthracene, 9,10-dipropoxy-anthracene, 9,10-dimethoxy-2-ethyl-anthracene, 9,10-diethoxy-2-ethyl-anthracene, 9,10-dipropoxy-2-ethyl-anthracene, 9,10-dimethoxy-2-chloro-anthracene, 9,10-dimethoxyanthracene-2-sulfonic acid methyl ester, 9,10-diethoxyanthracene-2-sulfonic acid methyl ester, 9,10-dimethoxyanthracene-2-carboxylic acid methyl ester, and the like may be mentioned.

These compounds may be obtained by treating an anthraquinone derivative with a reducing agent such as zinc dust, hydrosulfite, palladium-carbon, sodium borohydride and the like in an alkali aqueous solution, to make a 9,10-dihdroxy-anthracene derivative, and then alkoxylating the 9,10-position with a sulfuric acid ester such as dimethyl sulfate, diethyl sulfate and the like; a toluenesulfonate ester such as methyl toluenesulfonate, ethyl toluenesulfonate, propyl toluenesulfonate, monoethylene glycol toluenesulfonate ester and the like; or a benzenesulfonate ester such as methyl benzenesulfonate, ethyl benzenesulfonate, propyl benzenesulfonate and the like.

These sensitizing agents may be used alone or in combinations of two or more kinds thereof.

The content of the sensitizing agent is preferably a molar ratio of 0.1 to 6 with respect to the above described photoacid generating agent, more preferably 0.2 to 4. When the composition of the sixth embodiment is a negative-type photosensitive resin, the above ranges improve the sensitivity and curability of the composition of the sixth embodiment.

The composition of the sixth embodiment may further comprise a modifying component for adjusting the moisture resistance, heat resistance, adhesiveness and the like. These modifying components may be ones which are themselves cured by heat or ultraviolet radiation, or may be one which react with a residual hydroxyl group or carboxyl group or the like of an epoxy group-containing polycarboxylic acid resin by heat or ultraviolet radiation. Specifically, an epoxy compound having one or more epoxy groups per molecule, a melamine derivative (for example, hexamethoxy melamine, hexabutoxylated melamine, condensed hexamethoxy melamine and the like), bisphenol A-type compounds (for example, tetramethyloyl bisphenol A and the like), oxazoline compounds and the like may be mentioned.

As the epoxy compound having one or more epoxy groups per molecule, bisphenol A-type epoxy resins such as Epikote 1009 and 1031 (both manufactured by Yuka Shell Co.), Epiclon N-3050 and N-7050 (both manufactured by Dainippon Ink and Chemicals Co.), and DER-642U and DER-673MF (both manufactured by the Dow Chemical Company); hydrogenated bisphenol A-type epoxy resins such as ST-2004 and ST-2007 (both manufactured by Tohto Chemical Industry Co., Ltd.); bisphenol F-type epoxy resins such as YDF-2004 and YDF 2007 (both manufactured by Tohto Chemical Industry Co., Ltd.); brominated bisphenol A-type expoxy resins such as SR-BBS and SR-TBA-400 (both manufactured by Sakamoto Yakuhin Kogyo Co., Ltd.), and YDB-600 and YDB-715 (both manufactured by Tohto Chemical Industry Co., Ltd.); novolak-type epoxy resins such as EPPN-201, EOCN-103, EOCN-1020, and BREN (all manufactured by Nippon Kayaku Co., Ltd.); novolak-type epoxy resins of bisphenol A such as Epiclon N-880 manufactured by Dainippon Ink and Chemicals Co.; rubber-modified epoxy resins such as Epiclon TSR-601 manufactured by Dainippon Ink and Chemicals Co. and R-1415-1 manufactured by A.C.R. Co.; bisphenyl S-type epoxy resins such as EBPS-200 manufactured by Nippon Kayaku Co., Ltd. and Epiclon EXA-1514 manufactured by Dainippon Ink and Chemicals Co.; diglycidyl terephthalates such as Purenmer DGT manufactured by NOF Corporation; triglycidyl isocyanurates such as TEPIC manufactured by Nissan Chemical Industries Ltd.; bixylenol-type epoxy resins such as YX-4000 manufactured by Yuka Shell Co.; bisphenol-type epoxy resins such as YL-6056 manufactured by Yuka Shell Co.; alicyclic epoxy resins such as Celloxide 2021 manufactured by Daicel Corporation; and the like may be mentioned.

The content of the modifying components is preferably 50 mass % or less with respect to the solid content of the composition of the sixth embodiment, more preferably 30 mass % or less.

The composition of the sixth embodiment, in order to further improve the characteristics such as the adhesiveness, hardness and the like, may further comprise a well-known filler such as barium sulfate, barium titanate, silica, talc, clay, magnesium carbonate, calcium carbonate, aluminum oxide, mica and the like.

The content of the filler is preferably 60 mass % or less with respect to the solid content of the composition of the sixth embodiment, more preferably 5 to 40 mass %.

The composition of the sixth embodiment may further comprise a coloring agent such as phthalocyanine blue, phthalocyanine green, disazo yellow, crystal violet, titanium oxide, carbon black and the like; a thickener such as ultrafine powdered silica, montmorillonite and the like, an anti-foaming agent and/or leveling agent such as a silicone high polymer, a fluorinated high polymer and the like; an adhesiveness imparting agent such as a silane coupling agent and the like.

As the organic solvent of the composition of the sixth embodiment, the organic solvents listed as examples in the composition of the first embodiment may be mentioned.

The content of the organic solvent is preferably an amount such that the solid content concentration of the composition of the sixth embodiment is 1 to 50 mass %, and more preferably an amount such that the solid content concentration is 5 to 30 mass %.

(7) Composition of Seventh Embodiment

The composition of the seventh embodiment is an energy-sensitive composition comprising a compound represented by the general formula (1), a compound represented by the general formula (10), and/or a compound represented by the general formula (19), and an acid generating agent or a base generating agent. Examples of acid generating agents include, for example, photoacid generating agents and thermal acid generating agents. Examples of base generating agents include, for example, photobase generating agents and thermal base generating agents. The composition of the seventh embodiment may further contain an organic solvent.

As described above, the composition of the seventh embodiment comprises a compound represented by the general formula (1), a compound represented by the general formula (10) and/or a compound represented by the general formula (19). Cured products having a high hardness can be obtained from the composition containing this compound.

The content of the compound represented by the general formula (1), the compound represented by the general formula (10) and/or the compound represented by the general formula (19) is preferably 50.1 to 99.9% by mass, more preferably 70 to 99.5% by mass, further preferably 80 to 99% by mass, relative to the solid content of the composition of the seventh embodiment. The content in the above-defined range is advantageous in that, for example, a coating film forming capability and curability in the composition of the seventh embodiment can easily be improved.

Examples of photoacid generating agents include those exemplified in the composition of the second embodiment.

Thermal acid generating agents include, for example, 2,4,4,6-tetrabromocyclohexadienone, benzoin tosylate, 2-nitrobenzyl tosylate, and other alkyl esters of organic sulfonic acids. Specifically, onium salts such as sulfonium salts, iodonium salts, benzothiazonium salts, ammonium salts, and phosphonium salts may be mentioned. Among these onium salts, iodonium salts, sulfonium salts, and benzothiazonium salts are preferred. Specific examples of sulfonium salts and benzothiazonium salts include 4-acetoxyphenyl dimethylsulfonium hexafluoroarsenate, benzyl-4-hydroxyphenylmethylsulfonium hexafluoroantimonate, 4-acetoxyphenylbenzylmethylsulfoniumhexafluoroantimonate, dibenzyl-4-hydroxyphenylsulfoniumhexafluoroantimonate, 4-acetoxyphenylbenzylsulfoniumhexafluoroantimonate, 3-benzylbenzothiazolium hexafluoroantimonate, and compounds represented by the following formula.

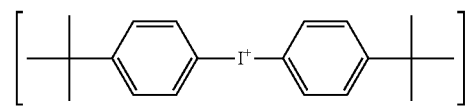

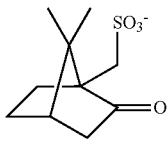

Examples of photobase generating agents include those exemplified in the composition of the fourth embodiment.

Thermal base generating agents include, for example, carbamate derivatives such as 1-methyl-1-(4-biphenylyl) ethyl carbamate, 1,1-dimethyl-2-cyanoethyl carbamate; urea; urea derivatives such as N,N-dimethyl-N'-methylurea; dihydropyridine derivatives such as 1,4-dihydronicotinamide; quaternized ammonium salts of organic silane or organic borane; and dicyandiamide. Other examples include guanidine trichloroacetate, methylguanidine trichloroacetate, potassium trichloroacetate, guanidine phenylsulfonylacetate, guanidine p-chlorophenylsulfonylacetate, guanidine p-methanesulfonylphenylsulfonyl acetate, potassium phenylpropiolate, guanidine phenylpropiolate, cesium phenylpropiolate, guanidine p-chlorophenylpropiolate, guanidine p-phenylene-bis-phenylpropiolate, tetramethylammonium phenylsulfonylacetate, and tetramethylammonium phenylpropiolate.

The content of the acid generating agent or the base generating agent is preferably 0.1 to 49.9% by mass, more preferably 0.5 to 30% by mass, further preferably 1 to 20% by mass, relative to the solid content of the energy-sensitive composition. The content in the above-defined range is advantageous in that good curability of the energy-sensitive composition can easily be realized.

Organic solvents exemplified in the composition of the first embodiment may be mentioned as organic solvents usable in the composition of the seventh embodiment.

The content of the organic solvent is such that the solid content concentration of the composition of the seventh embodiment is preferably 0.5 to 70% by mass, more preferably 1 to 55% by mass.

(8) Composition of Eighth Embodiment

The composition of the eighth embodiment comprises a hydroxyl-group-containing compound and/or a carboxyl-group-containing compound, a compound represented by the general formula (1), a compound represented by the general formula (10), and/or a compound represented by the general formula (19). The composition of the eighth embodiment may further contain an acid generating agent or a base generating agent and/or an organic solvent.

The hydroxyl-group-containing compound is not particularly limited, and examples thereof include those represented by the following general formula:

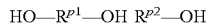

HO—$R^{p1}$—OH  $R^{p2}$—OH (wherein $R^{p1}$ and $R^{p2}$ represent an organic group.)

The carboxyl-group-containing compound is not particularly limited, and examples thereof include those represented by the following general formula.

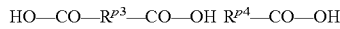

HO—CO—$R^{p3}$—CO—OH  $R^{p4}$—CO—OH (wherein $R^{p3}$ and $R^{p4}$ represent an organic group.)

Examples of $R^{p1}$ and $R^{p3}$ include divalent hydrocarbon groups, divalent heterocyclic groups, and groups formed by mutual bonding of these groups, and divalent hydrocarbon groups are preferred. The divalent hydrocarbon groups and the divalent heterocyclic groups may have a substituent. Preferably, $R^{p1}$ and $R^{p3}$ have an acyclic structure.

Examples of divalent hydrocarbon groups include divalent aliphatic hydrocarbon groups, divalent alicyclic hydrocarbon groups, divalent aromatic hydrocarbon groups, and groups formed by bonding two or more of these groups.

Divalent aliphatic hydrocarbon groups include, for example, alkylene groups having 1 to 20 carbon atoms, preferably 1 to 10 carbon atoms, still preferably 1 to 3 carbon atoms such as methylene, ethylene, propylene, isopropylene, butylene, isobutylene, s-butylene, t-butylene, pentylene, hexylene, decylene, and dodecylene groups; and alkenylene groups having 2 to 20 carbon atoms, preferably 2 to 10 carbon atoms, further preferably 2 or 3 carbon atoms such as vinylene, propenylene, and 1-butenylene groups; and alkynylene groups having 2 to 20 carbon atoms, preferably 2 to 10 carbon atoms, further preferably 2 or 3 carbon atoms, such as ethynylene and propynylene groups.

Divalent alicyclic hydrocarbon groups include cycloalkylene groups having 3 to 20 carbon atoms, preferably 3 to 15 carbon atoms, still preferably 5 to 8 carbon atoms, such as cyclopropylene, cyclobutylene, cyclopentylene, cyclohexylene, and cyclooctylene groups; cycloalkenylene groups having 3 to 20 carbon atoms, preferably 3 to 15 carbon atoms, still preferably 5 to 8 carbon atoms such as cyclopentenylene and cyclohexenylene groups; and divalent crosslinking cyclic hydrocarbon groups having 4 to 20 carbon atoms, preferably 6 to 16 carbon atoms, still preferably 7 to 12 carbon atoms such as perhydronaphtylene, norbornylene, adamantylene, and tetracyclo[4.4.0.1$^{2,5}$.1$^{7,10}$] dodecylene groups.

Divalent aromatic hydrocarbon groups include arylene groups having 6 to 20 carbon atoms, preferably 6 to 13 carbon atoms, such as phenylene, naphthylene, and fluorenylene groups.

Examples of groups formed by bonding a divalent aliphatic hydrocarbon group and a divalent alicyclic hydrocarbon group include cycloalkylene-alkylene groups (for example, $C_{3-20}$ cycloalkylene-$C_{1-4}$ alkylene groups) such as cyclopentylene methylene, cyclohexylene methylene, and cyclohexylene ethylene groups.

Examples of groups formed by bonding a divalent aliphatic hydrocarbon group and a divalent aromatic hydrocarbon group include arylene-alkylene groups (for example, $C_{6-20}$ arylene-$C_{1-4}$ alkylene groups), and arylene-alkylene-arylene groups (for example, $C_{6-20}$ arylene-$C_{1-4}$ alkylene group-$C_{6-20}$ arylene groups)

Examples of groups formed by bonding two or more divalent aromatic hydrocarbon groups include arylene-arylene groups (for example, $C_{6-20}$ arylene-$C_{6-20}$ arylene groups), arylene-arylene-arylene groups (for example, $C_{6-10}$ arylene-$C_{6-13}$ arylene-$C_{6-10}$ arylene groups).

Among these divalent hydrocarbon groups, those having a cyclic structure are preferred, and $C_{6-10}$ arylene-$C_{6-13}$ arylene group-$C_{6-10}$ arylene groups, $C_{6-20}$ arylene-$C_{1-4}$ alkylene group-$C_{6-20}$ arylene groups, and divalent crosslinking cyclic hydrocarbon groups having 7 to 12 carbon atoms are particularly preferred.

The divalent hydrocarbon groups may have various substituents, for example, halogen atoms, an oxo group, a hydroxyl group, substituted oxy groups (for example, alkoxy, aryloxy, aralkyloxy, and acyloxy groups), a carboxyl group, substituted oxycarbonyl groups (alkoxycarbonyl groups, aryloxycarbonyl groups, and aralkyloxycarbonyl groups), substituted or unsubstituted carbamoyl groups, a cyano group, a nitro group, substituted or unsubstituted amino groups, a sulfo group, and hetrocyclic groups. The hydroxyl group and the carboxyl group may be protected with protective groups commonly used in the field of organic synthesis. An aromatic or non-aromatic hetero ring may be fused to the divalent alicyclic hydrocarbon group and the ring of the divalent aromatic hydrocarbon group.

The divalent heterocyclic group is a group formed by removing two hydrogen atoms from the heterocyclic compound. The heterocyclic compound may be an aromatic heterocyclic compound or a non-aromatic heterocyclic compound. Such heterocyclic compounds include, for example, heterocyclic compounds containing an oxygen atom as a hetero atom (for example, three-membered ring heterocyclic compounds such as oxirane, four-membered ring heterocyclic compounds such as oxetane, five-membered ring heterocyclic compounds such as furan, tetrahydrofuran, oxazole, and γ-butyrolactone, six-membered ring heterocyclic compounds such as 4-oxo-4H-pyran, tetrahydropyran, and morpholine, heterocyclic compounds having a fused ring such as benzofuran, 4-oxo-4H-chromene, and chromane, and heterocyclic compounds having a crosslinking ring such as 3-oxatricyclo[4.3.1.1$^{4,8}$]undecane-2-one, 3-oxatricyclo[4.2.1.0$^{4,8}$]nonan-2-one), heterocyclic compounds containing a sulfur atom as a hetero atom (for example, five-membered ring heterocyclic compounds such as thiophene, thiazole, and thiadiazole, six-membered ring heterocyclic compounds such as 4-oxo-4H-thiopyran, and heterocyclic compounds having a fused ring such as benzothiophene), heterocyclic compounds containing a nitrogen atom as a hetero atom (for example, five-membered ring heterocyclic compounds such as pyrrole, pyrrolidine, pyrazole, imidazole, and triazole, six-membered ring heterocyclic compounds such as pyridine, pyridazine, pyrimidine, pyrazine, piperidine, and piperazine, and heterocyclic compounds having a fused ring such as indole, indoline, quinoline, acridine, naphthyridine, quinazoline, and purine). The divalent heterocyclic group may have, in addition to substituents optionally possessed by the divalent hydrocarbon group, alkyl groups (for example, $C_{1-4}$ alkyl groups such as methyl and ethyl groups), cycloalkyl groups, aryl groups (for example, $C_{6-10}$ aryl groups such as phenyl and naphthyl groups).

Examples of $R^{p2}$ and $R^{p4}$ include monovalent hydrocarbon groups, monovalent heterocyclic groups, and groups formed by mutual bonding of these groups, and monovalent hydrocarbon groups are preferable. The monovalent hydrocarbon group and monovalent heterocyclic group may have a substituent. Preferably, $R^{p2}$ and $R^{p4}$ have acyclic structure.

Examples of monovalent hydrocarbon groups include monovalent aliphatic hydrocarbon groups, monovalent alicyclic hydrocarbon groups, monovalent aromatic hydrocarbon groups, and groups formed by bonding between two or more of these groups.

Examples of monovalent aliphatic hydrocarbon groups include alkyl groups having 1 to 20 carbon atoms, preferably 1 to 10 carbon atoms, more preferably 1 to 3 carbon atoms, such as methyl, ethyl, propyl, isopropyl, butyl, isobutyl, s-butyl, t-butyl, pentyl, hexyl, decyl, and dodecyl groups; alkenyl groups having 2 to 20 carbon atoms, preferably 2 to 10 carbon atoms, more preferably 2 or 3 carbon atoms, such as vinyl, aryl, and 1-butenyl groups; and alkynyl groups having 2 to 20 carbon atoms, preferably 2 to 10 carbon atoms, more preferably 2 or 3 carbon atoms, such as ethynyl and propynyl groups.

Monovalent alicyclic hydrocarbon groups include cycloalkyl groups having 3 to 20 carbon atoms, preferably 3 to 15 carbon atoms, more preferably 5 to 8 carbon atoms, such as cyclopropyl, cyclobutyl, cyclopentyl, cyclohexyl, and cyclooctyl groups; cycloalkenyl groups having 3 to 20 carbon atoms, preferably 3 to 15 carbon atoms, more preferably 5 to 8 carbon atoms, such as cyclopentenyl and cyclohexenyl groups; and monovalent crosslinking cyclic hydrocarbon groups having 4 to 20 carbon atoms, preferably 6 to 16 carbon atoms, more preferably 7 to 12 carbon atoms, such as perhydronaphthalen-1-yl, norbornyl, adamantyl, and tetracyclo[4.4.0.1$^{2,5}$.1$^{7,10}$]dodecan-3-yl groups.

Monovalent aromatic hydrocarbon groups include aryl groups having 6 to 20 carbon atoms, preferably 6 to 13 carbon atoms, such as phenyl, naphthyl, and fluorenyl groups.

Groups formed by bonding monovalent aliphatic hydrocarbon groups and monovalent alicyclic hydrocarbon groups include, for example, cycloalkyl-alkyl groups (for example, $C_{3-20}$ cycloalkyl-$C_{1-4}$ alkyl groups) such as cyclopentylmethyl, cyclohexylmethyl, and 2-cyclohexylethyl groups.

Groups formed by bonding monovalent aliphatic hydrocarbon groups and monovalent aromatic hydrocarbon groups include, for example, aralkyl groups (for example, $C_{7-18}$ aralkyl groups), alkyl-aryl groups (for example, $C_{1-4}$ alkyl-$C_{6-20}$ aryl groups, more specifically phenyl or naphthyl groups substituted by 1 to 4 $C_{1-4}$ alkyl groups), aryl-alkyl-aryl groups (for example, $C_{6-20}$ aryl-$C_{1-4}$ alkyl group-$C_{6-20}$ aryl groups).

Groups formed by bonding between two or more monovalent aromatic hydrocarbon groups include, for example, aryl-aryl groups (for example, $C_{6-20}$ aryl-$C_{6-20}$ aryl groups), aryl-aryl-aryl groups (for example, $C_{6-10}$ aryl-$C_{6-13}$ aryl-$C_{6-10}$ aryl groups).

Among these monovalent hydrocarbon groups, monovalent hydrocarbon groups having a cyclic structure are preferred, and $C_{6-10}$ aryl-$C_{6-13}$ aryl-$C_{6-10}$ aryl groups, $C_{6-20}$ aryl-$C_{1-4}$ alkyl group-$C_{6-20}$ aryl groups, and monovalent crosslinking cyclic hydrocarbon groups having 7 to 12 carbon atoms are particularly preferred.

The monovalent hydrocarbon group may have various substituents. Specific examples of substituents include those described above as examples of substituents optionally possessed by divalent hydrocarbon groups. Further, aromatic or non-aromatic heterocyclic rings may be condensed with the ring of monovalent alicyclic hydrocarbon and monovalent aromatic hydrocarbon groups.

The monovalent heterocyclic group represents a group formed by removing a hydrogen atom from the heterocyclic compound. The heterocyclic compound may be an aromatic heterocyclic compound or a non-aromatic heterocyclic compound. Such heterocyclic rings include, for example, those exemplified above in the description in connection with the divalent heterocyclic group. The monovalent heterocyclic group may contain, in addition to substituents optionally possessed by the monovalent hydrocarbon groups, substituents such as alkyl groups (for example, $C_{1-4}$ alkyl groups such as methyl and ethyl groups), cycloalkyl groups, and aryl groups (for example, $C_{6-10}$ aryl groups such as phenyl and naphthyl groups).

Specific examples of hydroxyl-group-containing compounds include compounds those represented by the following formula.

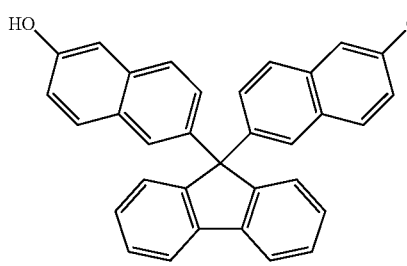

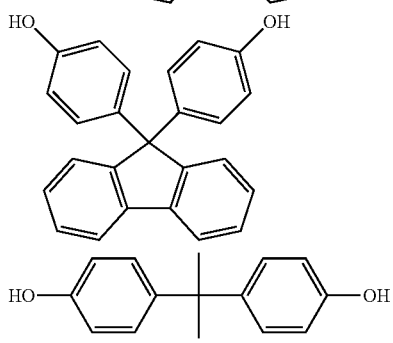

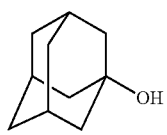

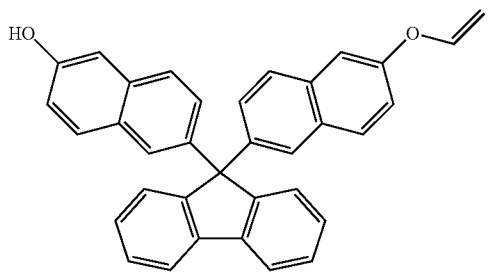

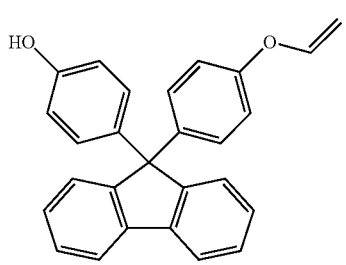

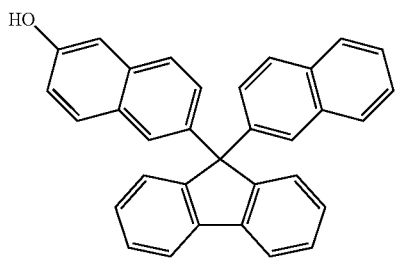

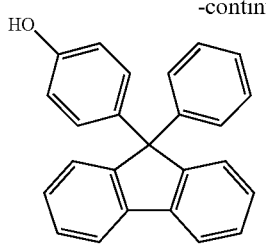

Specific examples of carboxyl-group-containing compounds include compounds those represented by the following formula.

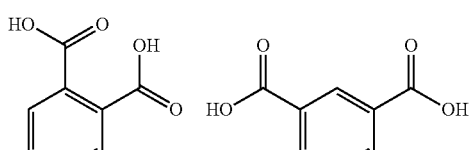

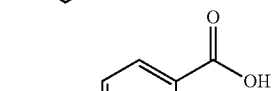

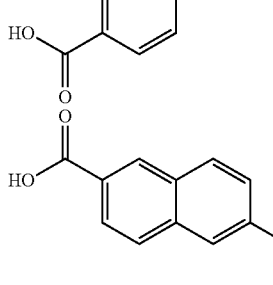

The content of the hydroxyl-group-containing compound and/or the carboxyl-group-containing compound is preferably 1 to 99% by mass, more preferably 20 to 97% by mass, further preferably 50 to 95% by mass, relative to the solid content of the composition of the eighth embodiment. The content in the above-defined range is advantageous in that the curability of the composition can easily be improved.

As described above, the composition of the eighth embodiment comprises a compound represented by the general formula (1), a compound represented by the general formula (10) and/or a compound represented by the general formula (19). Cured products having a high hardness can be obtained from the composition containing this compound.

The content of the compound represented by the general formula (1), the compound represented by the general formula (10) and/or the compound represented by the general formula (19) is preferably 1 to 99% by mass, more preferably 3 to 80% by mass, 5 to 50% by mass, relative to the solid content of the composition of the eighth embodiment. The content in the above-defined range is advantageous in that, for example, a coating film forming capability and curability in the composition of the eighth embodiment can easily be improved.

Examples of acid generating agents and base generating agents in the composition of the eighth embodiment include those exemplified in the composition of the seventh embodiment.

The content of the acid generating agent or the base generating agent is preferably 0.5 to 30% by mass, more preferably 1 to 20% by mass, relative to the solid content of the composition of the eighth embodiment. The content in the above-defined range is advantageous in that good curability of the composition can easily be realized.

Organic solvents exemplified in the composition of the first embodiment may be mentioned as organic solvents usable in the composition of the eighth embodiment.

The content of the organic solvent is such that the solid content concentration of the composition of the eighth embodiment is preferably 1 to 50% by mass, more preferably 5 to 30% by mass.

(9) Composition of Ninth Embodiment

The composition of the ninth embodiment comprises a silicon-containing compound, a compound represented by the general formula (1), a compound represented by the general formula (10), and/or a compound represented by the general formula (19). The composition of the ninth embodiment may further contain an organic solvent.

Examples of silicon-containing compounds in the composition of the ninth embodiment include polysiloxanes such as dimethylpolysiloxane. Such polysiloxanes may have, for example, a functional group such as a hydroxyl group at both ends of the molecular chain. The silicon-containing compounds may be used solely or in a combination of two or more kinds thereof.

The content of the silicon-containing compound is preferably 1 to 99% by mass, more preferably 20 to 97% by mass, further more preferably 30 to 95% by mass, relative to the solid content of the composition of the ninth embodiment. The content in the above-defined range is advantageous in that an improvement in chemical resistance of the resultant cured product can easily be realized.

As described above, the composition of the ninth embodiment comprises a compound represented by the general formula (1), a compound represented by the general formula (10) and/or a compound represented by the general formula (19). Cured products having a high hardness can easily be obtained from the composition containing this compound.

The content of the compound represented by the general formula (1), the compound represented by the general formula (10) and/or the compound represented by the general formula (19) is preferably 1 to 99% by mass, more preferably 3 to 80% by mass, further more preferably 5 to 70% by mass, relative to the solid content of the composition of the ninth embodiment. The content in the above-defined range is advantageous in that, for example, a coating film forming capability and curability in the composition of the ninth embodiment can easily be improved.

Organic solvents exemplified in the composition of the first embodiment may be mentioned as organic solvents usable in the composition of the ninth embodiment.

The content of the organic solvent is such that the solid content concentration of the composition of the ninth embodiment is preferably 1 to 50% by mass, more preferably 5 to 30% by mass.

(10) Composition of Tenth Embodiment

The composition of the tenth embodiment comprises an inorganic filler, a compound represented by the general formula (1), a compound represented by the general formula (10), and/or a compound represented by the general formula (19). The composition of the tenth embodiment may further contain an acid generating agent or a base generating agent and/or an organic solvent.

Examples of inorganic fillers in the composition of the tenth embodiment include titanium oxide and silica. The inorganic fillers may be used solely or in a combination of two or more kinds thereof.

The content of the inorganic filler is preferably 1 to 99% by mass, more preferably 20 to 97% by mass, further more preferably 30 to 95% by mass, relative to the solid content of the composition of the tenth embodiment. The content in the above-defined range is advantageous in that an improvement in curability of the composition and an improvement, for example, in refractive index and etching resistance of the resultant cured product can easily be realized.

As described above, the composition of the tenth embodiment comprises a compound represented by the general formula (1), a compound represented by the general formula (10) and/or a compound represented by the general formula (19). Cured products having a high hardness can easily be obtained from the composition containing this compound.

The content of the compound represented by the general formula (1), the compound represented by the general formula (10) and/or the compound represented by the general formula (19) is preferably 1 to 99% by mass, more preferably 3 to 80% by mass, further more preferably 5 to 70% by mass, relative to the solid content of the composition of the tenth embodiment. The content in the above-defined range is advantageous in that, for example, a coating film forming capability and curability in the composition of the tenth embodiment can easily be improved.

Examples of acid generating agents and base generating agents in the composition of the tenth embodiment include those exemplified in the composition of the seventh embodiment.

The content of the acid generating agent or the base generating agent is preferably 0.5 to 30% by mass, more preferably 1 to 20% by mass, relative to the solid content of the composition of the tenth embodiment. The content in the above-defined range is advantageous in that good curability of the composition can be realized.

Organic solvents exemplified in the composition of the first embodiment may be mentioned as organic solvents usable in the composition of the tenth embodiment.

The content of the organic solvent is such that the solid content concentration of the composition of the tenth embodiment is preferably 1 to 50% by mass, more preferably 5 to 30% by mass.

Method for Preparing Composition

The composition according to the present invention is prepared by mixing the above components with a stirrer. The prepared composition may be filtered, for example, through a membrane filter to render the composition homogeneous.

Cured film, insulating film, color filter, display device, optical member

Cured films, insulating films, and color filters can be formed using the composition according to the present invention.

For example, transparent cured films or insulating films can be obtained by forming a coating film using a coloring agent-free composition and heating the coating film. When such a composition is a negative-type photosensitive resin composition, transparent cured film and insulating film can be obtained by exposing the coating film to electromagnetic waves. The cured film and the insulating film formed using the composition according to the present invention are used, for example, as alignment films and flattening films (for example, alignment films and flattening films for use, for example, in liquid crystal displays or organic EL displays) or as resist underlying films such as antireflection films, interlayer insulating films, and carbon hard masks.

When a negative-type photosensitive resin composition is used as the composition according to the present invention, the cured film and the insulating film may be patterned. Patterned cured film and insulating film can be obtained by exposing the coating film in a predetermined pattern to electromagnetic waves and developing the exposed film. The patterned cured film is used, for example, as spacers and partition walls of liquid crystal displays and organic EL displays.

Further, for example, pixels and black matrix for color filters of liquid crystal displays can also be formed by forming a coating film using a negative-type photosensitive resin composition (particularly the composition of the first embodiment that when it is a negative-type photosensitive resin composition) containing a coloring agent, exposing the coating film in a predetermined pattern to electromagnetic waves and developing the exposed film.

The cured film, the insulating film, and the color filter can be used in display devices. That is, the display device comprises the cured film, the insulating film, and the color filter. For example, liquid crystal displays and organic EL displays may be mentioned as the display device.

Lenses (for example, microlenses) and optical members such as optical fibers, light waveguides, prism sheets, holograms, high refractive index films, and retroreflection films can be obtained by molding the composition according to the present invention and then heating the molded product. When the composition is a negative-type photosensitive resin composition, the optical members can also be obtained by molding the negative-type photosensitive resin composition and then exposing the molded product to electromagnetic waves.

In addition, the energy-sensitive composition comprising the compound represented by the general formula (1), the compound represented by the general formula (10) and/or the compound represented by the general formula (19), and an acid generating agent or a base generating agent, when the acid generating agent and the base generating agent are a photoacid generating agent and a photobase generating agent, respectively, is cured by electromagnetic wave irradiation. When the acid generating agent and the base generating agent are a thermal acid generating agent and a thermal base generating agent, respectively, the energy-sensitive composition is cured by heating. Molded products formed of cured products of the energy-sensitive composition are very low in moisture permeability. Thus, a low-moisture-permeable film can be obtained by subjecting a coating film of the energy-sensitive composition to electromagnetic wave irradiation or heating. The low-moisture-permeable film can be used as water vapor barrier layers.

The composition according to the present invention can also be used as optical materials and semiconductor materials.

Pattern Forming Method

When the composition according to the present invention is a negative-type photosensitive resin composition, the composition is suitable for use in pattern forming methods. The pattern forming method comprises forming a coating film or a molded product using the negative-type photosensitive resin composition, exposing the coating film or the molded product to electromagnetic waves in a predetermined pattern, and developing the exposed coating film or molded product.

More specifically, first, a coating film or a molded product is formed by a suitable coating method or molding method. For example, the composition may be coated with a contact transfer-type coating applicator such as a roll coater, reverse coater, bar coater and the like, or a non-contact type coating applicator such as a spinner (a rotary coating applicator), curtain flow coater and the like, and dried to form the coating film. The drying method is not particularly limited, and for example, (1) a method of carrying out prebaking for 60 to 120 seconds on a hot plate at a temperature of 80 to 120° C., preferably 90 to 100° C., (2) a method of leaving at room temperature for several hours to several days, or (3) a method of inserting into a warm air heater or infrared ray heater for several tens of minutes to several hours and removing the solvent, and the like may be mentioned.

Next, the coating film or molded product is irradiated with electromagnetic waves in a predetermined pattern for exposure. The electromagnetic waves may be applied through a negative-type mask, or may be directly applied. The exposure differs depending on the composition of the composition, but for example, about 5 to 500 mJ/cm$^2$ is preferable.

Next, the coating film or molded product after the exposure is developed with a developing solution to pattern it into the desired shape. The developing method is not particularly limited, and for example, it is possible to use an immersion method or a spray method or the like. Examples of the developing solution include an organic solution such as monoethanol amine, diethanol amine, triethanol amine; and an aqueous solution of a sodium hydroxide, potassium hydroxide, sodium carbonate, ammonia, quaternary ammonium salt, or the like.

For the pattern after the development, it is preferable to carry out post-baking at about 200 to 250° C.

EXAMPLES

Hereinafter, the present invention will be described more specifically with examples, but the scope of the present invention is not limited to these examples.

Compounds Represented by Formula (1) and Comparative Compounds

Compounds 1 to 3 represented by the following formulae were provided as the compounds represented by the general formula (1). Further, for comparison, Comparative Compounds 1 to 6 represented by the following formulae were provided.

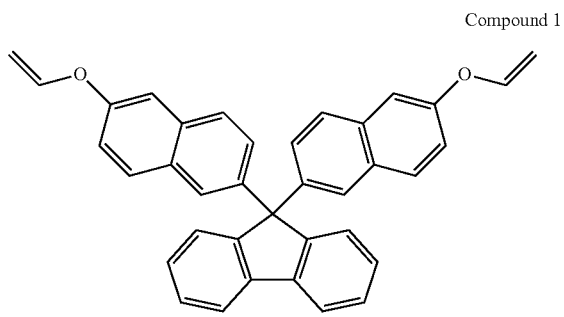

Compound 1

Compound 2

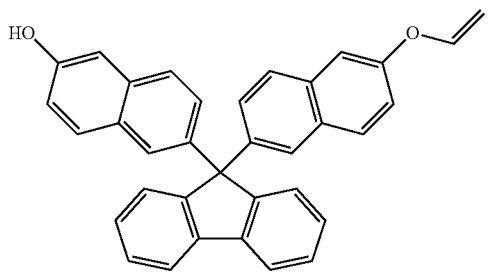

Compound 3

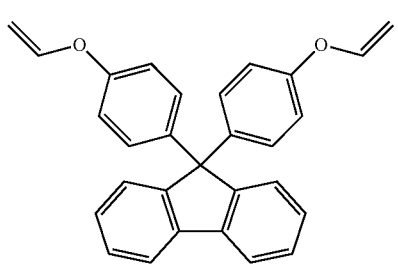

Comparative compound 1

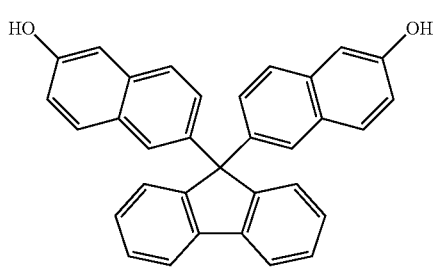

Comparative compound 2

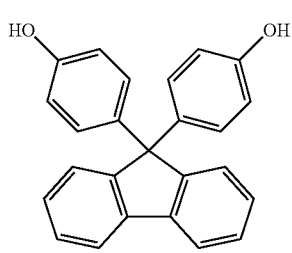

Comparative compound 3

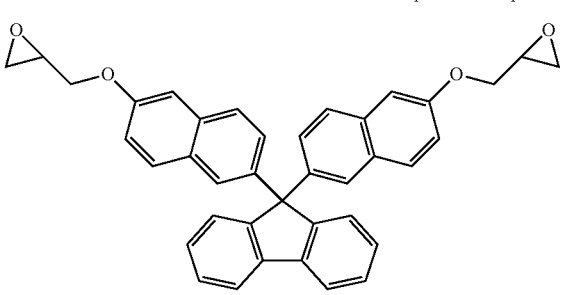

Comparative compound 4

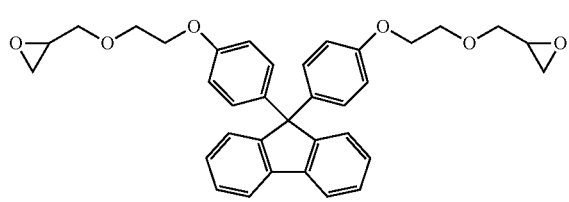

Comparative compound 5

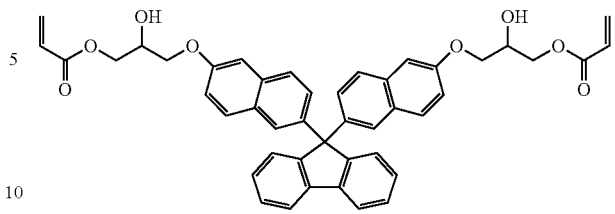

Comparative compound 6

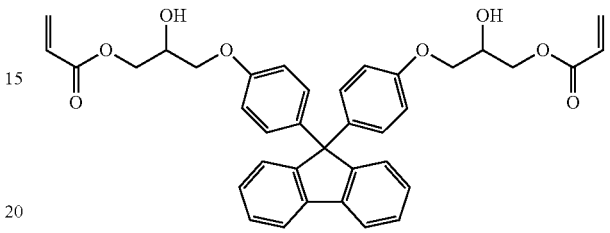

Synthesis methods for Compounds 1 to 3 will be described below (Synthesis Examples 1 to 3). Materials used in the Synthesis Examples were as follows.

[Inorganic Base]
(1) Light Ash Sodium Carbonate
Particle Diameter Distribution:
250 μm or more; 3% by weight
150 μm or more to less than 250 μm; 15% by weight
75 μm or more to less than 150 μm; 50% by weight
Less than 75 μm; 32% by weight The particle diameter distribution was determined by sieving particles with sieves of 60 meshes (250 μm), 100 meshes (150 μm), and 200 meshes (75 μm) and measuring the weight of oversize particles and undersize particles.

[Transition Element Compound Catalyst]
(1) Di-μ-chlorobis(1,5-cyclooctadiene)diiridium(I):[Ir(cod)Cl]$_2$

[Hydroxy Compound]
(1) 9,9'-Bis(6-hydroxy-2-naphthyl)fluorene
(2) 9,9'-Bis(4-hydroxyphenyl)fluorene

[Vinyl Ester Compound]
(1) Vinyl propionate

[Synthesis Example 1] Synthesis of Compound 1

A 1000-ml reaction vessel equipped with a cooling pipe and a decanter that conducts separation of a condensate and returns an organic layer to the reaction vessel and discharges a water layer to the outside of the system was charged with di-μ-chlorobis(1,5-cyclooctadiene)diiridium(I) [Ir(cod)Cl]$_2$ (839 mg, 1.25 mmol), light ash sodium carbonate (12.7 g, 0.12 mol), 9,9'-bis(6-hydroxy-2-naphthyl)fluorene (225 g, 0.5 mol), vinyl propionate (125 g, 1.25 mol), and toluene (300 ml). Thereafter, the temperature of the system was gradually raised while stirring with a stirring blade having a surface area of 10 cm$^2$ at a rotation speed of 250 rpm, followed by reflux. A reaction was allowed to proceed for 5 hrs under reflux while removing water produced as by-product with the decanter. The reaction solution was analyzed by gas chromatography. As a result, it was found that the conversion rate of 9,9'-bis(6-hydroxy-2-naphthyl)fluorene was 100%, and 9,9'-bis(6-vinyloxy-2-naphthyl)fluorene (Compound 1) and bis-6-naphthofluorene monovinyl ether were produced at yields of 81% and 4%, respectively, based on 9,9'-bis(6-hydroxy-2-naphthyl)fluorene.

¹H-NMR (CDCl₃): 4.47 (dd, 2H, J=1.5 Hz, 5.0 Hz), 4.81 (dd, 2H, J=3.5 Hz, 12.0 Hz), 6.71 (dd, 2H, J=6.0 Hz), 7.12-7.82 (m, 20H)

[Synthesis Example 2] Synthesis of Compound 2 (Isolation)

The reaction product obtained in Synthesis Example 1 was subjected to separation and purification by silica gel column chromatography to isolate bis-6-naphthofluorene monovinyl ether (Compound 2).

¹H-NMR (CDCl₃): 4.55 (dd, 1H, J=6.0 Hz), 4.88 (dd, 1H, J=3.5 Hz), 6.79 (dd, 1H, J=6.0 Hz, 14.0 Hz), 7.20-7.89 (m, 20H)

[Synthesis Example 3] Synthesis of Compound 3

A 1000-ml reaction vessel equipped with a cooling pipe and a decanter that conducts separation of a condensate and returns an organic layer to the reaction vessel and discharges a water layer to the outside of the system was charged with di-μ-chlorobis(1,5-cyclooctadiene)diiridium(I) [Ir(cod)Cl]₂ (839 mg, 1.25 mmol), light ash sodium carbonate (12.7 g, 0.12 mol), 9,9'-bis(4-hydroxyphenyl)fluorene (186 g, 0.5 mol), vinyl propionate (125 g, 1.25 mol), and toluene (300 ml). Thereafter, the temperature of the system was gradually raised while stirring with a stirring blade having a surface area of 10 cm² at a rotation speed of 250 rpm, followed by reflux. A reaction was allowed to proceed for 5 hrs under reflux while removing water produced as by-product with the decanter. The reaction solution was analyzed by gas chromatography. As a result, it was found that the conversion rate of 9,9'-bis(4-hydroxyphenyl)fluorene was 100%, and 9,9'-bis(4-vinyloxyphenyl)fluorene (Compound 3) and bis-4-phenolfluorene monovinyl ether were produced at yields of 72% and 9%, respectively, based on 9,9'-bis(4-hydroxyphenyl)fluorene.

¹H-NMR (CDCl₃): 4.47 (dd, 2H), 4.81 (dd, 2H), 6.71 (dd, 2H), 7.12-7.82 (m, 16H)

Evaluation

Compounds 1 and 3 and Comparative Compounds 1 to 6 were dissolved in propylene glycol monomethyl ether acetate to prepare solutions having a concentration of 20% by mass. The solutions were coated with a spin coater on a glass substrate, and the coatings were prebaked at 100° C. for 120 sec to form dried coatings (coating thickness 2.0 μm). The dried coatings were postbaked at 230° C. for 20 min to obtain cured films (film thickness 1.7 μm).

In order to evaluate the reactivity of Compounds 1 and 3 and Comparative Compounds 1 to 6, the pencil hardness was measured according to JIS K 5400 for the cured films. The higher the pencil hardness, the higher the reactivity of the compound. For the cured films (for the dried coatings when the cured film was not obtained), a light transmittance at a wavelength of 633 nm and a refractive index were measured as optical parameters. Further, in order to evaluate the heat resistance of the cured films, the cured films were heated from room temperature (about 20° C.) at a temperature rise rate of 10° C. per min to conduct a thermogravimetric analysis in the air. In the thermogravimetric analysis, a temperature at which the mass was reduced by 5% based on the mass of the cured films at the start of the analysis, $T_{d\,5\%}$ was measured. The results of measurement are shown in Table 1.

TABLE 1

|  | Pencil hardness | Light transmittance | Refractive index | $T_{d\,5\%}$ (° C.) |
|---|---|---|---|---|
| Compound 1 | 7 H | 98% | 1.74 | 357 |
| Compound 3 | 6 H | 98% | 1.65 | 335 |
| Comparative compound 1 | Uncured | 90% | 1.72 | — |
| Comparative compound 2 | Uncured | 94% | 1.63 | — |
| Comparative compound 3 | 5 H | 97% | 1.69 | 400 |
| Comparative compound 4 | 4 H | 97% | 1.59 | 376 |
| Comparative compound 5 | 2 H | 88% | 1.67 | 396 |
| Comparative compound 6 | 3 H | 92% | 1.57 | 389 |

As is apparent from Table 1, the cured films obtained from Compounds 1 and 3 had a high pencil hardness, and these compounds had a high reactivity. For the cured films obtained from Compounds 1 and 3, the light transmittance met a value of not less than 98% that is required of recent functional membranes, and the refractive index and the heat resistance were good.

On the other hand, the cured films obtained from Comparative Compounds 1 to 6 had a lower pencil hardness than the cured films obtained from Compounds 1 and 3, and Comparative Compounds 1 to 6 had an inferior reactivity. Further, the cured films obtained from Comparative Compounds 1 to 6 were inferior in light transmittance to the cured films obtained from Compounds 1 and 3.

Synthesis Examples Through Leaving Group-Containing Compounds

Synthesis Example 4

6,6'-(9-Fluorenylidene)-bis(2-naphthyloxyethanol) (598 g, 1.11 mol), pyridine (87.8 g, 1.11 mol), and dipropylene glycol dimethyl ether (1670 mL) were added to a 5-L reactor, the atmosphere of the system was replaced by nitrogen, and the temperature was raised to 60° C. Thionyl chloride (395.9 g, 3.33 mol) was added dropwise over a time period of 3 hrs, followed by ripening for 2 hrs. The reaction solution was cooled to 30° C., water was added to stop the reaction, and methanol was added dropwise at a temperature in the range of 15 to 20° C. to obtain a target compound with the hydroxyl group replaced by chlorine at a yield of 96% (compound represented by the following formula; the compound being referred to also as Compound 4).

¹H-NMR (CDCl₃): 3.85 (t, 4H, J=6.0 Hz), 4.31 (t, 4H, J=6.0 Hz), 7.08-7.82 (m, 20H)

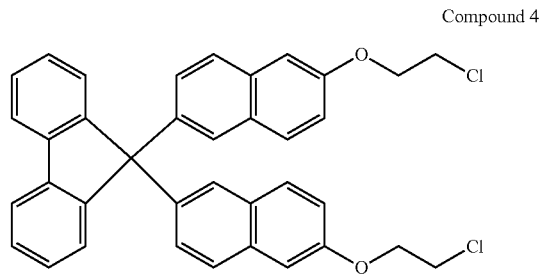 [SMILES: ClCCOc1ccc2cc(C3(c4ccc5cc(OCCCl)ccc5c4)c4ccccc4-c4ccccc43)ccc2c1]

Compound 4

Synthesis Example 5

A solution of potassium-t-butoxide (327.5 g, 2.92 mol) in tetrahydrofuran (1260 mL) was added dropwise at a temperature in the range of 20° C. to 40° C. to a 5-L reactor that had been charged with Compound 4 (560 g, 0.97 mol) and tetrahydrofuran (1260 mL). The reaction solution was ripended at 60° C. for 2 hrs. Water was added to stop the reaction. The organic layer was separated and concentrated in an evaporator to a weight that was twice larger than the charged amount of Compound 4. The concentrate was added dropwise to methanol to obtain 9,9'-bis(6-vinyloxy-2-naphthyl)fluorene (compound represented by the following formula, that is, Compound 1) as a white or grayish white solid at a yield of 77%.

$^1$H-NMR (CDCl$_3$): 4.48 (dd, 2H, J=1.5 Hz, 6.5 Hz), 4.81 (dd, 2H, J=1.5 Hz, 13.5 Hz), 6.73 (dd, 2H, J=6.5 Hz, 13.5 Hz), 7.13-7.83 (m, 20H)

Compound 1

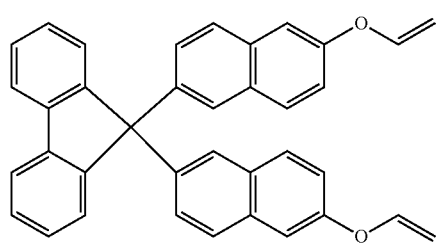

Synthesis Example 6

Ethylene glycol (1.00 g, 0.0161 mol), triethylamine (3.42 g, 0.0338 mol), and tetrahydrofuran (3.38 mL) were added to a 25-mL reactor. The atmosphere of the reactor was replaced by nitrogen, and the system was cooled to 0° C. Methanesulfonyl chloride (3.88 g, 0.0338 mol) was added dropwise over a time period of 2 hrs. The reaction solution was ripened for one hr, and water was added to stop the reaction. Ethyl acetate was added, the organic layer was separated, and the solvent was removed by evaporation in an evaporator to obtain a compound that was ethylene glycol with a methanesulfonyl group added thereto (compound represented by the following formula; at a yield of 80%; hereinafter referred to also as "EG-DMs")

$^1$H-NMR (CDCl$_3$): 3.10 (s, 6H), 4.47 (s, 4H)

EG-DMs

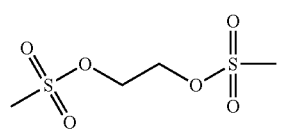

Synthesis Example 7

6,6-(9-Fluorenylidene)-2,2-dinaphthol (compound represented by the following formula represented on the left side; 1.00 g, 0.0022 mol; hereinafter referred to also as "Compound 5"), potassium carbonate (0.64 g, 0.0047 mol), and tetrahydrofuran (3.38 mL) were added to a 25-mL reactor. The atmosphere of the reactor was replaced by nitrogen. A solution of EG-DMs (1.02 g, 0.0047 mol) synthesized in Synthesis Example 6 in tetrahydrofuran (1.12 mL) was added at room temperature, the mixture was heated to 60° C., and the reaction solution was ripened for 15 hrs. The reaction solution was analyzed by HPLC. As a result, it was found that Compound 6 (compound represented by the following formula represented on the right side) was synthesized at a conversion of Compound 5 of 99% and a selectivity of 65%.

(Compound 6) $^1$H-NMR (CDCl$_3$): 3.08 (s, 6H), 4.32 (t, 4H, J=4.4 Hz), 4.60 (t, 4H, J=4.4 Hz), 7.05-7.83 (m, 20H)

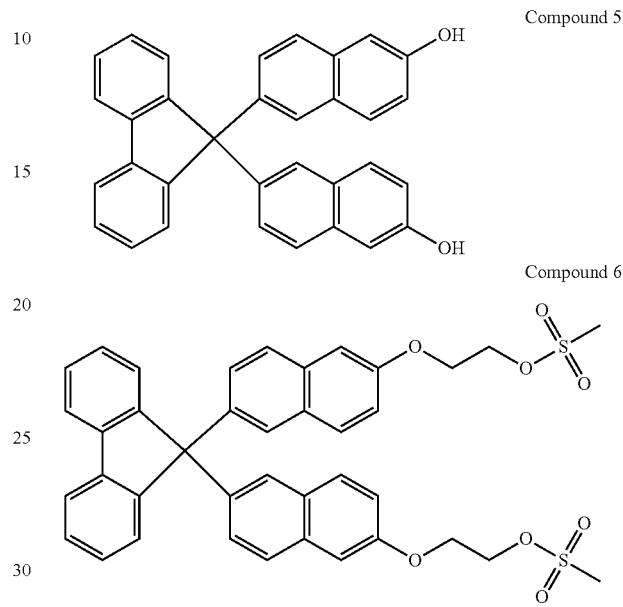

Synthesis Example 8

A solution of potassium-t-butoxide (1.45 g, 0.0130 mol) in tetrahydrofuran (2.25 mL) was added dropwise at a temperature in the range of 20° C. to 40° C. to a 25-mL reactor charged with Compound 6 (2.00 g, 0.00288 mol), dipropylene glycol dimethyl ether (2.25 mL). The reaction solution was ripened at 100° C. for 2 hrs. The reaction solution was analyzed by HPLC. As a result, it was found that Compound 1 was synthesized at a conversion rate of Compound 6 of 99% and a selectivity of 58% and a monovinyl monomesyl compound (compound represented by the following formula; hereinafter referred to also as "Compound 7") was synthesized at a selectivity of 32%.

$^1$H-NMR (CDCl$_3$): 3.10 (s, 3H), 4.34 (t, 2H, J=3.6 Hz), 4.49 (dd, 1H, J=1.2 Hz, 5.2 Hz), 4.62 (t, 2H, J=3.6 Hz), 4.81 (dd, 1H, J=1.2 Hz, 11.2 Hz), 6.73 (dd, 1H, J=5.2 Hz, 11.2 Hz), 7.06-7.83 (m, 20H)

Compound 7

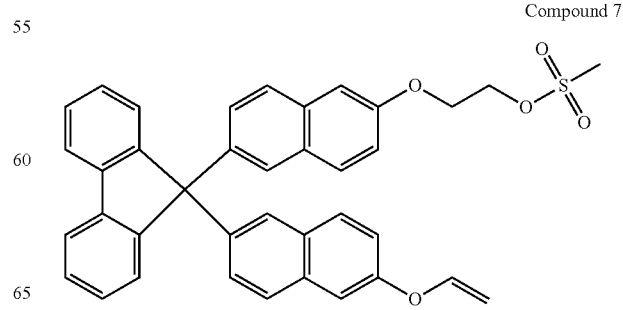

Synthesis Example 9

2-Chloroethanol (3.00 g, 0.048 mol), triethylamine (5.87 g, 0.058 mol), and tetrahydrofuran (10.12 mL) were added to a 50-mL reactor. The atmosphere in the reactor was replaced by nitrogen. Thereafter, the reaction solution was cooled to 0° C. Methanesulfonyl chloride (6.09 g, 0.053 mol) was added dropwise over a time period of 2 hrs. The reaction solution was ripened for one hr. Water was added to stop the reaction. Ethyl acetate was added, the organic layer was separated, and the solvent was removed by evaporation in an evaporator to obtain a compound that was 2-chloroethanol with a methanesulfonyl group added thereto (compound represented by the following formula; hereinafter referred to also as "ClEMs") at a yield of 80%.

$^1$H-NMR (CDCl$_3$): 3.09 (s, 3H), 3.77 (t, 2H, J=5.5 Hz), 4.45 (t, 2H, J=5.5 Hz)

ClEMs

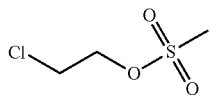

Synthesis Example 10

Compound 5 (1.00 g, 0.0022 mol), potassium carbonate (0.64 g, 0.0047 mol), and dipropylene glycol dimethyl ether (2.23 mL) were added to a 25-mL reactor. The atmosphere in the reactor was replaced by nitrogen. A solution of ClEMs (1.06 g, 0.0067 mol) in dipropylene glycol dimethyl ether (1.12 mL) was added at room temperature. The mixture was heated to 60° C., and the reaction mixture was ripened for 15 hrs. The reaction solution was analyzed by HPLC. As a result, it was found that Compound 4 was synthesized at a conversion of Compound 5 of 17% and a selectivity of 4% and Compound 8 (compound represented by the following formula) was synthesized at a selectivity of 12%.

$^1$H-NMR (CDCl$_3$): 3.86 (t, 2H, J=6.0 Hz), 4.32 (t, 2H, J=6.0 Hz), 7.09-7.82 (m, 20H)

Compound 8

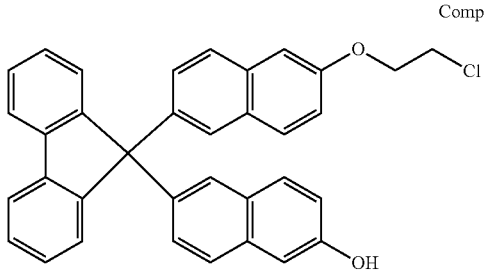

Synthesis Example 11

A solution of potassium-t-butoxide (0.58 g, 0.0052 mol) in tetrahydrofuran (6.8 mL) was added dropwise at a temperature in the range of 20° C. to 40° C. to a 25-mL reactor charged with Compound 4 (3.0 g, 0.0052 mol) and tetrahydrofuran (6.8 mL). The reaction solution was ripened at 60° C. for 2 hrs. Water was then added to stop the reaction. The organic layer was analyzed by HPLC. As a result, it was found that Compound 1 was synthesized at a conversion of Compound 4 of 57% and a selectivity of 25% and a monovinyl monochloro compound (compound represented by the following formula; hereinafter referred to also as "Compound 9") was synthesized at a selectivity of 75%.

$^1$H-NMR (CDCl$_3$): 3.84 (t, 2H, J=6.0 Hz), 4.30 (t, 2H, J=6.0 Hz), 4.48 (dd, 1H, J=1.6 Hz, 6.0 Hz), 4.81 (dd, 1H, J=1.6 Hz, 13.6 Hz), 6.72 (dd, 1H, J=6.0 Hz, 13.6 Hz), 7.08-7.82 (m, 20H)

Compound 9

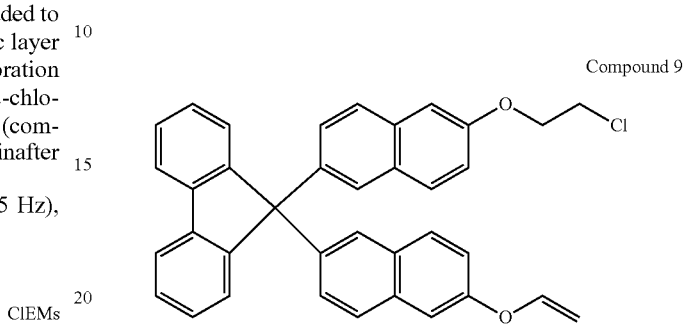

Synthesis Example 12

9,9'-Bis(4-(2-hydroxyethoxy)phenyl)fluorene (6.26 g, 0.0143 mol), pyridine (2.82 g, 0.0357 mol), dipropylene glycol dimethyl ether (33.4 mL), and tetrahydrofuran (33.7 mL) were added to a 200-mL reactor. The atmosphere in the reactor was replaced by nitrogen. The reaction solution was heated to 60° C. Thionyl chloride (6.79 g, 0.0571 mol) was added dropwise over a time period of 2 hrs. The reaction solution was then ripened for 2 hrs. After cooling to 30° C., water was added to stop the reaction, and methanol was added dropwise at a temperature in the range of 15 to 20° C. to obtain a target compound in which the hydroxyl group was replaced with chlorine (compound represented by the following formula; hereinafter referred to also as "Compound 10") at a yield of 95%.

$^1$H-NMR (CDCl$_3$): 3.75 (t, 4H, J=6.0 Hz), 4.14 (t, 4H, J=6.0 Hz), 6.73-7.75 (m, 16H)

Compound 10

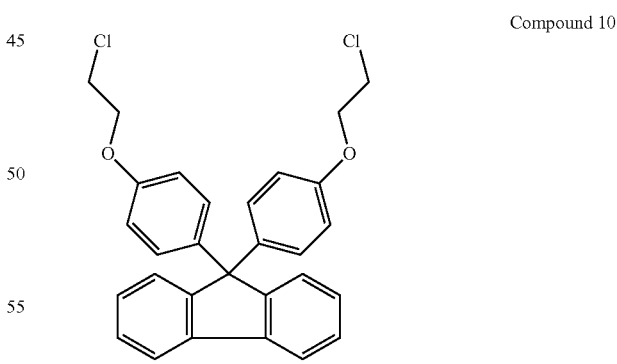

Synthesis Example 13

A solution of potassium-t-butoxide (3.53 g, 0.0315 mol) in tetrahydrofuran (13.6 mL) was added dropwise at a temperature in the range of 20° C. to 40° C. to a 100-mL reactor charged with Compound 10 (5.0 g, 0.0105 mol) and tetrahydrofuran (11.5 mL). The reaction solution was ripened at 60° C. for 2 hrs. Water was then added to stop the reaction. The organic layer was concentrated in an evaporator to a weight that was twice larger than the charged amount of Compound 10. The concentrate was added dropwise to methanol to obtain 9,9'-bis(4-vinyloxyphenyl)fluorene (compound represented by the following formula, that is, Compound 3), as a white or grayish white solid at a yield of 79%.

$^1$H-NMR (CDCl$_3$): 4.47 (dd, 2H), 4.81 (dd, 2H), 6.71 (dd, 2H), 7.12-7.82 (m, 16H)

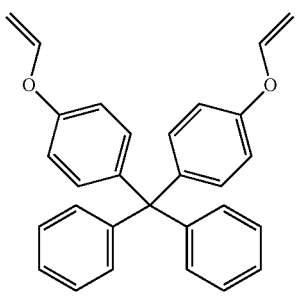

Compound 3

Compounds Represented by General Formula (19)

Synthesis Example 14

Compound 5 (3.00 g, 0.00666 mol), triethylamine (1.48 g, 0.0146 mol), phenothiazine (9.00 mg, 0.0000452 mol), and tetrahydrofuran (16.9 mL) were added to a 50-mL reactor. The atmosphere in the reactor was replaced by nitrogen. The reaction solution was cooled to 0° C. Acryloyl chloride (1.51 g, 0.0166 mol) was added dropwise over a time period of one hr, and the reaction solution was ripened for 2 hrs. Water was added to stop the reaction, and the organic layer was separated. The solvent was removed by evaporation in an evaporator, and the residue was then purified by silica gel column chromatography to obtain a target diacryl compound (compound represented by the following formula; hereinafter referred to also as "Compound 11") as a white solid at a yield of 63%.

$^1$H-NMR (CDCl$_3$): 6.03 (dd, 2H, J=1.5 Hz, 10.0 Hz), 6.36 (dd, 2H, J=10.0 Hz, 17.5 Hz), 6.63 (dd, 2H, J=1.5 Hz, 17.5 Hz), 7.19-7.84 (m, 20H)

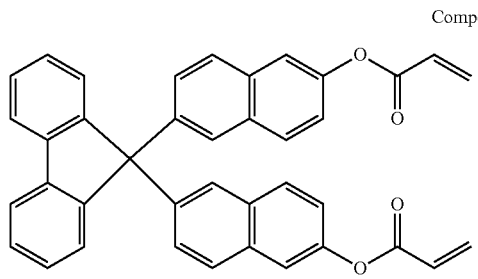

Compound 11

Synthesis Example 15

Compound 5 (3.00 g, 0.00666 mol), triethylamine (1.48 g, 0.0146 mol), phenothiazine (9.00 mg, 0.0000452 mol), and tetrahydrofuran (16.9 mL) were added to a 50-mL reactor. The atmosphere in the reactor was replaced by nitrogen. The reaction solution was then cooled to 0° C. Methacryloyl chloride (1.74 g, 0.0166 mol) was added dropwise over a time period of one hr, and the reaction solution was then gradually heated to 40° C. and ripened for 2 hrs. Water was added to stop the reaction, and the organic layer was separated. The solvent was removed by evaporation in an evaporator, and the residue was purified by silica gel column chromatography to obtain a target dimethacryl compound (compound represented by the following formula; hereinafter referred to also as "Compound 12") as a white solid at a yield of 73%.

$^1$H-NMR (CDCl$_3$): 2.08 (s, 6H), 5.77 (s, 2H), 6.38 (s, 2H), 7.18-7.84 (m, 20H)

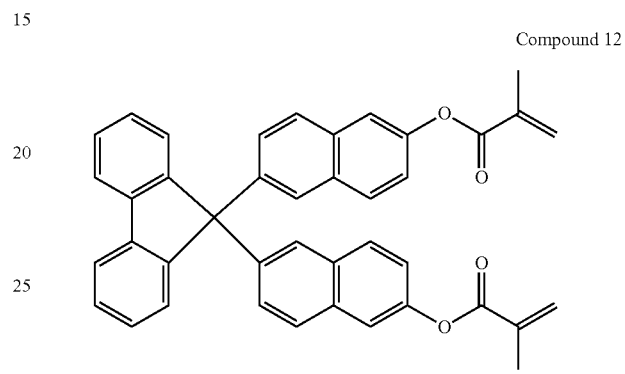

Compound 12

Purification of Compounds Represented by General Formula (1)

Compound 1 obtained in Synthesis Example 5 was purified by silica gel column chromatography. The purity of Compound 1 before the purification and Compound 1 after the purification (proportion of Compound 1 in the total of Compound 1 and impurities) was measured by HPLC with ultraviolet light at 220 nm. Further, the content of a metallic component in Compound 1 before the purification and the content of the metallic component in Compound 1 after the purification were measured by ICP-MS (inductive coupling plasma emission-mass spectroscopic analysis method). The results are shown in Table 2.

Evaluation

Each of the Compound 1 before the purification and the Compound 1 after the purification was dissolved in tetrahydrofuran to prepare a 10 mass % solution. The solution was cooled to −30° C. A catalytic amount of boron trifluoride was added to the solution to prepare a reaction solution. The temperature of the reaction solution was raised from −30° C. at a rate of 2° C./min, and a vinyl group reduction start temperature was monitored by infrared spectroscopy to measure the start temperature of a reaction of Compounds 1, followed by evaluation according to the following criteria. The reaction system was visually inspected for coloring. The results are shown in Table 2. Evaluation criteria for reaction start temperature S: The reaction start temperature was 0° C. or below.

A: The reaction start temperature was above 0° C. to 20° C. or less.

B: The reaction start temperature was above 20° C.

TABLE 2

| | Purity | Content of metallic component (mass ppm) | | | | | (Reaction start temp.) | Coloring |
|---|---|---|---|---|---|---|---|---|
| | (mass %) | Na | K | Fe | Cu | Ca | | |
| Compound 1 before purification | 92.1 | 500 | 35 | <15 | <15 | <1.5 | B | Present |
| Compound 1 after purification | 98.5 | <0.05 | <0.1 | <15 | <15 | <1.5 | A | Absent |

As is apparent from Table 2, as a result of purification by silica gel column chromatography, it was confirmed that the Compound 1 had an improved purity and had a reduced metallic component content, particularly a reduced content in sodium component and potassium component. Further, it was confirmed that the purification lowered the start temperature of the reaction of the Compounds 1, contributing to an improved reactivity of the Compounds 1. Furthermore, it was confirmed that the coloring in the reaction could be suppressed by the purification.

Preparation of Negative-Type Photosensitive Resin Composition

Example 1

The following components were added to a mixed solvent of 3-methoxybutyl acetate (MA)/tetramethylurea (TMU)/propylene glycol monomethyl ether acetate (PM)=55/10/35 (mass ratio). The mixture was mixed with a stirrer for one hr and filtered through a 5-μm membrane filter to prepare a negative-type photosensitive resin composition having a solid content concentration of 15% by mass as a filtrate.

Alkali-soluble resin
  Resin (R-1) (solid content 55%, solvent: 3-methoxybutyl acetate) . . . 60 parts by mass
Photopolymerizable monomer
  Dipentaerythritol hexaacrylate (DPHA, manufactured by Nippon Kayaku Co., Ltd.) . . . 20 parts by mass
Photopolymerization initiator
  "OXE-02" (tradename: manufactured by BASF) . . . 10 parts by mass
Compound represented by general formula (1)
  Compound 1 . . . 10 parts by mass
Colorant
  Carbon dispersion "CF black" (tradename: manufactured by Mikoku Color Ltd., solid content 25%, solvent: 3-methoxybutyl acetate) . . . 400 parts by mass The resin (R-1) was synthesized by the following method.
First, a 500-mL four-necked flask was charged with 235 g of a bisphenolfluorene epoxy resin (epoxy equivalent 235), 110 mg of tetramethyl ammonium chloride, 100 mg of 2,6-di-tert-butyl-4-methylphenol, and 72.0 g of acrylic acid. The contents were heat-dissolved at 90 to 100° C. while blowing air thereinto at a rate of 25 ml/min. Next, in such a state that the solution was cloudy, the solution was gradually heated to 120° C. for full dissolution. In this case, the solution gradually became transparent and viscous but was continued to be stirred. In this period, the acid value was measured, and heating with stirring was continued until the acid value reached less than 1.0 mg KOH/g. A time period of 12 hrs was necessary for the acid value to reach a target value. The solution was then cooled to room temperature to obtain a bisphenolfluorene epoxy acrylate that was colorless, transparent and solid and represented by the following formula (r-4).

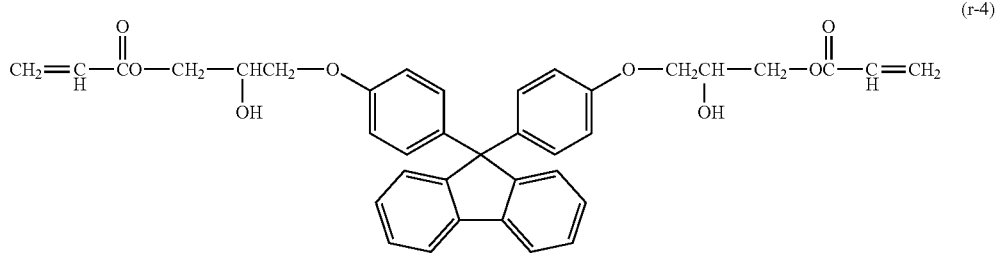

(r-4)

Next, 600 g of 3-methoxybutyl acetate was added to and dissolved in 307.0 g of the bisphenolfluorene epoxy acrylate. 80.5 g of benzophenone tetracarboxylic acid dianhydride and 1 g of tetraethylammonium bromide were mixed into the solution. The mixture was gradually heated, and a reaction was allowed to proceed at 110 to 115° C. for 4 hrs. After the disappearance of an acid anhydride group, 38.0 g of 1,2,3,6-tetrahydro phthalic anhydride was mixed thereinto, and a reaction was allowed to proceed at 90° C. for 6 hrs to obtain a resin (R-1). The disappearance of the acid anhydride group was confirmed by an IR spectrum.

The resin (R-1) corresponds to a compound represented by the general formula (r-1).

Example 2 and Comparative Examples 1 to 6

In Example 2 and Comparative Examples 1 to 6, negative-type photosensitive resin compositions were prepared in the same manner as in Example 1, except that Compound 3 and Comparative Compounds 1 to 5 were used instead of Compound 1. Further, in Comparative Example 1, a negative-type photosensitive resin composition was prepared in the same manner as in Example 1, except that Compound 1 was not used.

Evaluation

Negative-type photosensitive resin compositions of Examples 1 and 2 and Comparative Examples 1 to 6 were coated using a spin-coater on a glass substrate (100 mm×100 mm), and the coatings were prebaked at 90° C. for 120 sec to form coatings having a thickness of 1.0 μm. Next, the coatings were irradiated with ultraviolet light using a mirror projection aligner (product name: TME-150RTO, manufactured by Topcon Corp.) at an exposure gap of 50 μm through a negative mask with a line pattern of 5, 10, 15, and 20 μm formed therein. The exposure was 10 mJ/cm². After exposure, the coating films were developed with a 0.04 mass % aqueous KOH solution at 26° C. for 40 sec and postbaked at 230° C. for 30 min to form line patterns.

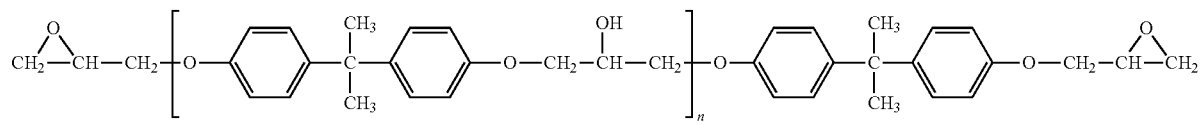

The line patterns thus formed were observed under an optical microscope to evaluate pattern adhesion. The pattern adhesion was evaluated as "good" when the line pattern was formed without separation from the substrate; and was evaluated as "none" (unacceptable) when the line pattern was not formed due to separation from the substrate.

The results are shown in Table 3 below.

TABLE 3

|  | Compound of formula (1) or comparative compound | Pattern adhesion | | | |
| --- | --- | --- | --- | --- | --- |
|  |  | 5 μm | 10 μm | 15 μm | 20 μm |
| Example 1 | Compound 1 | Good | Good | Good | Good |
| Example 2 | Compound 3 | Good | Good | Good | Good |
| Comparative Example 1 | — | No adhesion | No adhesion | Good | No adhesion |
| Comparative Example 2 | Comparative compound 1 | No adhesion | No adhesion | Good | No adhesion |
| Comparative Example 3 | Comparative compound 2 | No adhesion | Good | No adhesion | No adhesion |
| Comparative Example 4 | Comparative compound 3 | No adhesion | Good | No adhesion | No adhesion |
| Comparative Example 5 | Comparative compound 4 | No adhesion | No adhesion | Good | No adhesion |
| Comparative Example 6 | Comparative compound 5 | No adhesion | No adhesion | Good | No adhesion |

As is apparent from Table 3, when the negative-type photosensitive resin compositions of Examples 1 and 2 containing Compounds 1 and 3 represented by the general formula (1) were used, a 5-μm line pattern was closely adhered to a substrate even at a low exposure of 10 mJ/cm².

On the other hand, when the negative-type photosensitive resin composition of Comparative Example 1 free from the compound represented by the general formula (1), and the negative-type photosensitive resin compositions of Comparative Examples 2 to 6 that were free from the compound represented by the general formula (1) and contained Comparative Compounds 1 to 5 were used, as is apparent from Table 3, the pattern adhesion was inferior to that in Examples 1 and 2 and good micropatterning properties could not be obtained.

Preparation of Compositions Containing Acid Generating Agent or Base Generating Agent Examples 3 to 8 and Comparative Examples 7 to 8

Materials

Compounds Represented by the General Formula (1), or Comparative Compound

Compound 1: Compound 1 obtained in Synthesis Example 1

Compound 3: Compound 3 obtained in Synthesis Example 3

Comparative Compound 7: Compound Represented by the Following Formula

Comparative Compound 8: Compound Represented by the Following Formula

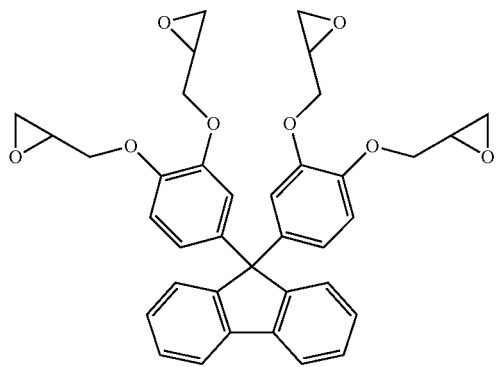 [SMILES: c1ccc2c(c1)-c1ccccc1C2(c1ccc(OCC2CO2)c(OCC2CO2)c1)c1ccc(OCC2CO2)c(OCC2CO2)c1]

Acid Generating Agent or Base Generating Agent

PAG: CPI-210S (tradename, manufactured by SAN-APRO LTD.)

PBG: WPBG-140 (tradename, manufactured by Wako Pure Chemical Industries, Ltd.)

TAG: 2-Nitrobenzyl tosylate (Preparation of Compositions)

0.3 g of an acid generating agent or a base generating agent specified in Table 4 was homogeneously dissolved in 10 g of cyclohexanone, and 10 g of a compound or a comparative compound specified in Table 4 was added to and dissolved in the solution at room temperature to obtain a composition.

Evaluation (Low-Moisture Permeability)

The composition thus obtained was coated with a coater on a glass substrate, and the coating was heated on a hot plate at 100° C. for 120 sec to obtain a coating film. The coating film was exposed to broad band light, and the exposed coating film was heated in an oven at 180° C. for 20 min for curing. Thus, a 10 μm-thick sheet formed of a cured product of the composition was formed. For the sheet that had been cut into a predetermined size, the moisture permeability (g/(m$^2$·24 h)) was measured under the conditions of 60° C., 90% RH, followed by evaluation according to the following criteria. The results are shown in Table 4.

∞: The moisture permeability was less than 30 g/(m$^2$·24 hr), indicating that the low-moisture permeability was very good.

○: The moisture permeability was 30 g/(m$^2$·24 hr) or more to less than 35 g/(m$^2$·24 hr), indicating that the low-moisture permeability was good.

x: The moisture permeability was 35 g/(m$^2$·24 hr) or more, indicating that the low-moisture permeability was poor.

(Light Transmittance)

A 2.0 μm-thick sheet was formed in the same manner as in the evaluation of the low-moisture permeability. The light transmittance of the sheet at 400 nm was measured with a transmissiometer and was evaluated according to the following criteria. The results are shown in Table 4.

∞: The light transmittance was 97% or more, that is, was very good.

○: The light transmittance was 95% or more to less than 97%, that is, was good.

x: The light transmittance was less than 95%, that is, was poor.

(Pressure Cooker Test (PCT))

A 2.0 μm-thick sheet was formed in the same manner as in the evaluation of the low-moisture permeability. According to IEC 68-2-66, the sheet was allowed to stand under an atmosphere of 100° C. and RH120% for 24 hrs, and PCT was carried out. After PCT, the sheet was visually observed and was evaluated according to the following criteria. The results are shown in Table 4.

∞: The sheet had neither separation nor chipping, and the moisture resistance was very good.

○: The sheet had chipping but was free from separation, and the moisture resistance was good.

x: Separation was observed in the sheet, and the moisture resistance was poor.

As is apparent from Table 4, the sheets obtained from the compositions of Examples 3 to 8 containing Compound 1 or 3 represented by the general formula (1) were very good in terms of all of low-moisture permeability, light transmittance, and moisture resistance.

By contrast, the sheet obtained from the composition of Comparative Example 7 that was free from the compound represented by the general formula (1) but contained Comparative Compound 7 was poor in terms of all of low-moisture permeability, light transmittance, and moisture resistance. The sheet obtained from the composition of Comparative Example 8 that was free from the compound represented by the general formula (1) but contained Comparative Compound 8 had good light transmittance and moisture resistance but was poor in terms of low-moisture permeability.

Preparation of Other Various Compositions

Examples 9 to 34

(Material)

Compounds Represented by the General Formula (1)

Compound 1: Compound 1 obtained in Synthesis Example 1

Compound 2: Compound 2 obtained in Synthesis Example 2

Photopolymerizable Monomer

Monofunctional monomer 1: lauryl acrylate

Polyfunctional Monomer 1: dipentaerythritol hexaacrylate (DPHA, manufactured by Nippon Kayaku Co., Ltd.)

Photopolymerization Initiator 1: "OXE-02" (tradename: manufactured by BASF)

Acid generating agent or base generating agent

PAG1: CPI-210S (tradename, manufactured by SANAPRO LTD.)

PBG1: WPBG-140 (tradename, manufactured by Wako Pure Chemical Industries, Ltd.)

Phenol Resin 1: polyhydroxystyrene (mass average molecular weight: 5,000)

Epoxy Compound 1: epoxy compound represented by the following formula

TABLE 4

| | Compound or comparative compound | Acid generating agent or base generating agent | Low-moisture permeability | Light transmittance | PCT (Moisture resistance) |
|---|---|---|---|---|---|
| Example 3 | Compound 1 | P A G | ∞ | ∞ | ∞ |
| Example 4 | Compound 1 | P B G | ∞ | ∞ | ∞ |
| Example 5 | Compound 1 | T A G | ∞ | ∞ | ∞ |
| Example 6 | Compound 3 | P A G | ∞ | ∞ | ∞ |
| Example 7 | Compound 3 | P B G | ∞ | ∞ | ∞ |
| Example 8 | Compound 3 | T A G | ∞ | ∞ | ∞ |
| Comparative Example 7 | Comparative compound 7 | P A G | x | x | x |
| Comparative Example 8 | Comparative compound 8 | P A G | x | ○ | ○ |

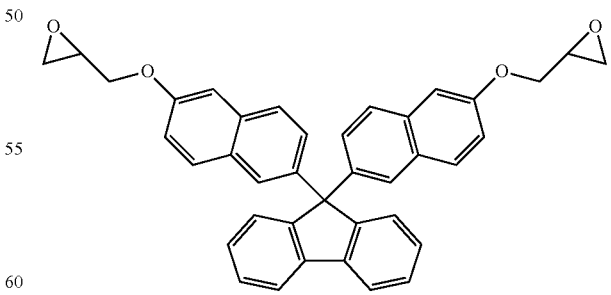

Epoxy Compound 2: Epikote (currently jER) 828 (tradename, bisphenol A epoxy resin, manufactured by Japan Epoxy Resins Co., Ltd. (currently Mitsubishi Chemical Corporation))

Triazine Compound 1: epoxy-group-containing triazine compound represented by the following formula

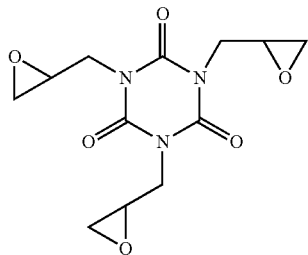 [SMILES: O=c1n(CC2CO2)c(=O)n(CC2CO2)c(=O)n1CC1CO1]

Silicon-containing Compound 1: silanol compound represented by the following formula (wherein m is an integer of 5 to 10) (viscosity 10 cm²/sec)

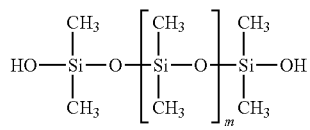

Crystallization Inhibitor 1: KOH
Adhesion Enhancer 1: silane coupling agent represented by the following formula.

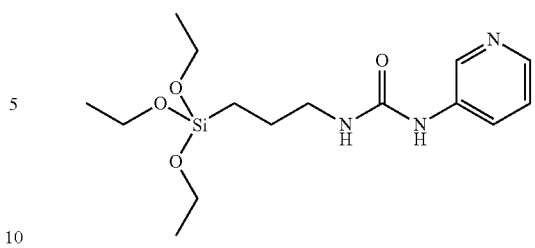

Surfactant 1: BYK-310 (tradename, silicone-based surfactant, manufactured by Byk-Chemie Japan K.K.)
Surfactant 2: APX4082B (tradename, fluorine-based surfactant, manufactured by Kyoeisha Chemical Co., Ltd.)
Inorganic Filler 1: $TiO_2$
Solvent 1: cyclohexanone
Solvent 2: acetic acid (Preparation of Composition)

Individual components of the type and amount (parts by mass) specified in Table 5 were homogeneously mixed together at room temperature to obtain a composition. In Example 9, Monofunctional Monomer 1 was liquid at room temperature and could dissolve Compound 1, and, thus, a liquid composition could be obtained without the addition of a solvent. Further, in Examples 10 to 34, the amount of the solvent was regulated so that the solid content concentration of the composition was 15% by mass.

TABLE 5

| Example | Component 1 Type | Amount | Component 2 Type | Amount | Component 3 Type | Amount | Component 4 Type | Amount | Component 5 (Solvent) |
|---|---|---|---|---|---|---|---|---|---|
| 9 | Compound 1 | 10 | Monofunctional monomer 1 | 20 | — | — | — | — | (Solvent-free) |
| 10 | Compound 1 | 10 | Monofunctional monomer 1 | 20 | Photopolymerization initiator | 10 1 | — | — | Solvent 1 |
| 11 | Compound 1 | 10 | Polyfunctional monomer 1 | 20 | Photopolymerization initiator | 10 1 | — | — | Solvent 1 |
| 12 | Compound 1 | 10 | Polyfunctional monomer 1 | 10 | Monofunctional monomer 1 | 10 | — | — | Solvent 1 |
| 13 | Compound 2 | 10 | Polyfunctional monomer 1 | 20 | Photopolymerization initiator | 10 1 | — | — | Solvent 1 |
| 14 | Compound 2 | 10 | Polyfunctional monomer 1 | 20 | Photopolymerization initiator | 10 1 | Compound 1 | 10 | Solvent 1 |
| 15 | Compound 1 | 10 | Phenol resin 1 | 10 | — | — | — | — | Solvent 1 |
| 16 | Compound 1 | 10 | Phenol resin 1 | 10 | PAG 1 | 1 | — | — | Solvent 1 |
| 17 | Compound 1 | 10 | Phenol resin 1 | 10 | PAG 1 | 1 | Crosslinking agent | 1 | Solvent 1 |
| 18 | Compound 1 | 10 | Epoxy compound 1 | 10 | — | — | — | — | Solvent 2 |
| 19 | Compound 1 | 10 | Epoxy compound 2 | 10 | — | — | — | — | Solvent 2 |
| 20 | Compound 1 | 10 | Epoxy compound 1 | 10 | PAG 1 | 1 | — | — | Solvent 1 |
| 21 | Compound 1 | 10 | Epoxy compound 1 | 10 | PAG 1 | 1 | — | — | Solvent 1 |
| 22 | Compound 1 | 10 | Epoxy compound 1 | 10 | PAG 1 | 1 | — | — | Solvent 2 |
| 23 | Compound 1 | 10 | Triazine compound 1 | 1 | — | — | — | — | Solvent 1 |
| 24 | Compound 1 | 10 | Triazine compound 1 | 1 | PAG 1 | 1 | — | — | Solvent 1 |
| 25 | Compound 1 | 10 | Triazine compound 1 | 1 | PAG 1 | 1 | — | — | Solvent 1 |
| 26 | Compound 1 | 10 | Compound 2 | 10 | — | — | — | — | Solvent 1 |
| 27 | Compound 1 | 10 | Compound 2 | 10 | PAG 1 | 1 | — | — | Solvent 1 |
| 28 | Compound 1 | 10 | Compound 2 | 10 | PAG 1 | 1 | — | — | Solvent 1 |
| 29 | Compound 1 | 10 | Silicon-containing compound 1 | 5 | — | — | — | — | Solvent 1 |
| 30 | Compound 1 | 10 | Crystallization inhibitor 1 | 1 | — | — | — | — | Solvent 1 |

TABLE 5-continued

| Example | Component 1 Type | Component 1 Amount | Component 2 Type | Component 2 Amount | Component 3 Type | Component 3 Amount | Component 4 Type | Component 4 Amount | Component 5 (Solvent) |
|---|---|---|---|---|---|---|---|---|---|
| 31 | Compound 1 | 10 | Adhesion enhancer 1 | 1 | — | | — | — | Solvent 1 |
| 32 | Compound 1 | 10 | Surfactant 1 | 1 | — | | — | — | Solvent 1 |
| 33 | Compound 1 | 10 | Surfactant 2 | 1 | — | | — | — | Solvent 1 |
| 34 | Compound 1 | 10 | Inorganic filler 1 | 5 | — | | — | — | Solvent 1 |

Evaluation
(Pencil Hardness, Refractive Index, and Heat Resistance)

A cured film was obtained from the resultant composition, and, for the cured film, the pencil hardness, refractive index, and heat resistance (5% mass reduction temperature: $T_{d5\%}$) were measured in the same manner as in the evaluation of Compounds 1 and 3 and Comparative Compounds 1 to 6. The results are shown in Table 6.

Curing methods of the compositions are shown in Table 6. In Table 6, "thermal reaction" indicates that a cured film was obtained by heating the composition in the same manner as in the evaluation of Compounds 1 and 3 and Comparative Compounds 1 to 6. On the other hand, in Table 6, "photreaction" indicates that a cured film was obtained by coating a composition on a glass substrate with a coater, heating the coating on a hot plate at 80° C. for 2 min (prebaking), exposing the coating film to broad band light, and heating the exposed coating film on a hot plate at 70° C. for 2 min (PEB).

(Pattern Adhesion)

A 5 μm-line pattern was formed from the composition of Example 13 or 14 in the same manner as in Examples 1 and 2 and Comparative Examples 1 to 6, followed by evaluation of pattern adhesion. The pattern adhesion was evaluated as "good" when the line pattern was formed without separation from the substrate; and was evaluated as "none" (unacceptable) when the line pattern was not formed due to separation from the substrate. The results are shown in Table 6.

(Patterning Properties)

The composition of Example 16 or 17 was coated with a coater onto a glass substrate. The coating was heated on a hot plate at 80° C. for 2 min (prebaking). The coating film after heating was exposed to broad band light. The exposed coating film was heated on a hot plate at 70° C. for 2 min (PEB), and the baked film was developed with a 2.38 mass % aqueous TMAH solution for negative-type patterning.

The film thus obtained was observed under a microscope to inspect whether or not a pattern was formed. When a pattern was formed, the patterning property was determined as good (○), while when a pattern was not formed, the patterning property was determined as poor (x). The results are shown in Table 6.

TABLE 6

| Example | Curing method | Pencil hardness | Refractive index | Heat resistance | Pattern adhesion | Patterning property |
|---|---|---|---|---|---|---|
| 9 | Photoreaction | 6 H | 1.73 | 320 | | |
| 10 | Photoreaction | 7 H | 1.73 | 320 | | |
| 11 | Photoreaction | 7 H | 1.73 | 340 | | |
| 12 | Photoreaction | 7 H | 1.73 | 340 | | |
| 13 | Photoreaction | 6 H | 1.71 | 330 | Good | |
| 14 | Photoreaction | 7 H | 1.72 | 340 | Good | |
| 15 | Heat reaction | 6 H | 1.69 | 340 | | |
| 16 | Photoreaction | 6 H | 1.69 | 340 | | ○ |
| 17 | Photoreaction | 7 H | 1.69 | 340 | | ○ |
| 18 | Heat reaction | 6 H | 1.73 | 340 | | |
| 19 | Heat reaction | 6 H | 1.69 | 340 | | |
| 20 | Photoreaction | 7 H | 1.73 | 340 | | |
| 21 | Photoreaction | 7 H | 1.73 | 340 | | |
| 22 | Photoreaction | 7 H | 1.73 | 340 | | |
| 23 | Heat reaction | 7 H | 1.69 | 340 | | |
| 24 | Photoreaction | 7 H | 1.69 | 340 | | |
| 25 | Photoreaction | 7 H | 1.69 | 340 | | |
| 26 | Heat reaction | 6 H | 1.72 | 335 | | |
| 27 | Photoreaction | 6 H | 1.72 | 335 | | |
| 28 | Photoreaction | 6 H | 1.72 | 335 | | |
| 29 | Heat reaction | 6 H | 1.69 | 350 | | |
| 30 | Heat reaction | 6 H | 1.73 | 335 | | |
| 31 | Heat reaction | 7 H | 1.73 | 340 | | |
| 32 | Heat reaction | 7 H | 1.73 | 340 | | |
| 33 | Heat reaction | 7 H | 1.73 | 340 | | |
| 34 | Heat reaction | 7 H | 1.74 | 350 | | |

As is apparent from Tables 5 and 6, the cured films obtained in Examples 9 to 34 had a high pencil hardness and good refractive index and heat resistance. In Example 9, Monofunctional Monomer 1 was liquid at room temperature and could dissolve Compound 1, and, thus, a liquid composition could be obtained without the addition of a solvent. Further, Monofunctional monomer 1 per se had a function as a photopolymerization initiator, and, thus, the compositions of Examples 9 and 12 were cured by a photoreaction even in the absence of a photopolymerization initiator. In Examples 13 and 14, a 5 μm-line pattern was adhered to the substrate even at a low exposure of 10 mJ/cm². The compositions of Examples 16 and 17 had excellent patterning properties.

Evaluation of Flatness

Examples 35 to 38

(Material)
Compounds Repented by the General Formula (1)
Compound 1: Compound obtained in Synthesis Example 1
Solvent
Solvent 1: cyclohexanone (boiling point: 156° C., contact angle on aluminum substrate: 27°, contact angle on glass substrate: 2°)
Solvent 3: tetrahydrofuran (boiling point: 66° C., contact angle on aluminum substrate: 15°, contact angle on glass substrate: 0°)
Solvent 4: diethylene glycol dibutyl ether (boiling point: 256° C., contact angle on aluminum substrate: 0°, contact angle on glass substrate: 5°)
Solvent 5: 1,6-hexanediol diacrylate (boiling point: 260° C., contact angle on aluminum substrate: 30°, contact angle on glass substrate: 3°)

The contact angle on glass substrate was measured with EAGLE XG (registered trademark) glass substrate (manufactured by Corning Incorporated).

(Preparation of Composition and Evaluation of Flatness)

Compound 1 in an amount (parts by mass) specified in Table 7 was homogenously dissolved in a solvent of the type and amount (parts by mass) specified in Table 7 at room temperature to obtain a composition. In order to evaluate the flatness of the cured film obtained from the composition, the composition was coated with a spin coater on an aluminum substrate having grooves having a width of 1 μm and a depth of 0.7 μm, and the coating was prebaked at 100° C. for 120 sec to form a dried coating film (film thickness 2.0 μm). The dried coating film was postbaked at 230° C. for 20 min to form a cured film (film thickness 1.7 μm). The film thickness is a value measured in a groove-free portion on the surface of the substrate. The cross section of the cured film was observed under SEM, and the flatness of the cured film was evaluated according to the following criteria.

○: Regardless of the presence or absence of grooves, the surface of the cured film was free from noticeable irregularities, and the flatness was good.

x: Irregularities were noticed on the surface of the cured film depending upon the presence or absence of the grooves, and the flatness was poor.

TABLE 7

| Example | Compound 1 Amount | Solvent Type | Amount | Type | Amount | Flatness |
|---|---|---|---|---|---|---|
| 35 | 10 | Solvent 1 | 90 | — | — | ○ |
| 36 | 10 | Solvent 1 | 89 | Solvent 3 | 1 | ○ |
| 37 | 10 | Solvent 1 | 89 | Solvent 4 | 1 | ○ |
| 38 | 10 | Solvent 1 | 89 | Solvent 5 | 1 | ○ |

As is apparent from Table 7, for all the solvents used, the cured film obtained from Compound 1 had good flatness.

The invention claimed is:

1. A composition comprising a vinyl-group-containing compound represented by the following general formula (1), and at least one other component selected from photopolymerization initiators, acid generating agents, base generating agents, and photopolymerizable monomers, which differs from the vinyl-group-containing compound represented by the general formula (1):

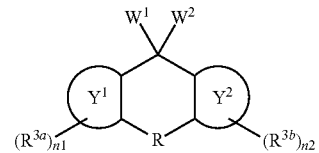

(1)

wherein $W^1$ and $W^2$ each independently represent a group represented by the following general formula (2), a group represented by the following general formula (4), or a hydroxyl group, provided that $W^1$ and $W^2$ do not simultaneously represent a hydroxyl group or the group represented by the following general formula (4); a ring $Y^1$ and a ring $Y^2$, which may be the same or different, represent an aromatic hydrocarbon ring; R represents a single bond, an optionally substituted methylene group, an ethylene group that is optionally substituted and may contain a hetero atom between two carbon atoms, a group represented by —O—, a group represented by —NH—, or a group represented by —S—; $R^{3a}$ and $R^{3b}$ each independently represent a cyano group, a halogen atom, or a monovalent hydrocarbon group; and n1 and n2 each independently represent an integer of 0 to 4,

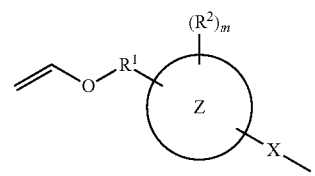

(2)

wherein a ring Z represents a fused polycyclic aromatic hydrocarbon ring; X represents a single bond or a group represented by —S—; $R^1$ represents a single bond or an alkylene group having 1 to 4 carbon atoms; $R^2$ represents a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^4$, a group represented by —$N(R^{4d})_2$, a (meth)acryloyloxy group, a mesyloxy group, or a sulfo group; $R^{4a}$ to $R^{4d}$ each independently represent a monovalent hydrocarbon group; and m is an integer of 0 or more, and

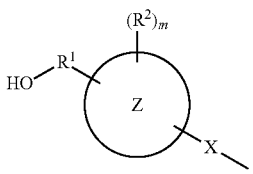

(4)

wherein a ring Z, X, $R^1$, $R^2$, and m are as defined above.

2. The composition according to claim 1, wherein the ring Z is a naphthalene ring.

3. The composition according to claim 1, wherein $R^1$ is a single bond.

4. A composition comprising a monovinyl-group- and mono(meth)acryloyloxy-group-containing compound represented by the following general formula (10), and at least one other component selected from photopolymerization initiators, acid generating agents, base generating agents, and photopolymerizable monomers, which differs from the compound represented by the general formula (10):

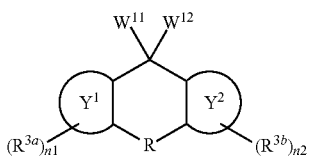

(10)

wherein any one of $W^{11}$ and $W^{12}$ represent a group represented by the following general formula (2) while the other represents a group represented by the following general formula (11) or (12); a ring $Y^1$ and a ring $Y^2$, which may be the same or different, represent an aromatic hydrocarbon ring; R represents a single bond, an optionally substituted methylene group, an ethylene group that is optionally substituted and may contain a hetero atom between two carbon atoms, a group represented by —O—, a group represented by —NH—, or a group represented by —S—; $R^{3a}$ and $R^{3b}$ each independently represent a cyano group, a halogen atom, or a monovalent hydrocarbon group; n1 and n2 each independently represent an integer of 0 to 4,

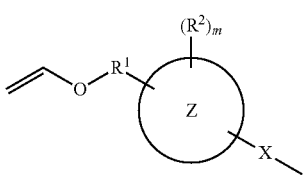

(2)

wherein a ring Z represents an aromatic hydrocarbon ring; X represents a single bond or a group represented by —S—; $R^1$ represents a single bond or an alkylene group having 1 to 4 carbon atoms; $R^2$ represents a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; $R^{4a}$ to $R^{4d}$ each independently represent a monovalent hydrocarbon group; and m is an integer of 0 or more,

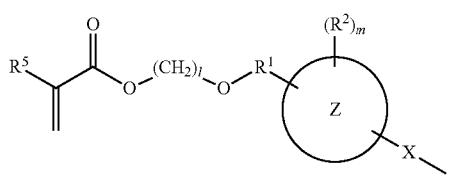

(11)

wherein $R^5$ represents a hydrogen atom or a methyl group; l represents an integer of 1 to 4; and a ring Z, X, $R^1$, $R^2$, and m are as defined above,

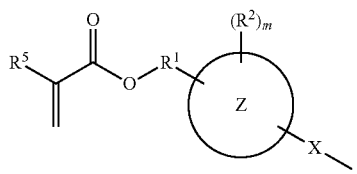

(12)

wherein a ring Z, X, $R^1$, $R^2$, $R^5$, and m are as defined above.

5. The composition according to claim 4, wherein the ring Z represents a benzene ring or a naphthalene ring.

6. The composition according to claim 4, wherein $R^1$ represents a single bond.

7. A composition comprising a (meth)acryloyloxy-group-containing compound represented by the following general formula (19), and at least one other component selected from photopolymerization initiators, acid generating agents, base generating agents, and photopolymerizable monomers which differs from the compound represented by the general formula (19):

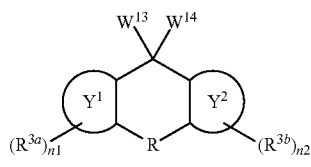

(19)

wherein $W^{13}$ and $W^{14}$ each independently represent a group represented by the following general formula (12), a hydroxyl group, or a (meth)acryloyloxy group, provided that at least one of $W^{13}$ and $W^{14}$ represents a group represented by the following general formula (12); a ring $Y^1$ and a ring $Y^2$, which may be the same or different, represent an aromatic hydrocarbon ring; R represents a single bond, an optionally substituted methylene group, an ethylene group that is optionally substituted and may contain a hetero atom between two carbon atoms, a group represented by —O—, a group represented by —NH—, or a group represented by —S—; $R^{3a}$ and $R^{3b}$ each independently represent a cyano group, a halogen atom, or a monovalent hydrocarbon group; and n1 and n2 each independently represent an integer of 0 to 4,

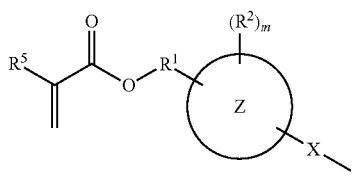

(12)

wherein a ring Z represents a fused polycyclic aromatic hydrocarbon ring; X represents a single bond or a group represented by —S—; $R^1$ represents a single bond or an alkylene group having 1 to 4 carbon atoms; $R^2$ represents a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth) acryloyloxy group, a sulfo group, or a group formed by substituting at least a part of hydrogen atoms bonded to carbon atoms contained in a monovalent hydrocarbon group, a group represented by —$OR^{4a}$, a group represented by —$SR^{4b}$, an acyl group, an alkoxycarbonyl group, a group represented by —$NHR^{4c}$, or a group represented by —$N(R^{4d})_2$ with a monovalent hydrocarbon group, a hydroxyl group, a group represented by —$OR^{4a}$, a group represented by —$SR^{4b}$, an acyl group, an alkoxycarbonyl group, a halogen atom, a nitro group, a cyano group, a mercapto group, a carboxyl group, an amino group, a carbamoyl group, a group represented by —$NHR^{4c}$, a group represented by —$N(R^{4d})_2$, a (meth)acryloyloxy group, a mesyloxy group, or a sulfo group; $R^{4a}$ to $R^{4d}$ each independently represent a monovalent hydrocarbon group; $R^5$ represents a hydrogen atom or a methyl group; and m is an integer of 0 or more.

8. The composition according to claim 7, wherein the ring Z is a naphthalene ring.

9. The composition according to claim 7, wherein $R^1$ is a single bond.

10. The composition according to claim 1, which further comprises an acid generating agent or a base generating agent.

11. The composition according to claim 4, further comprising an acid generating agent or a base generating agent.

12. The composition according to claim 7, further comprising an acid generating agent or a base generating agent.

* * * * *